US006355786B1

(12) United States Patent
Zhao

(10) Patent No.: US 6,355,786 B1
(45) Date of Patent: Mar. 12, 2002

(54) PURIFIED AND ISOLATED PROTEIN ZERO RELATED (PZR) AND THERAPEUTIC AND SCREENING METHODS USING SAME

(75) Inventor: Zhizhuang Zhao, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/430,503

(22) Filed: Oct. 29, 1999

Related U.S. Application Data

(60) Provisional application No. 60/106,459, filed on Oct. 30, 1998.

(51) Int. Cl.$^7$ ................................................ C07H 21/02
(52) U.S. Cl. ................ 536/23.1; 435/69.1; 435/91.2; 435/320.1; 514/44; 530/350; 536/23.5; 935/22
(58) Field of Search ............................ 530/350, 387.9; 536/23.7, 23.1, 23.5; 435/69.1, 7.1, 6, 320.1, 91.2; 800/4; 424/184.1, 130.1; 514/44; 935/22

(56) References Cited

U.S. PATENT DOCUMENTS

| | | | |
|---|---|---|---|
| 5,352,660 A | 10/1994 | Pawson |
| 5,580,979 A | 12/1996 | Bachovchin |
| 5,589,375 A | 12/1996 | Ulrich et al. |
| 5,624,816 A | 4/1997 | Carraway et al. |
| 5,693,488 A | 12/1997 | Fang et al. |
| 5,723,593 A | 3/1998 | Lebo et al. |
| 5,739,278 A | 4/1998 | Daum et al. |
| 5,753,687 A | 5/1998 | Mjalli et al. |
| 5,776,902 A | 7/1998 | Bachovchin |
| 5,786,152 A | 7/1998 | Marengere et al. |

FOREIGN PATENT DOCUMENTS

| | | |
|---|---|---|
| WO | WO 94/08600 | 4/1994 |
| WO | WO 96/26961 | 9/1996 |
| WO | WO 96/40113 | 12/1996 |
| WO | WO 96/40276 | 12/1996 |
| WO | WO 97/32598 | 9/1997 |
| WO | WO 98/04712 | 2/1998 |

OTHER PUBLICATIONS

Xia et al. Homo sapiens myelin protein zero–like protein MPZL1 mRNA, complete cdc. Genebank. Direct Submission. Sep. 15, 1998. (see sequence search results).*
Warner et al. Clinical phenotypes of different MPZ (P0) mutations may include Charcot–Marie–Tooth Type 1B, Dejerine–Sottas, and congenital hypomylination. Neuron. vol. 17 (1996) pp. 451–460.*
Ahn et al. The structural and functional diversity of dystrophin. Nature Genetics, vol. 3 (1993) pp. 283–291.*
Cawthon et al. cDNA sequence and genomic structure of EVI2B, a gene lying within an intron of the neurofibromatosis type 1 gene. Genomics. vol. 9 (1991) pp. 446–460.*
Bowie et al. Deciphering the message in protein sequence tolerance to amino acid substitutions. Science. vol. 247 (1990) pp. 1306–1310.*
Bork. Powers and pitfalls in sequence analysis: the 70% hurdle. Genome Research. vol. 10 (2000) pp. 398–400.*
Lazar et al. Transforming growth factor alpha: mutations of aspartic acid 47 and leucine 48 results in different biological activities. Molecular and Cellular Biology. vol. 8., No. 3 (1988) pp. 1247–1252.*
Burgess et al. Possible disscoiation of the heparin binding . . . of a single luysine residue. Journal of Cell Biology. vol. 111 (1990) pp. 2129–2138.*
Scott et al. The Pendred syndrome gene encodes a chloride–iodide transport protein. Nature Genetics. vol. 21 (1999) pp. 440–443.*
Burshtyn et al., "Regulation Through Inhibitory Receptors: Lessons from Natural Killer Cells", Trends in Cell Biology, vol. 7, p. 473–479, (Dec., 1997).
Choe, "Packing of Myelin Protein Zero," Neuron, vol. 17, p. 363–365, (Sep., 1996).
Harding, "From the Syndrome of Charcot, Marie and Tooth to Disorders of Peripheral Myelin Proteins," Brain, vol. 118, p. 809–818, (Nov., 1995).
Saxton et al., "Abnormal Mesoderm Patterning in Mouse Embryos Mutant for the SH2 Tyrosine Phosphatase Shp–2," The EMBO Journal, vol. 16 (No. 9), p. 2352–2364, (Nov., 1997).
Tidow et al., "SH2–Containnig Protein Tyrosine Phosphatases SHP–1 and SHP–2 are Dramatically Increased at the Protein Level in Neutrophils from Patients with Severe Congenital Neutropenia (Kostmann's Syndrome)," Experimental Hematology, vol. 27 (No. 6), p. 1038–1045, (Nov., 1999).
Unkeless et al., "Inhibitory Receptors, ITIM Sequences and Phosphatases," Current Opinion in Immunology, vol. 9, p. 338–343, (Nov., 1997).
Zhao et al., "Altered Expression of Protein–Tyrosine Phosphatase 2C in 293 Cells Affects Protein Tyrosine Phosphorylationn and Mitogen–Activated Protein Kinase Activation," The Journal of Biological Chemistry, vol. 270 (No. 20), p. 11765–1176, (May 19, 1995).
Zheng et al., "Concanavalin A Protects Hair Cells Against Gentamicin Ototoxicity in Rat Cochlear Explant Cultures," Journal of Neurobiology, vol. 39 (No. 1), p. 29–40, (Apr., 1999).

* cited by examiner

Primary Examiner—Jeffrey Stucker
Assistant Examiner—Ulrike Winkler
(74) Attorney, Agent, or Firm—Jenkins & Wilson, P.A.

(57) ABSTRACT

Isolated and purified proteins and nucleic acids including a novel member of the immunoglobulin super-family characterized as having SHP-2 binding activity and cell signaling activity and called protein zero related or PZR, and cDNA encoding the same. Recombinant host cells, recombinant nucleic acids and recombinant proteins are also disclosed, along with methods of producing each. Isolated and purified antibodies to PZR, and methods of producing the same, are also disclosed. PZR is characterized as having SHP-2 binding activity and cell signaling activity and thus, therapeutic methods involving these activities are also disclosed.

8 Claims, 5 Drawing Sheets

```
      GCGCGGGTTGGAGTGTGCCACCCCGGCCGGGGTGGCGGAGAGATCAGAAGCCTCTTCCCAAGCCGAGCCAACCTCAGCGGGACCCGGGCT      90
      CAGGGAACGCGGCGGGGCGGCGGGGGACTGTGCTCAGTGGCGACGATGGCAGCGTCCGGAGCGGGCGTGATTGCAGCCCCAGACAGC      180
                                   M  A  A  S  A  G  A  G  A  V  I  A  A  P  D  S
  1   CGGCGCCTGGCTGCGTCGTGCTCGTGGCGGCGCTTGGCCTCCTGACAGCTGGAGTATCAGCCTTGGAAGTATATACGCCAAAGAAATC      270
 17   R  R  W  L  W  S  V  L  A  A  L  G  L  L  T  A  G  V  S  A  L  E  V  Y  T  P  K  E  I
      TTCGTGGCAAATGTACACAAGGGAAGCTGCTGACCTGCAAGTTCAAGTCTACTACAGTCTACGACTGGGCGGGTGACCTGACCTCTGGAGCTTC      360
 47   F  V  A  N  G  T  Q  G  K  L  T  C  K  F  K  S  T  T  G  G  L  T  S  V  S  W  S  F
      CAGCCAGAGGGGGCCGACACTACTGTCGTTTTCCACTACTCCCAAGGCAAGTGTACCTTGGGAATTATCCACCATTAAAGACAGA      450
 77   Q  P  E  G  A  D  T  T  V  S  F  F  H  Y  S  Q  G  Q  V  Y  L  G  N  Y  P  P  F  K  D  R
      ATCAGCTGGGCTGGAGACCTTGACAAGAAGATGCATCAACATAGAAAATATGCAGTTTATACACAATGGCACCTATATCTGTGAT      540
107   I  S  W  A  G  D  L  D  K  K  D  A  S  I  N  E  N  M  Q  F  I  H  N  G  T  Y  I  C  D
      GTCAAAAACCCTCCTGACATCGTTGTCCAGCCTGGACACATTAGGCTCTATGTCGTAGAAAAAGAGAATTTGCCTGTGTTTCCAGTTGG      630
137   V  K  N  P  P  D  I  V  V  Q  P  G  H  I  R  L  Y  V  V  E  K  E  N  L  P  V  F  P  V  W
      GTAGTGCTGGGCATAGTTACTGCTGTCGTGCTCTAGGTCTCCTAGGTCTCACTCTGCTCATCAGCATGATTCTGGCTGTCCTCTATAGAAGAAAACTCT      720
167   V  V  V  G  I  V  T  A  V  V  L  G  L  T  L  L  L  I  S  M  I  L  A  V  L  Y  R  R  K  N  S
      AAACGGGATTACACTGGCTGCAGTACATCAGAGAGTTTGTCACCAGTTAAGCAGGCTCCCCTCCGACACTGAGGGTCTT      810
197   K  R  D  Y  T  G  C  S  T  S  E  S  L  S  P  V  K  Q  A  P  R  K  S  P  S  D  T  E  G  L
      GTAAAGAGTCTGCCTTCTGGATCTCACCAGGGCCCAGTCATATATGCACAGTTAGACCATGACCATCACAGTGACAAGATTAAC      900
227   V  K  S  L  P  S  G  S  H  Q  G  P  V  I  Y  A  Q  L  D  H  S  G  G  H  H  S  D  K  I  N
      AAGTCAGAGTCTGTGTGTATGCGGATATCCGAAAGAATTAAGAGAATACCTAGCAAGAACATATCCTCAGCAAGAAACAAACTGGAC      990
257   K  S  E  S  V  V  Y  A  D  I  R  K  N  *
      TCTCGTGCAGAAATGTAGCCCATTACCACATGCCTTAGCCTGGAGACCCAGGCAAGGACAAGTACACGTGTACTCACAGAGGGAGAGAAAG      1080
      ATGTGTACAAAGGATATGTATAAATATTCTATTTAGTCATCCTTAAAAAAAAAAAAAAAAAAAAAAAAAA      1151

```
PZR     40  VYTPKEIFVANGTQGKLTCKFKSTSTTGGLTSVSWSFQPE
                VYT +E+    A G++   L C F S+     S +W +QPE
P0       9  VYTDREVHGAVGSRVTLHCSFWSSEWVSDDISFTWRYQPE

PZR     80  GADTTVSFFHYSQGQVYLGNYPPFKDRISWAGDLDKKDAS
            G    +S FHY++GQ Y+       FK+RI W GD   KD S
P0      49  GGRDAISIFHYAKGQPYIDEVGTFKERIQWVGDPRWKDGS

PZR    120  INIENMQFIHNGTYICDVKNPPDIVVQPGHIRLYVVEK
            I I N+ +  NGT+ CDVKNPPDIV +   + LYV EK
P0      89  IVIHNLDYSDNGTFTCDVKNPPDIVGKTSQVTLYVFEK
```

B

```
PZR      V I Y A Q L D H
FcγRIIB  V V Y A A D I R K
KIR      I T Y S L L K H
LAIR-1   V T Y A Q L D H
         S V Y T E L P N
         V T Y A Q L D H
SIRP     I T Y A A V A R
         I T Y A D L N L
         L T Y A D L D M
```

FIGURE 2

```
mPZR:   MAEAVGAVALIAAPARRRWLWSVLAAMLGLLTARISALEVHTPKEIFVVN          50
        MA  GA A IAAP  RRWLWSVLAA LGLLTA  SALEV TPKEIFV N
hPZR:   MAASAGAGAVIAAPDSRRWLWSVLAAALGLLTAGVSALEVYTPKEIFVAN mPZR:   GTQGKLTCTFDSPNTTGWLTTVSWSFQPDGTDSAVSFFHYSQGQVYIGDY         100
        GTQGKLTC F S  TTG LT VSWSFQP G D  VSFFHYSQGQVY G Y
hPZR:   GTQGKLTCKFKSTSTTGGLTSVSWSFQPEGADTTVSFFHYSQGQVYLGNY mPZR:   PPFKDRVTWAGDLDKKDASINIENIQAVHNGTYICDVKNPPDIVVRPGHI         150
        PPFKDR  WAGDLDKKDASINIEN Q  HNGTYICDVKNPPDIVV PGHI
hPZR:   PPFKDRISWAGDLDKKDASINIENMQFIHNGTYICDVKNPPDIVVQPGHI mPZR:   RLHVVEIDNLLVFLVWVVVGTVTAVVLGLTLLISLVLVVLYRRKHSKRDY         200
        RL VVE  NL VF VWVVVG VTAVVLGLTLLIS  L VLYRRK SKRDY
hPZR:   RLYVVEKENLPVFPVWVVVGIVTAVVLGLTLLISMILAVLYRRKNSKRDY mPZR:   TGCSTSERLSPVKQAPRKCPSDTEGLVKSPPSAGSHQGPVIYAQLDHSDG         250
        TGCSTSE LSPVKQAPRK PSDTEGLVKS PS GSHQGPVIYAQLDHS G
hPZR:   TGCSTSESLSPVKQAPRKSPSDTEGLVKSLPS-GSHQGPVIYAQLDHSGG mPZR:   HHSGKINKSESVVYADIRKD                                       270
        HHS KINKSESVVYADIRK
hPZR:   HHSDKINKSESVVYADIRKN                                       269 hPZR = SEQ ID NO:2 mPZR = SEQ ID NO:26
```

PURIFIED AND ISOLATED PROTEIN ZERO RELATED (PZR) AND THERAPEUTIC AND SCREENING METHODS USING SAME

PRIORITY APPLICATION INFORMATION

This application is a regular United States patent application under 35 U.S.C. § 111(a) based on and claiming priority to United States Provisional Application Ser. No. 60/106,459 filed Oct. 30, 1998, the entire contents of which are herein incorporated by reference.

GRANT STATEMENT

This work was supported by National Institutes of Health (NIH) grants HL57393, CA75218 and CA-69485. Thus, the U.S. Government has certain rights in the invention.

TECHNICAL FIELD

The present invention relates generally to isolated and purified proteins that modulate SHP-2 biological activity and modulate cell signaling, and to nucleic acids encoding the same. More particularly, the present invention relates to an isolated and purified transmembrane protein designated as "protein zero related" or "PZR" that binds the tyrosine phosphatase SHP-2, and an isolated and purified polynucleic acid encoding the same.

Table of Abbreviations

| | |
|---|---|
| BSA | Bovine serum albumin |
| EGF | epidermal growth factor |
| EST | expressed sequence tags |
| FcγRB | an ITIM-containing hematopoietic cell protein |
| GC-MS | gas chromatography-mass spectroscopy |
| HAT | cell culture media comprising hypoxanthine, aminopterin, and thymidine |
| HPLC | high pressure liquid chromatography |
| ITIM | immunoreceptor tyrosine-based inhibitory motif |
| kDa | kilodalton(s) |
| KIR | an ITIM-containing hematopoietic cell protein |
| KLH | keyhole limpet hemocyanin |
| LAIR | an ITIM-containing hematopoietic cell protein |
| Myr | myristoylation |
| PCR | polymerase chain reaction |
| PDGF | platelet-derived growth factor |
| PTK | protein tyrosine kinase |
| PTP | protein tyrosine phosphatase |
| PZR | protein zero related |
| hPZR | human PZR |
| hPZR1B | alternatively spliced human PZR |
| mPZR | mouse PZR |
| PZRX | intracellular domain truncated PZR |
| RACE | rapid amplification of cDNA ends |
| SH2 | Src homology 2 domain |
| SHP-1 | a protein tyrosine phosphatase |
| SHP-2 | a protein tyrosine phosphatase |
| SIRP/SHPS-1 | an ITIM-containing putative SHP-2 substrate |
| TIGR | The Institute for Genomic Research |

BACKGROUND ART

Protein tyrosine phosphatases (PTPs) represent a highly diverse family of enzymes that have a pivotal role in cell proliferation, differentiation, and transformation. Fischer, E. H., Charbonneau, H., and Tonks, N. K. (1991) *Science* 253:401–6; Walton, K. M. and Dixon, J. E. (1993) *Annu. Rev. Biochem.* 62:101–20; Hunter, T. (1995) *Cell* 80:225–236. SHP-1 and SHP-2, representing a subfamily of PTPs containing SH2 domains have been extensively studied in recent years. Zhao, Z, Shen, S. H. and Fischer, E. H. (1995) *Adv. in Protein Phosphatases* 9:297–317; Streuli, M. (1996) *Curr. Opinion in Cell Biol.* 183: 182–188; Scharenberg, A. M. and Kinet, J. P. (1996) *Cell* 87:961–964; Tonks, N. K., & Neel, B. G. (1996) *Cell* 87:365–368; Frearson, J. A. and Alexander, D. R. (1997) *Bioessays* 19;417427; Ulyanova, T., Blasioli, J., and Thomas, M. L. (1997) *Immunolog. Res.* 16:101–113; Byon, J. C., et al. (1997) *Proc. Soc. Exp. Biol. & Med.* 216:1–20; Neel, B. G. and Tonks, N. K. (1997) *Curr. Opin. Cell. Biol.* 9:193–204.

SHP-1 and SHP-2 share nearly 60% overall sequence identity and are regulated in similar manners. Nevertheless, in many systems, they have distinct physiological functions. SHP-1 has a negative role in proliferation of hematopoietic cells whereas SHP-2 is a positive transducer of growth factor signal transduction. This distinction in functions is presumably due to different physiological targets.

Recently, a number of putative substrates of SHP-1 and SHP-2 have been identified. Xiao, S., et al. (1994) *J. Biol. Chem.* 269:21244–21248; Milarski, K. L. and Saltiel, A. L. (1994) *J. Biol. Chem.* 269:21239–21243; Noguchi, T., et al. (1994) *Mol. Cell. Biol.* 14:6674–6682; Yamauchi, K., et al. (1995) *Proc. Natl. Acad. Sci. U.S.A.* 92:664–668; Yamauchi, K., et al. (1995) *J. Biol. Chem.* 270:17716–17722; Frearson, J. A., Yi, T., and Alexander, D. R. (1996) *Eur. J. Immunol.* 26:1539–1543; Valiante, N. M., et al. (1996) *J. Exp. Med.* 184:2243–2250; Carlberg, K. and Rohrschneider, L. R. (1997) *J. Biol. Chem.* 272:15943–15950; Ruff, S. J., Chen, K., and Cohen S. (1997) *J. Biol. Chem.* 272:1263–1267; Gu, H., Griffin, J. D., and Neel, B. G. (1997) *J. Biol. Chem.* 272:16421–16430; Jiao, H., et al. (1997) *Exp. Hematol.* 25:592–600. One of them, designated as SIRP or SHPS-1, has been cloned (Kharitonenkov, A., et al. (1997) *Nature* 386:181–186; Fujioka, Y., et al. (1996) *Mol. Cell. Biol.* 16:6887–6899). Overexpression of catalytically inactive mutants of SHP-1 and SHP-2 resulted in the identification of several hyper-phosphorylated proteins associated with the inactive SHP-1 and/or SHP-2 (Zhao, Z., et al. (1995) *J. Biol. Chem.* 270:11765–17769; Su, L., et al. (1996) *J. Biol. Chem.* 271:10385–10390.

Although a number of putative substrates of SHP-2 have been identified, little is known at the molecular level about the signaling mechanisms of SHP-2. This lack of knowledge represents a serious deficiency in the art in view of the effects of SHP-2 as described above. Therefore, further characterization of SHP-2 signaling in vertebrates, particularly in mammals, and more particularly in humans is needed. A novel isolated and purified polypeptide having a role in SHP-2 signaling would have broad utility in view of the above-described various and multiple physiological roles of SHP-2.

SUMMARY OF THE INVENTION

The present invention contemplates an isolated and purified vertebrate protein, referred to herein as "protein zero related" or "PZR", which plays a role in SHP-2-mediated signaling. More preferably, a polypeptide of the invention is a recombinant polypeptide. Even more preferably, a polypeptide of the present invention comprises a mammalian PZR. Even more preferably, a polypeptide of the present invention comprises a human PZR. Even more preferably, a polypeptide of the present invention comprises the amino acid residue sequence of any of SEQ ID NOs:1–8 and 17–48.

The present invention also provides an isolated and purified polynucleotide that encodes a polypeptide that plays a role in SHP-2-mediated signaling. In a preferred embodiment, a polynucleotide of the present invention comprises a DNA molecule from a vertebrate species. A preferred vertebrate is a mammal. A preferred mammal is a human. More preferably, a polynucleotide of the present invention encodes a polypeptide designated PZR. Even more preferred, a polynucleotide of the present invention encodes a polypeptide comprising the amino acid residue sequence of any of SEQ ID NOs:1–8 and 17–48. Most preferably, an isolated and purified polynucleotide of the invention comprises the nucleotide base sequence of any of SEQ ID NOs:1–8 and 17–48.

In another embodiment, the present invention provides an antibody immunoreactive with a PZR polypeptide as described above. SEQ ID NOs:1–8 and 17–48 sets forth nucleotide and amino acid sequences from representative vertebrates, human and mouse. Also contemplated by the present invention are antibodies immunoreactive with homologues or biologically equivalent PZR polynucleotides and polypeptides found in other vertebrates. Preferably, an antibody of the invention is a monoclonal antibody. More preferably, the PZR polypeptide comprises human PZR. Even more preferably, the PZR polypeptide comprises the amino acid residue sequence of any of SEQ ID NOs:1–8 and 17–48.

In another aspect, the present invention contemplates a process of producing an antibody immunoreactive with a PZR as described above, the process comprising: (a) transfecting a recombinant host cell with a polynucleotide that encodes a PZR polypeptide having a SHP-2 activity-modulating function; (b) culturing the host cell under conditions sufficient for expression of the polypeptide; (c) recovering the polypeptide; and (d) preparing the antibody to the polypeptide. SEQ ID NOs:1–8 and 17–48 set forth nucleotide and amino acid sequences from representative vertebrates, human and mouse. Preferably, the host cell is transfected with the polynucleotide of any of SEQ ID NOs:1–8 and 17–48. Even more preferably, the present invention provides an antibody prepared according to the process described above. Also contemplated by the present invention is the use of homologues or biologically equivalent polynucleotides and polypeptides found in other vertebrates to produce antibodies.

Alternatively, the present invention provides a process of detecting a PZR polypeptide as described above, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a PZR polypeptide as described above, wherein the process comprises hybridizing the messenger RNA transcript with a polynucleotide sequence that encodes that polypeptide to form a duplex; and detecting the duplex. Alternatively, the present invention provides a process of detecting a DNA molecule that encodes a PZR polypeptide as described above, wherein the process comprises hybridizing DNA molecules with a polynucleotide that encodes a PZR polypeptide having a SHP-2 binding function to form a duplex; and detecting the duplex.

In another aspect, the present invention contemplates an assay kit for detecting the presence of a PZR polypeptide in a biological sample, where the kit comprises a first container containing a first antibody capable of immunoreacting with a vertebrate PZR polypeptide having a SHP-2 binding function, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides an assay kit for detecting the presence, in biological samples, of a PZR polypeptide, the kits comprising a first container that contains a second polynucleotide identical or complementary to a segment of at least 10 contiguous nucleotide bases of a polynucleotide that encodes a PZR polypeptide having a SHP-2 binding function.

In another embodiment, the present invention contemplates a diagnostic assay kit for detecting the presence, in a biological sample, of an antibody immunoreactive with a PZR polypeptide, the kit comprising a first container containing a PZR polypeptide having a SHP-2 binding function that immunoreacts with the antibody, with the polypeptide present in an amount sufficient to perform at least one assay.

In still a further embodiment, this invention pertains to therapeutic methods based upon the SHP-2 binding function of PZR as described herein. Such therapeutic methods include administration of a soluble form of the PZR protein and gene therapy approaches using an isolated and purified polynucleotide of the present invention. Therapeutic methods in accordance with the present invention are also contemplated to have application in the treatment of type 1B Charcot-Marie-Tooth disease.

Thus, a key aspect of this invention pertains to the discovery of the novel PZR protein and nucleic acid encoding the PZR protein. Preferred nucleic acid and amino acid sequences for PZR are described in any of SEQ ID NOs:1–8 and 17–48.

It is another aspect of this invention that the novel PZR protein binds with SHP-2 to modulate SHP-2 biological activity.

It is thus another aspect of this invention to provide a purified and isolated PZR polypeptide having a SHP-2 binding function.

The foregoing aspects and embodiments have broad utility given the biological significance of SHP-2, as is known in the art. By way of example, the foregoing aspects and embodiments are useful in the preparation of screening assays and assay kits that are used to identify compounds that affect or modulate PZR or SHP-2 biological activity, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Some of the aspects and objects of the invention having been stated hereinabove, other aspects and objects will become evident as the description proceeds, when taken in connection with the accompanying Examples and Drawings as best described hereinbelow.

BRIEF DESCRIPTION OF THE DRAWINGS

FIG. 1 depicts the nucleotide sequence of the PZR cDNA (SEQ ID NO:1) and amino acid sequence (SEQ ID NO:2) of the PZR protein. Amino acid residues are numbered on the left, and nucleotide positions on the right. The putative signal sequence and transmembrane segment are underlined. The ITIM sequences in the cytosolic domain are bold-faced. Two putative N-linked glycosylation sites and two cysteinyl residues potentially involved in disulfide bond formation in an immunoglobulin-like domain in the extracellular domain are underlined and bold-faced. Putative tyrosine phosphorylation site Y200 is shown in italic and bold face.

FIG. 2 depicts sequence alignment of PZR with myelin P0 and with ITIMS.

FIG. 2A depicts sequence alignment of PZR with myelin P0. Identical amino acid residues are shown in the middle. "+" denotes similar residues.

FIG. 2B depicts sequence alignment of ITIMs. Note that all the proteins listed except for FcyRIIB have two ITIMs.

FIG. 3 depicts amino acid sequence alignment between mouse PZR (SEQ ID NO:26) and human PZR (SEQ ID NO:2).

DETAILED DESCRIPTION OF THE INVENTION

Figure 4:
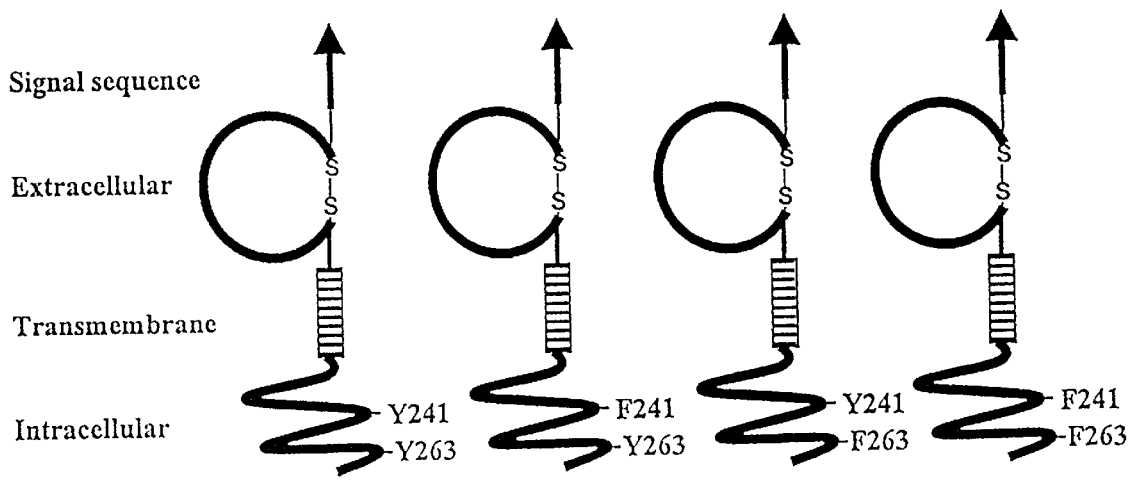
FIG. 4 is a schematic diagram of PZR constructs. Y and F denote tyrosyl and phenylalanyl residues, respectively.

Disclosed herein is a transmembrane protein that belongs to the immunoglobulin superfamily and that specifically binds tyrosine phosphatase SHP-2 which has two SH2 domains. Overexpression of a catalytically inactive mutant of tyrosine phosphatase SHP-2 in 293 cells resulted in hyperphosphorylation of a glycoprotein specifically associated with the enzyme. The protein has been purified to near homogeneity. Based on the amino acid sequences of peptides obtained from the protein, a full length cDNA was isolated. The cDNA encodes a protein with a single transmembrane segment and a signal sequence. The protein is designated PZR for Protein Zero Related. Transfection of the PZR cDNA in Jurkat cells gave rise to a protein of expected molecular size. Stimulation of cells with pervanadate resulted in tyrosine phosphorylation of PZR and a near-stoichiometric association of PZR with SHP-2. Northern blotting analyses revealed that PZR is widely expressed in human tissues and is particularly abundant in heart, placenta, kidney, and pancreas. As a binding protein and a substrate of SHP-2, PZR protein has an important role in cell signaling.

Thus, a tyrosine-phosphorylated transmembrane protein designated as PZR has been purified from human cells and subsequently cloned in accordance with the present invention. The PZR cDNA has an open reading frame comprising 807 nucleotides encoding novel protein of 269 amino acids. The deduced amino acid sequence contains a extracellular domain (also referred to herein as an ectodomain) with an terminal signal sequence, a membrane-spanning segment, and a C-terminal intracellular portion. The extracellular domain of the protein contains a single immunoglobulin-like domain displaying 46% sequence identity to that of myelin P0, a major transmembrane glycoprotein of the myelin sheath that has major pathological implications. The intracellular portion of the protein shows no significant sequence identity to an known protein except for two immunoreceptortyrosine-based inhibitory motifs (ITIMs). PZR specifically binds SHP-2, a SH2 domain-containing tyrosine phosphatase that is crucial for cell development.

U.S. Pat. No. 5,589,375 describes the purified and isolated SHP-2, or PTP-1D, protein tyrosine phosphatase itself, and the contents of U.S. Pat. No. 5,589,375 are herein incorporated by reference. Tyrosine phosphorylated ITIMs of PZR and SH2 domains of SHP-2 mediate the binding. Unlike most of the other ITIM-containing proteins that are found only in hematopoietic cells, PZR is widely expressed in human tissues and is particularly abundant in heart, placenta, kidney, and pancreas.

The PZR gene has been localized to chromosome 1q24, a region implicated in prostate cancer. The structural features and functions of PZR make the PZR cDNA and the PZR protein therapeutically important. As a participant in cell signaling, the PZR protein is a target for drug development. Ligands, chemical compounds, and antibodies that bind PZR to stimulate or inhibit cell signaling through PZR and affect cell behaviors are thus contemplated in accordance with the present invention.

Biologically active PZR specifically recruits tyrosine phosphatase SHP-2 to the plasma membrane, and thus, has a role in signal transduction that controls cell behaviors. The PZR gene and the PZR gene product have important therapeutic applications, and the PZR protein is a good target for therapeutic drug development. Thus, a screening method using the PZR protein to identify compounds that modulate these binding characteristics is also contemplated in accordance with the present invention.

It is noted that SHP-2 is a positive transducer of growth factor signal transduction. As described herein, the intracellular domain of PZR has ITIMs that are responsible for recruiting SHP-2, and thus any peptides or compounds that interfere with the process could block signal transduction. The modulation of SHP-2 activity to accomplish a desired effect on cell signaling is also contemplated in accordance with the present invention.

The extracellular domain of PZR is likely involved in protein-protein and protein-ligand interactions. A soluble form of PZR containing the extracellular domain is contemplated in accordance with the present invention, for use in binding PZR and other related protein, thereby enhancing or inhibiting (i.e. modulating) cell signaling. A soluble form of PZR can be produced by expressing a truncated form of the protein in bacterials or other expression systems, as described herein below. Since PZR has signal sequence at the N-terminus, an alternately spliced form of PZR (e.g. SEQ ID NOs: 17–24 and 33– 40) that can optionally code for a secreted protein is contemplated in accordance with the present invention.

Mutation of myelin P0 has been shown to be responsible for the type 1B Charcot-Marie-Tooth disease. PZR shares a high sequence identity with myelin P0, thus suggesting pathological implications. In this regard, the PZR gene can be used for gene therapy in accordance with the present invention.

PZR can serve as a standard in an assay for tyrosine phosphatase and/or tyrosine kinase activity in accordance with the present invention. A tyrosine phosphatase is an enzyme which functions to remove a phosphate moiety from a biological molecule while a tyrosine kinase is an enzyme that facilitates the attachment of a phosphate moiety to a biological molecule. The attachment and removal of phosphate moieties is a common and important mechanism that regulates the activity of biological molecules in vivo. The PZR protein has been determined herein to be readily phosphorylated and therefore can be used as a standard or control in an assay to determine the activity of a particular tyrosine kinase or tyrosine phosphatase.

A. DEFINITIONS AND TECHNIQUES AFFECTION GENE PRODUCTS AND GENES

The present invention concerns nucleic acid segments (preferably DNA segments), isolatable from eukaryotic cells, preferably cells from vertebrate tissue, more preferably from mammalian tissue, and even more preferably from human tissue, which are free from genomic DNA and which are capable of conferring SHP-2 binding activity, cell signaling activity or other biological activity in accordance with the present invention in a recombinant host cell when incorporated into the recombinant host cell, As used herein, the term "mammalian tissue" refers to, among others, normal mammalian kidney issues, as exemplified by, but not limited to, human kidney tissues and to abnormal mammalian tissues, as exemplified by, but not limited to, tumor tissues. DNA segments capable of conferring a SHP-2 binding function may encode complete PZR polypeptides, cleavage products and biologically actively functional domains thereof.

The terms "PZR polypeptide", "PZR gene product", and "PZR", as used in the specification and in the claims refer to proteins having amino acid sequences which are substantially identical to the respective native PZR amino acid sequences (including alternatively spliced native PZR sequences) and which are biologically active in that they are capable of SHP-2 binding activity, cell signaling activity or other biological activity in accordance with the present invention, or are capable of cross-reacting with an anti-PZR antibody raised against a PZR. Such sequences are disclosed herein. The terms "PZR polypeptide", "PZR gene product", and "PZR" also include analogs of PZR molecules which exhibit at least some biological activity in common with native PZR. Furthermore, those skilled in the art of mutagenesis will appreciate that other analogs, as yet undisclosed or undiscovered, may be used to construct PZR analogs. There is no need for a "PZR polypeptide" or a "PZR" to comprise all, or substantially all, of the amino acid sequence of the native PZR genes. Shorter or longer sequences are anticipated to be of use in the invention.

The terms "PZR gene", "PZR gene sequence" and "PZR gene segment" refer to any DNA sequence that is substantially identical to a DNA sequence encoding a PZR as defined above. The terms also refer to RNA, or antisense sequences, compatible with such DNA sequences. A "PZR gene", "PZR gene sequence" and "PZR gene segment" may also comprise any combination of associated control sequences. Since the PZR gene product has signal sequence at the N-terminus, an alternately spliced form of a PZR gene that codes for a secreted PZR protein is also contemplated to be encompassed by the term "PZR gene".

The term "substantially identical", when used to define either a PZR or PZR amino acid sequence, or a PZR gene or PZR nucleic acid sequence, means that a particular sequence, for example, a mutant sequence, varies from the sequence of a natural PZR by one or more deletions, substitutions, or additions, the net effect of which is to retain at least some of biological activity of PZR. Alternatively, DNA analog sequences are "substantially identical" to specific DNA sequences disclosed herein if: (a) the DNA analog sequence is derived from coding regions of the natural PZR or PZR gene; or (b) the DNA analog sequence is capable of hybridization of DNA sequences of (a) under moderately stringent conditions and which encode biologically active PZR or PZR gene; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

A.1. Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

A.2. Nucleic Acid Sequences

In certain embodiments, the invention concerns the use of PZR genes and gene products that include within their respective sequences a sequence which is essentially that of the PZR gene, or the corresponding protein. The term "a sequence essentially as that of PZR or PZR gene", means that the sequence substantially corresponds to a portion of a PZR or PZR gene and has relatively few bases or amino acids (whether DNA or protein) which are not identical to those of a PZR or PZR gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a PZR or PZR gene, will be sequences which are "essentially the same".

PZR and PZR genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1). Thus, when referring to the sequence examples presented in SEQ ID NOs:1, 3, 5, 7, 17, 19, 21, 23, 25, 27, 29, 31, 33, 35, 37, 39, 41, 43, 45 and 47, applicants contemplate substitution of functionally equivalent codons of Table 1 into the sequence examples of SEQ ID NOs:1, 3, 5, 7, 17, 19, 21, 23, 25, 27, 29, 31, 33, 35, 37, 39, 41, 43, 45 and 47. Thus, applicants are in possession of amino acid and nucleic acids sequences which include such substitutions but which are not set forth herein in their entirety for convenience.

TABLE 1

Functionally Equivalent Codons.

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic Acid | Asp | D | GAC | GAU | | | |
| Glumatic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | k | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | ACG | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See e.g., Wetmur & Davidson, 1968).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a PZR refers to a DNA segment which contains PZR coding sequences, yet is isolated away from, or purified free from, total genomic DNA of Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified PZR gene refers to a DNA segment including PZR coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences, including alternatively spliced sequences and truncated sequences. "Isolated substantially away from other coding sequences" means that the gene of interest, in this case, the PZR gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a PZR that includes within its amino acid sequence the amino acid sequence of any of SEQ ID NOs:2, 4, 6, 8, 18, 20, 22, 24, 26, 28, 30, 32, 34, 36, 38, 40, 42, 44, 46 and 48. In other particular embodiments, the invention concerns isolated DNA segments and recombinant vectors incorporating DNA sequences which encode a protein that includes within its amino acid sequence the amino acid sequence of PZR corresponding to mammalian tissues, including human and mouse tissues. Representative sequences are set forth in SEQ ID NOs:1, 3, 5, 7, 17, 19, 21, 23, 25, 27, 29, 31, 33, 35, 37, 39, 41, 43, 45 and 47.

It will also be understood that this invention is not limited to the particular nucleic acid and amino acid sequences of any of SEQ ID NOs:1–8 and 17–48. Recombinant vectors and isolated DNA segments may therefore variously include the PZR-encoding region itself, include coding regions bearing selected alterations or modifications in the basic coding region, or include encoded larger polypeptides which nevertheless include PZR-encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of SEQ ID NOs:2, 4, 6, 8, 18, 20, 22, 24, 26, 28, 30, 32, 34, 36, 38, 40, 42, 44, 46 and 48. Naturally, where the DNA segment or vector encodes a full length PZR gene product, the most preferred sequence is that which is essentially as set forth in any of SEQ ID NOs:2, 4, 6, 8, 18, 20, 22, 24, 26, 28, 30, 32, 34, 36, 38, 40, 42, 44, 46 and 48 and which encode a protein that exhibits SHP-2 binding activity in for example human kidney cells, as may be determined by for example immunoprecipitation assays, as disclosed herein.

The term "a sequence essentially as set forth in any of SEQ ID NOs:2, 4, 6, 8, 18, 20, 22, 24, 26, 28, 30, 32, 34, 36, 38, 40, 42, 44, 46 and 48" means that the sequence substantially corresponds to a portion of any of SEQ ID NOs:2, 4, 6, 8, 18, 20, 22, 24, 26, 28, 30, 32, 34, 36, 38, 40, 42, 44, 46 and 48 and has relatively few amino acids which are not identical to, or a biologically functional equivalent of, the amino acids of any of SEQ ID NOs:2, 4, 6, 8, 18, 20, 22, 24, 26, 28, 30, 32, 34, 36, 38, 40, 42, 44, 46 and 48. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of any of SEQ ID NOs:2, 4, 6, 8, 18, 20, 22, 24, 26, 28, 30, 32, 34, 36, 38, 40, 42, 44, 46 and 48, will be sequences which are "essentially as set forth in any of SEQ ID NOs:2, 4, 6, 8, 18, 20, 22, 24, 26, 28, 30, 32, 34, 36, 38, 40, 42, 44, 46 and 48".

In particular embodiments, the invention concerns gene therapy methods that use isolated DNA segments and recombinant vectors incorporating DNA sequences which encode a protein that includes within its amino acid sequence an amino acid sequence in accordance with any of SEQ ID NOs:2, 4, 6, 8, 18, 20, 22, 24, 26, 28, 30, 32, 34, 36, 38, 40, 42, 44, 46 and 48. In other particular embodiments, the invention concerns isolated DNA sequences and recombinant DNA vectors incorporating DNA sequences which encode a protein that includes within its amino acid sequence the amino acid sequence of the PZR protein from human or mouse tissue.

In certain other embodiments, the invention concerns isolated DNA segments and recombinant vectors that include within their sequence a nucleic acid sequence essentially as set forth in any of SEQ ID NOs:1, 3, 5, 7, 17, 19, 21, 23, 25, 27, 29, 31, 33, 35, 37, 39, 41, 43, 45 and 47. The term "essentially as set forth in any of SEQ ID NOs:1, 3, 5, 7, 17, 19, 21, 23, 25, 27, 29, 31, 33, 35, 37, 39, 41, 43, 45 and 47" is used in the same sense as described above and means that the nucleic acid sequence substantially corresponds to a portion of any of SEQ ID NOs:1, 3, 5, 7, 17, 19, 21, 23, 25, 27, 29, 31, 33, 35, 37, 39, 41, 43, 45 and 47, respectively, and has relatively few codons which are not identical, or functionally equivalent, to the codons of any of SEQ ID NOs:1, 3, 5, 7, 17, 19, 21, 23, 25, 27, 29, 31, 33, 35, 37, 39, 41, 43, 45 and 47, respectively. Again, DNA segments which encode gene products exhibiting SHP-2 binding activity, cell signaling activity or other biological activity of the PZR gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to any of SEQ ID NOs:1, 3, 5, 7, 17, 19, 21, 23, 25, 27, 29, 31, 33, 35, 37, 39, 41, 43, 45 and 47, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent PZR proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged, e.g. substitution of lie for Leu at amino acid 30 in SEQ ID NOs:3–4, substitution of Ile for Leu at amino acid 244 in SEQ ID NOs:5–6, and substitution of lie for Leu at amino acid 30 and at amino acid 244 in SEQ ID NOs:7–8; substitution of lie for Leu at amino acid 30 in SEQ ID NOs:19–20, substitution of lie for Leu at amino acid 190 in SEQ ID NOs:21–22, and substitution of lie for Leu at amino acid 30 and at amino acid 190 in SEQ ID NOs:23–24; substitution of lie for Leu at amino acid 24 in SEQ ID NOs:27–28, substitution of lie for Leu at amino acid 245 in SEQ ID NOs:29–30, and substitution of lie for Leu at amino acid 24 and at amino acid 245 in SEQ ID NOs:31–32; and substitution of lie for Leu at amino acid 97 in SEQ ID NOs:4344, substitution of lie for Leu at amino acid 152 in SEQ ID NOs:45–46; and substitution of lie for Leu at amino acid 97 and at amino acid 152 in SEQ ID NOs:47–48. Changes designed by man may be introduced through the application of site-directed mutagenesis techniques, e.g., to introduce improvements to the antigenicity of the protein or to test PZR mutants in order to examine SHP-2 binding, cell signaling activity, or other activity at the molecular level.

If desired, one may also prepare fusion proteins and peptides, e.g., where the PZR coding region is aligned within the same expression unit with other proteins or peptides having desired functions, such as for purification or immunodetection purposes (e.g., proteins which may be purified by affinity chromatography and enzyme label coding regions, respectively). One may also prepare truncated (e.g. SEQ ID NOs:41–48) or soluble PZR (e.g. SEQ ID NOs:33–40) for use e.g. in the screening and therapeutic methods of the present invention.

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the PZR gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a PZR gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter and the baculovirus promoter.

In an alternative embodiment, the present invention provides an expression vector comprising a polynucleotide that encodes a vertebrate PZR polypeptide having SHP-2 binding activity, cell signaling activity or other biological activity in accordance with the present invention. Also preferably, an expression vector of the present invention comprises a polynucleotide that encodes a mammalian PZR. More preferably, an expression vector of the present invention comprises a polynucleotide that encodes a polypeptide comprising the amino acid residue sequence of any of SEQ ID NOs:2, 4, 6, 8, 18, 20, 22, 24, 26, 28, 30, 32, 34, 36, 38, 40, 42, 44, 46 and 48. More preferably, an expression vector of the present invention comprises a polynucleotide comprising the nucleotide base sequence of any of SEQ ID NOs:1, 3, 5, 7, 17, 19, 21, 23, 25, 27, 29, 31, 33, 35, 37, 39, 41, 43, 45 and 47. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a PZR polypeptide having SHP-2 binding activity, cell signaling activity or other biological activity in accordance with the present invention. SEQ ID NOs:1–8 and 17–48 sets forth nucleotide and amino acid sequences from representative vertebrates, human and mouse. Also contemplated by the present invention are homologous or biologically equivalent polynucleotides and PZR polypeptides found in other vertebrates. Preferably, a recombinant host cell of the present invention is transfected with the polynucleotide that encodes human PZR. More preferably, a recombinant host cell of the present invention is transfected with the polynucleotide sequence of any of SEQ ID NOs:1, 3, 5, 7, 17, 19, 21, 23, 25, 27, 29, 31, 33, 35, 37, 39, 41, 43, 45 and 47. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the PZR polypeptide in a manner to enable all necessary transcriptional and post-transcriptional modification.

In yet another embodiment, the present invention contemplates a process of preparing a PZR polypeptide comprising transfecting a cell with polynucleotide that encodes a PZR polypeptide having SHP-2 binding activity, cell signaling activity or other biological activity in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of any of SEQ ID NOs:1, 3, 5, 7, 17, 19, 21, 23, 25, 27, 29, 31, 33, 35, 37, 39, 41, 43, 45 and 47. SEQ ID NOs:1–8 and 17–48 set forth nucleotide and amino acid sequences for representative vertebrates, human and mouse. Also contemplated by the present invention are homologues or biologically equivalent PZR polynucleotides and polypeptides found in other vertebrates.

As mentioned above, in connection with expression embodiments to prepare recombinant PZR proteins and peptides, it is contemplated that longer DNA segments will most often be used, with DNA segments encoding the entire PZR protein, functional domains or cleavage products thereof, being most preferred. However, it will be appreciated that the use of shorter DNA segments to direct the expression of PZR peptides or epitopic core regions, such as may be used to generate anti-PZR antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 2,500 nucleotides for a protein in accordance with any of SEQ ID NOs:1–8 and 17–48.

Naturally, the present invention also encompasses DNA segments which are complementary, or essentially complementary, to the sequence set forth in any of SEQ ID NOs:1, 3, 5, 7, 17, 19, 21, 23, 25, 27, 29, 31, 33, 35, 37, 39, 41, 43, 45 and 47. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of any of SEQ ID NOs:1, 3, 5, 7, 17, 19, 21, 23, 25, 27, 29, 31, 33, 35, 37, 39, 41, 43, 45 and 47, will be sequences which are "essentially as set forth in any of SEQ ID NOs:1, 3, 5, 7, 17, 19, 21, 23, 25, 27, 29, 31, 33, 35, 37, 39, 41, 43, 45 and 47". Sequences which are essentially the same as those set forth in any of SEQ ID NOs:1, 3, 5, 7, 17, 19, 21, 23, 25, 27, 29, 31, 33, 35, 37, 39, 41, 43, 45 and 47 may also be functionally defined as sequences which are capable of hybridizing to a nucleic acid segment containing the complement of any of SEQ ID NOs:1, 3, 5, 7, 17, 19, 21, 23, 25, 27, 29, 31, 33, 35, 37, 39, 41, 43, 45 and 47 under relatively stringent conditions. Suitable relatively stringent hybridization conditions are described herein and will be well known to those of skill in the art. For example, stringent hybridization conditions represented by a wash stringency of 0.3 Molar NaCl, 0.03M sodium citrate, 0.1% SDS at 60° C. are contemplated.

A.3. Biologically Functional Equivalents

As mentioned above, modification and changes may be made in the structure of the PZR proteins and peptides described herein and still obtain a molecule having like or otherwise desirable characteristics. For example, certain amino acids may be substituted for other amino acids in a protein structure without appreciable loss of interactive capacity with structures such as, for example, in SHP-2. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventor that various changes may be made in the sequence of the PZR proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where if any changes, for example, in Tyr241 and Tyr263 of PZR which are phosphorylated and are responsible for binding of the SHP-2 through its SH2 domains (see Examples 6–9), could result in a loss of an aspect of the utility of the resulting peptide for the present invention.

Amino acid substitutions, such as those which might be employed in modifying the PZR proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

A.4. Sequence Modification Techniques

Modifications to the PZR proteins and peptides described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, PZR. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Kienow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful PZR or other SHP-2 binding or cell signaling species and is not meant to be limiting as there are other ways in which sequence variants of these peptides may be obtained. For example, recombinant vectors encoding the desired genes may be treated with mutagenic agents to obtain sequence variants (see e.g. a method described by Eichenlaub, 1979) for the mutagenesis of plasmid DNA using hydroxylamine.

A.5. Other Structural Equivalents

In addition to the PZR peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. INTRODUCTION AND EXPRESSION OF GENE PRODUCTS

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

B.1. Vector Construction

In vectors, it is understood that the DNA coding sequences to be expressed, in this case those encoding the PZR gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the PZR promoter for PZR) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream on the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the PZR gene, it is proposed that one will desire to preferably employ a vector construct that will deliver the desired gene to the affected cells. This will, of course, generally require that the construct be delivered to the targeted cells, for example, mammalian smooth muscle cells or mammalian epithelial cells. It is proposed that this may be achieved most preferably by introduction of the desired gene through the use of a viral vector to carry the PZR sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency. Suitable vector-PZR gene constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the BgI I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Where the PZR gene itself is employed it will be most convenient to simply use the wild type PZR gene directly. However, it is contemplated that certain regions of the PZR gene may be employed exclusively without employing the entire wild type PZR gene. It is proposed that it will ultimately be preferable to employ the smallest region needed to modulate cell signaling so that one is not introducing unnecessary DNA into cells which receive either a PZR gene construct. Techniques well known to those of skill in the art, such as the use of restriction enzymes, will allow for the generation of small regions of the PZR gene. The ability of these regions to modulate cell signaling can easily be determined by the assays reported in the Examples. In general, techniques for assessing the modulation of cell signaling are well known in the art.

B.2. Transgenic Non-Human Animals

It is also contemplated to be within the scope of the present invention to prepare a transgenic non-human animal which expresses the PZR gene of the present invention. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); 5,162,215 (transgenic avian species) and U.S. Pat. No. 5,741,957 (transgenic bovine species), the entire contents of each of which are herein incorporated by reference.

With respect to an exemplary method for the preparation of a transgenic mouse, cloned recombinant or synthetic DNA sequences or DNA segments encoding PZR are injected into fertilized mouse eggs. The injected eggs are implanted in pseudo pregnant females and are grown to term to provide transgenic mice whose cells express PZR. The injected sequences are constructed having promoter sequences connected so as to express the desired protein in multiple tissues of the transgenic mouse.

C. GENERATION OF ANTIBODIES

In still another embodiment, the present invention provides an antibody immunoreactive with a polypeptide of the present invention. Preferably, an antibody of the invention is a monoclonal antibody. Techniques for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Techniques for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, interalia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a PZR polypeptide, the process comprising: (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the PZR polypeptide is capable of SHP-2 binding activity, cell signaling activity or other biological activity in accordance with the present invention. Even more preferably, the present invention provides antibodies prepared according to the process described above.

A monoclonal antibody of the present invention can be readily prepared through use of hybridoma techniques such as those exemplified in U.S. Pat. No. 4,196,265, and the phage-displayed techniques disclosed in U.S. Pat. No. 5,260,203, herein incorporated by reference.

A typical technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 $\mu$g of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

D. DETECTING A POLYNUCLEOTIDE OR A POLYPEPTIDE OF THE PRESENT INVENTION

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode a polypeptide of the present invention, wherein the process comprises hybridizing the messenger RNA transcripts with polynucleotide sequences that encode the polypeptide to form duplexes; and detecting the duplex. Alternatively, the present invention provides a process of detecting DNA molecules that encode a polypeptide of the present invention, wherein the process comprises hybridizing DNA molecules with a polynucleotide that encodes that polypeptide to form duplexes; and detecting the duplexes.

D.1. Detecting a Polypeptide of the Present Invention

The present invention provides a process of screening a biological sample for the presence of a PZR polypeptide. Preferably, the PZR polypeptide possesses SHP-2 binding activity, cell signaling activity or other biological activity in accordance with the present invention. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a detection assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary interalia with the biological conditions used, the concentration of antibody and polypeptide and the nature of the sample (e.g., fluid or tissue sample). Techniques for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Techniques for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Techniques for affixing indicators to antibodies are well known in the art. Commercial kits are available.

D.2. Detecting an Anti-Polypeptide Antibody

In another aspect, the present invention provides a process of screening a biological sample for the presence of antibodies immunoreactive with a PZR polypeptide. Preferably the PZR polypeptide possesses SHP-2 binding activity, cell signaling activity or other biological activity in accordance with the present invention. In accordance with such a process, a biological sample is exposed to a PZR polypeptide under biological conditions and for a period of time sufficient for antibody-polypeptide conjugate formation and the formed conjugates are detected.

D.3. Detecting a Polynucleotide That Encodes a PZR Polypeptide

A DNA molecule and, particularly a probe molecule, can be used for hybridizing as an oligonucleotide probe to a DNA source suspected of encoding a PZR polypeptide of the present invention. Preferably the PZR polypeptide possesses SHP-2 binding activity, cell signaling activity or other biological activity in accordance with the present invention. The probing is usually accomplished by hybridizing the oligonucleotide to a DNA source suspected of possessing a PZR gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) tools to detect normal and abnormal DNA sequences in DNA derived from patient's cells; (2) tools for detecting and isolating other members of the polypeptide family and related polypeptides from a DNA library potentially containing such sequences; (3) primers for hybridizing to related sequences for the purpose of amplifying those sequences; (4) primers for altering native PZR DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected PZR gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as that shown in any of SEQ ID NOs:1, 3, 5, 7, 17, 19, 21, 23, 25, 27, 29, 31, 33, 35, 37, 39, 41, 43, 45 and 47. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical techniques, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate reagent, such as a label, for determining hybridization. A wide variety of appropriate indicator reagents are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a reagent visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend interalia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, via the label.

D.4. Assay Kits

In another aspect, the present invention contemplates assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, any of SEQ ID NOs:1, 3, 5, 7, 17, 19, 21, 23, 25, 27, 29, 31, 33, 35, 37, 39, 41, 43, 45 and 47.

In another embodiment, the present invention contemplates assay kits for detecting the presence, in a biological sample, of antibodies immunoreactive with a polypeptide of the present invention, the kits comprising a first container containing a PZR polypeptide, that immunoreacts with the antibodies, with the polypeptide present in an amount sufficient to perform at least one assay. Preferably, the PZR polypeptide possesses SHP-2 binding activity, cell signaling activity or other biological activity in accordance with the present invention. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

E. SCREENING ASSAYS

In yet another aspect, the present invention contemplates a process of screening substances fort heir ability to affect or modulate the biological activity of PZR. The present invention also contemplates a process of screening substances for their ability to affect or modulate the biological activity of PZR to thereby affect or modulate the biological activity of SHP-2. Utilizing the methods and compositions of the present invention, screening assays for the testing of candidate substances can be derived. A candidate substance is a substance which potentially can promote or inhibit the biological activity of PZR by binding, or other intramolecular interaction, with PZR.

E.1. Screening for PZR Modulators

An exemplary method of screening candidate substances fort heir ability to modulate PZR biological activity comprises: (a) establishing replicate test and control samples that comprise a biologically active PZR polypeptide; (b) administering a candidate substance to test sample but not the control sample; (c) measuring the biological activity of PZR in the test and the control samples; and (d) determining that the candidate substance modulates PZR biological activity if the biological activity of PZR measured for the test sample is greater or less than the biological activity of PZR level measured for the control sample. The biological activities of PZR that may optionally be examined in connection with a screening assay of the present invention comprise SHP-2 binding activity, cell signaling activity or other biological activity in accordance with the present invention.

The replicate test and control samples can further comprise a cell that expresses a biologically active PZR polypeptide. The present invention also contemplates a recombinant cell line suitable for use in the exemplary method. A candidate substance identified according to the screening assay described herein is contemplated to have the ability to modulate PZR biological activity. Such as candidate compound has utility in the treatment of disorders and conditions associated with the biological activity of PZR.

Thus, a screening assay of the present invention also involves determining the ability of a candidate substance to modulate, i.e. inhibit or promote PZR biological activity in target cells. Target cells can be either naturally occurring cells known to contain a polypeptide of the present invention or transformed cells produced in accordance with a process of transformation set forth herein above. The test samples can further comprise a cell or cell line that expresses a PZR polypeptide; the present invention also contemplates a recombinant cell line suitable for use in the exemplary method. Such cell lines may be mammalian, or human, or they may from another organism, including but not limited to yeast. Exemplary assays including genetic screening assays and molecular biology screens such as a yeast two-hybrid screen that will effectively identify PZR-interacting genes important for potassium-chloride cotransport or other PZR-mediated cellular process. One version of the yeast two-hybrid system has been described (Chien et al, 1991, Proc. Natl. Acad. Sci. USA, 88:9578–9582) and is commercially available from Clontech (Palo Alto, Calfi.).

In a cell-free system, the method comprises: establishing a control system comprising PZR and a ligand wherein the PZR is capable of binding to the ligand; establishing a test system comprising the PZR, the ligand, and a candidate compound; measuring the binding affinity of the PZR and the ligand in the control and the test systems; and determining that the candidate compound modulates PZR activity in a cell-free system if the binding affinity measured for the test system is less than or greater than the binding affinity measured for the control system.

A screening assay of the present invention may also involve determining the ability of a candidate substance to modulate PZR biological activity and preferably, to thereby modulate the biological activity of SHP-2 in a target cell, such as the screening of candidate substances to identify those that modulate, i.e. inhibit or promote, PZR biological activity and thereby modulate the biological activity of SHP-2. Target cells can be either naturally occurring cells known to contain a polypeptide of the present invention or transformed cell produced in accordance with a process of transformation set forth herein before.

SHP-2 is a positive transducer of growth factor signal transduction. Thus, a candidate substance identified according to the screening assay described herein is contemplated to have the ability to modulate PZR biological activity and to thereby modulate the biological activity of SHP-2, and thus have utility in the treatment of disorders and conditions associated with the biological activity of SHP-2.

In another embodiment of the invention, a PZR polypeptide or catalytic or immunogenic fragment or oligopeptide thereof, can be used for screening libraries of compounds in any of a variety of drug screening techniques. The fragment employed in such screening may be free in solution, affixed to a solid support, borne on a cell surface, or located intracellularly. The formation of binding complexes, between the PZR polypeptide and the agent being tested, may be measured.

Another technique for drug screening which may be used provides for high throughput screening of compounds having suitable binding affinity to the protein of interest as described in published PCT application WO 84/03564, herein incorporated by reference. In this method, as applied to the PZR polypeptide, large numbers of different small test compounds are synthesized on a solid substrate, such as plastic pins or some other surface. The test compounds are reacted with the PZR polypeptide, or fragments thereof, and washed. Bound PZR polypeptide is then detected by methods well known in the art. Purified PZR polypeptide can also be coated directly onto plates for use in the aforementioned drug screening techniques. Alternatively, non-neutralizing antibodies can be used to capture the peptide and immobilize it on a solid support.

E.2. Screening for Phosphatase or Kinase Activity

PZR can serve as a standard in a screening assay for protein tyrosine phosphatase (PTP) and/or protein tyrosine kinase (PTK) activity in accordance with the present invention. A PTP is an enzyme which functions to remove a phosphate moiety from a biology molecule while a PTK is an enzyme that facilitates the attachment of a phosphate moiety to a biological molecule. The attachment and removal of phosphate moieties is a common and important mechanism that regulates the activity of biological molecules in vivo. The PZR protein has been determined herein to be readily phosphorylated and therefore can be used as a standard or control in an assay to determine the activity of a particular PTP or PTK.

A screening assay for compounds that modulate tyrosine kinase or phosphotyrosine phosphatase activities involved in signal transduction is also contemplated in accordance with the present invention. Cell-based and cell-free systems are contemplated. The assay includes contacting a cell lysate of a target cell that has been exposed to a test substance with an anchoring molecule that is specific for a protein substrate which has been dephosphorylated as a result of signal transduction in the target cell. Then, phosphotyrosine residues are detected on the protein substrate that is bound to the anchoring molecule.

Differences in the detection of phosphotyrosine residues on the immobilized protein substrate derived from the target cell lysate as compared to an immobilized protein substrate derived from a control target cell indicate that the test substance modulates the activity of the tyrosine phosphotase or tyrosine kinase. Examples of the anchoring molecules include both monoclonal and polyclonal antibodies, as can be prepared in accordance with methods described herein. An examples of the protein substrate comprises PZR. An example of a phosphatase comprises SHP-2. See also PCT Publication No. WO 96/40276, the contents of which are herein incorporated by reference.

In another aspect of the present invention, methods are provided for determining the presence or amount of a protein tyrosine phosphatase or for determining the presence or amount of a protein tyrosine kinase. In one embodiment, the method comprises: (a) incubating a sample suspected of containing a protein tyrosine phosphatase with a phosphorylated PZR peptide as set forth herein under conditions and for a time sufficient to permit dephosphorylation of the phosphorylated PZR peptide by a protein tyrosine phosphatase in the sample, wherein the phosphorus atom of the phosphorylated PZR peptide is radioactive; (b) separating non-dephosphorylated PZR peptide from free radioactive phosphorus released by dephosphorylation of the phosphorylated PZR peptide; and (c) detecting the presence or amount of radioactivity released by dephosphorylation of the phosphorylated PZR peptide, and therefrom determining the presence or amount of protein tyrosine phosphatase enzymatic activity in the sample. A embodiment having analogous steps and pertaining the determination of the presence or amount of protein tyrosine kinase enzymatic activity in a sample is also contemplated in accordance with the present invention.

E.3. Screening Conditions and Materials

As is well known in the art, a screening assay provides a cell under conditions suitable for testing the modulation of PZR biological activity or for PTP/PTK activity. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of PZR and SHP-2 modulation in specific cells. Such factors include, for example, the presence and absence (withdrawal) of growth factor, interleukins, or colony stimulating factors. U.S. Pat. Nos. 5,645,999; 5,786,152; 5,739,278; and 5,352,660 also describe exemplary screening assays, and the entire contents of each are herein incorporated by reference.

Representative candidate compounds for use in the foregoing screening assays are described in U.S. Pat. Nos. 5,580,979; 5,589,375; 5,624,816; 5,693,488; 5,723,593; 5,753,687; and 5,776,902, the entire contents of each are herein incorporated by reference. Other exemplary candidate compounds would be apparent to one having ordinary skill in the art after review of the disclosure of the present invention presented herein.

F. THERAPEUTIC METHODS

As used herein, the terms "PZR activity" and "PZR biological activity" are meant to be synonymous and are meant to refer to any biological activity of any PZR disclosed herein. Exemplary biological activities of PZR comprise SHP-2 binding activity, cell signaling activity or other biological activity in accordance with the present invention. Cell signaling activity can be further characterized as activity in mediating cell migration, cell aggregation and/or cell proliferation, and in modulation of density induced growth arrest, as disclosed in the Examples.

The biological activity can be accomplished by endogenous PZR or by PZR administered to a subject. Indeed, an isolated and purified PZR, recombinant PZR, and/or PZR analog or peptidomimetic, each prepared as described above, can administered to a subject to impart PZR biological activity in the subject and to treat a disorder associated with PZR biological activity in the subject. In such case the imparted PZR biological activity comprises a PZR biological activity in accordance with the therapeutic methods of the present invention.

The terms "PZR activity" and "PZR biological activity" are thus also meant to refer to activities mediated by the interactions of PZR with SHP-2 as described herein. Such interactions include PZR interactions with SHP-2 as described in the Examples below. Exemplary activities include, but are not limited to, modulating SHP-2 activity.

F.1. Modulation of PZR Biological Activity

In view of the foregoing, a therapeutic method is contemplated according to the present invention. The therapeutic method comprises administering to a subject a substance that inhibits or promotes PZR biological activity to thereby inhibit or promote the activity of PZR. Such a substance may be identified according to the screening assay set forth above. The method can comprise treating a subject suffering from a disorder having symptoms or characteristics that can be mediated through a PZR biological activity by administering to the subject an effective PZR modulating amount of a substance identified according to the screening assay described above and according to assays employed in the Examples below. By the term "modulating", it is contemplated that the substance can either promote or inhibit the activity of PZR, depending on the disorder to be treated. A particular disorder is characterized by undesirable cell migration and proliferation, i.e. cancers and angiogenesis, such as angiogenesis associated with metastasis of cancer. By promoting PZR biological activity in cancer therapy, restoration of contact inhibition of cell proliferation is contemplated, among therapeutic effects.

With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term "patient" is contemplated to include both human and animal patients. Thus, veterinary therapeutic uses are contemplated in accordance with the present invention.

Contemplated is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also contemplated is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine, ruminants, ungulates, horses, poultry, and the like.

SHP-2 is a positive transducer of growth factor signal transduction. Thus, a therapeutic method according to the present invention may also comprise administering a therapeutic composition which comprises a biologically active PZR of the present invention in amount effective to modulate the biological activity of SHP-2 in a subject.

F.1.1. Modulators of PZR Expression

A therapeutic method according to the present invention can comprise promoting or inhibiting PZR biological activity in a vertebrate subject by administering an effective amount of a substance that inhibits or promotes expression of a PZR-encoding nucleic acid segment in the vertebrate. Examples of such a substance, include, for example, an antisense oligonucleotide derived from any of SEQ ID NOs:1, 3, 5, 7, 17, 19, 21, 23, 25, 27, 29, 31, 33, 35, 37, 39, 41, 43, 45 and 47. Therapeutic methods utilizing antisense oligonucleotides have been described in the art, for example in U.S. Pat. Nos. 5,627,158 and 5,734,033, the contents of each of which are herein incorporated by reference.

F.1.2. Modulators of PZR Biological Activity

Insofar as a PZR modulator can take the form of a PZR ligand or ligand mimetic, and an anti-PZR monoclonal antibody, or fragment thereof, it is to be appreciated that the potency, and therefore an expression of a "therapeutically effective" amount can vary. However, as shown by the present assay methods, one skilled in the art can readily assess the potency of a candidate PZR modulator of this invention. A PZR modulator can be measured by a variety of techniques including through the use of a responsive reporter, which drives expression of a reporter gene; interaction of PZR with SHP-2, and/or other endogenous ligand, or monoclonal antibody to a PZR as described herein; and the like assays.

A preferred PZR modulator has the ability to substantially interact with PZR in solution at modulator concentrations of less than one (1) micro molar ($\mu$M), preferably less than 0.1 $\mu$M, and more preferably less than 0.01 $\mu$M. By "substantially" is meant that at least a 50 percent reduction in PZR biological activity is observed by modulation in the presence of the PZR modulator, and at 50% reduction is referred to herein as an IC50 value.

A therapeutically effective amount of a PZR modulator of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml.

A therapeutically effective amount of a PZR modulator of this invention in the form of a polypeptide is typically an amount of polypeptide such that when administered in a physiologically tolerable composition is sufficient to achieve a plasma concentration of from about 0.001 microgram ($\mu$g) per milliliter (ml) to about 10 $\mu$g/ml, preferably from about 0.05 $\mu$g/ml to about 1.0 ug/ml.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery techniques are contemplated where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic techniques.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

F.1.2.1. Polypeptides

In one embodiment, the invention contemplates PZR modulators in the form of polypeptides. A polypeptide (peptide) PZR modulator can have the sequence characteristics of either an endogenous ligand of the PZR or PZR itself at the region involved in PZR-ligand interaction. A preferred PZR modulator peptide corresponds in sequence to an endogenous ligand of PZR, such as SHP-2. A soluble or secreted or truncated form of the PZR polypeptide itself is also contemplated for use a PZR biological activity modulator, either to bind membrane-bound PZR in vivo or to bind PZR ligands in vivo to thereby modulate PZR biological activity.

Because PZR is a transmembrane protein, the present invention contemplates the use of an isolated and purified PZR ectodomain, or extracellular domain, which is described in the Examples below and in the Figures, in the described methods as modulator for PZR activity. Such use reflects the contemplation that the PZR ectodomain is a homophilic, or "self" ligand, as discussed in the Examples below.

The term "PZR ectodomain" is contemplated to refer to PZR ectodomain fusion proteins and polypeptides, recombinant PZR ectodomain proteins and polypeptides, peptide derivatives, amides, conjugates with proteins, cyclized peptides, polymerized peptides, analogs, fragments, chemically modified peptides, and the like derivatives, as described below. Representative embodiments of a "PZR ectodomain" in accordance with the present invention concern a protein or peptide that includes within its amino acid sequence an amino acid sequence essentially as set forth in amino acids 1–159 of any of SEQ ID NOs:2, 4, 6, 8, 18, 20, 22, 24, 26, 28, 30, 32, 34, 36, 38, 40, 42, 44, 46 and 48.

The term "a sequence essentially as set forth in amino acids 1–159 of any of SEQ ID NOs:2, 4, 6, 8, 18, 20, 22, 24, 26, 28, 30, 32, 34, 36, 38, 40, 42, 44, 46 and 48" means that the sequence substantially corresponds to a portion of amino acids 1–159 of any of SEQ ID NOs:2, 4, 6, 8, 18, 20, 22, 24, 26, 28, 30, 32, 34, 36, 38, 40, 42, 44, 46 and 48 and has relatively few amino acids which are not identical to, or a biologically functional equivalent of, the amino acids of amino acids 1–159 of any of SEQ ID NOs:2, 4, 6, 8, 18, 20, 22, 24, 26, 28, 30, 32, 34, 36, 38, 40, 42, 44, 46 and 48. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of amino acids 1–159 of any of SEQ ID NOs:2, 4, 6, 8, 18, 20, 22, 24, 26, 28, 30, 32, 34, 36, 38, 40, 42, 44, 46 and 48, will be sequences which are "essentially as set forth in amino acids 1–159 of any of SEQ ID NOs:2, 4, 6, 8, 18, 20, 22, 24, 26, 28, 30, 32, 34, 36, 38, 40, 42, 44, 46 and 48".

In one embodiment, a polypeptide of the present invention comprises no more than about 100 amino acid residues, preferably no more than about 60 residues, more preferably no more than about 30 residues. Peptides can be linear or cyclic.

It should be understood that a subject polypeptide need not be identical to the amino acid residue sequence of an endogenous ligand of PZR, such as SHP-2, so long as it includes required binding sequences and is able to function as a PZR modulator in an assay such as is described herein.

A subject polypeptide includes any analog, fragment or chemical derivative of a polypeptide which is a PZR modulator. Such a polypeptide can be subject to various changes, substitutions, insertions, and deletions where such changes provide for certain advantages in its use. In this regard, a PZR modulator polypeptide of this invention corresponds to, rather than is identical to, the sequence of the endogenous ligand where one or more changes are made and it retains the ability to function as a PZR modulator in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of an endogenous ligand of PZR in which one or more residues have been conservatively substituted with a functionally similar residue and which displays the PZR modulator activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. Such substitutions are described in detail above with respect to the isolated and purified PZR of the present invention.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a PZR endogenous ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues, but do not form PZR ligand epitopes. Typical amino acid residues used for linking are tyrosine, cysteine, lysine, glutamic and aspartic acid, or the like. In addition, a subject polypeptide can differ, unless otherwise specified, from the natural sequence of a PZR ligand by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol*, 32:221–96,1969; Fields et al., Int. *J. Peptide Protein Res.*, 35:161–214,1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable forforming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

F.1.2.2. Monoclonal Antibodies

The present invention describes, in one embodiment, PZR modulators in the form of monoclonal antibodies which immunoreact with a PZR and bind the PZR to modulate receptor activity as described herein. The invention also describes above cell lines which produce the antibodies, methods for producing the cell lines, and methods for producing the monoclonal antibodies.

A monoclonal antibody of this invention comprises antibody molecules that 1) immunoreact with isolated PZR, and 2) bind to the PZR to modulate its biological function.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments. Indeed, it is contemplated to be within the scope of the present invention that a monovalent modulator may optionally be is used in the present method. Thus, the terms "modulate", "modulating", and "modulator" are meant to be construed to encompass such fragments.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of this invention that is humanized by grafting to introduce components of the human immune system without substantially interfering with the ability of the antibody to bind antigen.

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

F.1.2.3. Other Modulators

Given the disclosure of the PZR activity in tissues herein, it is also contemplated that as yet undefined chemical compounds may be used to modulate PZR activity in tissues in accordance with the methods of the present invention. The identification of such compounds is facilitated by the description of screening assays directed to PZR activity in tissues presented above.

F.2. Gene Therapy

Mutation of myelin P0 has been shown to be responsible for the type 1B Charcot-Marie-Tooth disease. PZR shares a high sequence identity with myelin P0, thus suggesting pathological implications. In this regard, the PZR gene can be used for gene therapy in accordance with the present invention. Exemplary gene therapy methods, including liposomal transfection of nucleic acids into host cells, are described in U.S. Pat. Nos. 5,279,833; 5,286,634; 5,399,346, 5,651,964; 5,641,484; and 5,643,567, the contents of each of which are herein incorporated by reference.

Briefly, gene therapy directed toward modulation of PZR levels, to thereby affect or modulate the biological activity of PZR in a target cell is described. This modulation can affect cell signaling to thereby affect cell migration, cell aggregation, and/or cell proliferation. In one embodiment, a therapeutic method of the present invention contemplates a process for modulation of PZR levels comprising: (a) delivering to the cell an effective amount of a DNA molecule comprising a polynucleotide that encodes a biologically active PZR polypeptide; and (b) maintaining the cell under conditions sufficient for expression of the polypeptide.

In a preferred embodiment, the delivered polypeptide comprises an amino acid sequence or is encoded by a nucleic acid molecule comprising the sequence of any of SEQ ID NOs:1–8 and 17–48. Delivery may be accomplished by injecting the DNA molecule into the cell. Where the cell is in a subject, administering comprises: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a lymphocyte or a tumor cell from the tumor being treated. Techniques for transforming or transfecting a cell with a DNA molecule of the present invention are set forth above.

Alternatively, the vehicle is a virus or an antibody that specifically infects or immunoreacts with an antigen of the target tissue or tumor. An advantage of a viral infection system is that it allows for a very high level of infection into the appropriate recipient cell. Also, antibodies have been used to target and deliver DNA molecules.

It is also envisioned that this embodiment of the present invention can be practiced using alternative viral or phage vectors, including retroviral vectors, adenoviral and vaccinia viruses whose genome has been manipulated in alternative ways so as to render the virus non-pathogenic. Methods for creating such a viral mutation are set forth in detail in U.S. Pat. No. 4,769,331, incorporated herein by reference.

F.3. Dosages

For the purposes described above and in addition to the dosage information provided above, the identified substances may normally be administered systemically or partially, usually by oral or parenteral administration. The doses to be administered are determined depending upon age, body weight, symptom, the desired therapeutic effect, the route of administration, and the duration of the treatment etc. In a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there may be a case in which doses are lower than or greater than the ranges specified above.

As used herein, an "effective" dose refers to one that is administered in doses tailored to each individual subject in which modulation of PZR biological activity is desired sufficient to cause the modulation. After review of the disclosure herein of the present invention, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds may be administered to patients having reduced symptoms or even administered to patients as a preventative measure. Hence, the composition may be effective in therapeutic treatment even in the absence of symptoms of the disorder. Further, it will be appreciated by one of ordinary skill in the art after receiving the disclosure of the present invention that it may be necessary to make routine adjustments or variations to the dosage depending on the combination of agents employed, on the age and weight of the patient, and on the severity of the condition to be treated. Such adjustments or variations, as well as evaluation of when and how to make such adjustments or variations, are well known to those of ordinary skill in the art of medicine.

F.3.1. Gene Therapy Vector Construct Dosing.

Maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgias) and local (infections, pain) toxicities induced by the vector. A secondary endpoint is the clinical efficacy of the vector construct.

For example, a 4 ml serum-free volume of viral (e.g. adenoviral, retroviral, etc.) vector construct (containing up to $5 \times 10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4 day period of vector construct injection. Toxicity grading is done using the ECOG Common Toxicity Criteria. CBC, SMA-20, urinalysis, and conventional studies are performed daily during this period.

F.3.2. Dose escalation and MTD.

Patients are treated with $3 \times 10^6$ viral particles×4. Once they have all recovered from all grade 2 or less toxicities (except alopecia), and as long as grade 3–4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4) level 4, $5 \times 10^7$. Patients with measurable disease are evaluated for a clinical response to vector construct. Histology and local symptoms are followed.

F.4. Formulation of Therapeutic Compositions

The PZR modulating substance, the substance that inhibits or promotes expression of a PZR-encoding nucleic acid segment, and/or chosen gene therapy vectors are thus adapted for administration as a pharmaceutical composition. Formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

In a preferred embodiment, the present invention provides pharmaceutical compositions comprising a polypeptide or polynucleotide of the present invention and a physiologically acceptable carrier. More preferably, a pharmaceutical composition comprises a PZR polypeptide or a polynucleotide that encodes those polypeptides.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred technique for purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intra-vascularly).

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents: e.g. lubricating agents (magnesium stearate, etc.), disintegrating agents (cellulose, calcium glycolate etc.), and assisting agent for dissolving (glutamic acid, aspartic acid, etc.) stabilizing agent (lactose etc.). The tablets or pills may, if desired, be coated with gastric or enteric material (sugar, gelatin, hydroxypropylcellulose or hydroxypropylmethyl cellulose phthalate, etc.). Capsules include softones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions may also comprise adjuvants (wetting agents, suspending agents, etc.), sweetening agents, flavoring agents, perfuming agents and preserving agents.

Other compositions for oral administration include spray compositions which may be prepared by known methods and which comprise one or more of the active substance(s). Spray compositions may comprise additional substances other than inert diluents: e.g. preserving agents (sodium sulfite, etc.), isotonic buffer (sodium chloride, sodium citrate, citric acid, etc.). For preparation of such spray compositions, for example, the method described in U.S. Pat. Nos. 2,868,691 or 3,095,355 may be used.

Injections for parenteral administration include sterile aqueous or non-aqueous solution, suspensions and emulsions. In such compositions, one or more of active substance (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOLBATE 80® etc.). Injections may comprise additional other than inert diluents: e.g. preserving agents, wetting agents, emulsifying agents, dispersing agents, stabilizing agents (lactose, etc.), assisting agents such as for dissolving (glutamic acid, aspartic acid, etc.). They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for administration include liquids for external use, and endermic linaments (ointment, etc.), suppositories and pessaries which comprise one or more of the active substance(s) and may be prepared by known methods.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Materials Used in Examples

Polyclonal anti-SHP-1 and anti-SHP-2 antibodies were raised in rabbits against full length SHP-1 and SH2 domain-truncated form of SHP-2, respectively (Zhao, Z., et al. (1994) *J. Biol. Chem.* 269:8780–8785; Zhao, Z., et al. (1993) *J. Biol. Chem.* 268:2816–2820). An anti-SHP-2 antibody column was made by immobilization of affinity purified anti-SHP-2 antibody via $NH_2$—groups to CNBr-activated Sepharose resins (Sigma Chemical Co., St. Louis, Mo.). Monoclonal anti-phosphotyrosine 4G10 was purchased from Upstate Biotechnology Inc, Lake Placid, N.Y. Endoglysosidase F-N-Glycosidase F was from Sigma Chemical Co., St. Louis, Mo. The stably transfected 293 cells overexpressing the catalytic inactive mutant of SHP-1 or SHP-2 were obtained as described by Zhao, Z., et al. (1995) *J. Biol. Chem.* 270:11765–17769; Su, L., et al. (1996) *J. Biol. Chem.* 271:10385–10390. Pervanadate was made by mixing equal moles of sodium vanadate and $H_2O_2$ and incubating at room temperature for 20 min before addition to the cells (Zhao, Z., et al. (1996) *J. Biol. Chem.* 271:22251–22255).

Example 1

Isolation and Purification of PZR

Purification of PZR from 293 cells overexpressing the catalytically inactive mutant of SHP-2. The stably transfected 293 cells overexpressing the catalytic inactive mutant of SHP-2 were grown in DMEM/High containing 10% calf serum and 100 unit/ml each of penicillin and streptomycin and 0.25 mg/ml G418 sulfate. After growing to confluency, the cells were treated with 0.1 mM pervanadate for 20 min before harvesting in ice-cold phosphate-buffered saline. The collected cells were broken up with a Dounce glass homogenizer in Buffer A containing 25 mM β-glycerophosphate (pH 7.3), 10 mM EDTA, 2 mM EDTA, 0.2 mM $Na_3VO_4$, 1 mM benzamidine, 0.1 mM phenylmethylsulfonyl fluoride, 2 μg/ml leupeptin, 1 μM pepstatin A, and 1 μg/ml aprotinin. Nuclear pellets were removed by centrifugation at 800×g for 20 min, and the remaining postnuclear extract was further centrifuged at 100,000×g for 45 min to give a clear cytosolic supernatant and a pelleted membrane fraction. The latter pellet, washed once with Buffer A and then dissolved in the same buffer supplemented with 1% Triton X-100, was referred to as the membrane extract.

After centrifugation at 10,000×g for 30 min, the clear membrane extract was loaded onto a fast flow Q-Sepharose column (Pharmacia, Piscataway, N.J.) equilibrated with Buffer B (25 mM (β-glycerolphosphate, pH 7.3, 1 mM EDTA, and 2 mM β-mercaptoethanol), and the flowthrough was loaded directly onto a fast flow SP-Sepharose column (Pharmacia, Piscataway, N.J.). The proteins were then eluted with Buffer B supplemented with 0.3 M NaCl. This was followed by separation of proteins on a wheat germ agglutinin column which was equilibrated with Buffer B and eluted with 0.3 M N-acetylglucosamine. The eluates were loaded onto an anti-SHP-2 antibody-Sepharose column which was equilibrated with Buffer B, washed with 0.5 M NaCl, and eluted with 2.0 M NaSCN. The final purification step was achieved by using a 7.5% preparative SDS gel (Bio-Rad, Hercules, Calif.). Throughout the purification procedure, the proteins were followed by anti-phosphotyrosine Western blot analyses.

Isolation and sequencing of peptides. The purified protein was digested with endoproteinase Lys-C. Resulting peptide fragments were isolated by reverse phase HPLC equipped with a C18 column. Several peptide peaks were chosen for peptide sequence analyses by using a gas phase sequenator at the Vanderbilt Cancer Center, Nashville, Tenn.

Molecular cloning of PZR. Peptide sequence analyses gave rise to four clean peptide sequences. Search of the Expressed Sequence Tags (EST) database of The Institute for Genomic Research with two of the peptide sequences pulled out an EST which potentially codes for part of a protein. PCR primers were thus designed to amplify the full length cDNA according to the rapid amplification of cDNA ends (RACE) strategy by using the Marathon cDNA Amplification Kit from Clontech (Palo Alto, Calif.).

One RACE primer (AP1) was provided in the kit. Two gene specific primers were designed according to the EST sequence. They were 5'-TCCGAGGAGCCTGCTTAACTGGTGAC-3' (SEQ ID NO:9) for 5' RACE and 5'-GTAGTGGTGGGCATAGTTACTGCTGT-3' (SEQ ID NO:10) for 3' RACE. The Advantage KlenTaq polymerase and the Advantage-GC cDNA polymerase, two Taq polymerase mixtures from Clontech, Palo Alto, Calif., were used for PCR amplification according to the manufacturer's protocol. The PCR products were cloned into the pCR2.1 TA cloning vector (Invitrogen, Carlsbad, Calif.) and were then sequenced. Combining of the 5' and 3' RACE products which had an overlapping sequence gave rise to a complete cDNA encoding a protein containing all the four peptides sequenced.

To isolate the full length coding region, two gene specific primers corresponding to the 5' and 3' coding regions of the cDNA were designed. They were 5'-GATGGCAGCGTCCGCCGGAGCCGG-3' (SEQ ID NO:11) and 5'-CCAGTTTGGTTTTGTTTCTTGCTGAGG-3'(SEQ ID NO:12). PCR was performed by using the high fidelity DNA polymerase Pfu and Turbo Pfu (Stratagene, La Jolla, Calif.) in addition to the Taq DNA polymerase mixes from Clontech as used above. HeLa cell and human kidney Marathon-ready cDNAs purchased from Clontech and 293 cell cDNAs prepared by using the RT-PCR amplification kit (Clontech, Palo Alto, Calif.) were used as templates. The PCR was run for 25 cycles at 94° C. for 1 min, 65° C. for 1 min, and 72° C. for 4 min. The products obtained with the Pfu enzymes were subcloned into the pBluescript KS vector (Stratagene, La Jolla, Calif.) which was opened by EcoR V digestion, while those obtained with the Taq polymerases were subcloned into pCR2.1 as described above. DNA sequencing was performed by using the automated DNA sequencer at the Vanderbilt Cancer Center, Nashville, Tenn.

Production of anti-PZR antibody. For antibody production, the intracellular portion (corresponding to amino acid residue 192–269) of PZR was expressed in *E. coli* as a glutathione-S-transferase fusion protein by using the pGex-2T vector (Pharmacia, Piscataway, N.J.) and purified by using a glutathione-Sepharose column. A rabbit was injected with the fusion protein to produce the anti-serum.

Overexpression of PZR in Jurkat cells. PZR cDNA encoding the entire coding sequence of the protein was constructed into the pCDNA3 vector (Invitrogen, Carlsbad, Calif.), and the cDNA plasmid was used to transfect Jurkat cells by electroporation. The cells were grown to ~2×10$^6$/ml in RPMI 1640 medium supplemented with 10% fetal calf serum and 50 μg/ml each of streptomycin and penicillin. Cells (1×10$^7$) were collected by centrifugation, washed with plain medium without serum, and then resuspended in 300 μl of the same plain medium. The cDNA plasmid (20 μg) in 100 μl water was added to the cells. The electroporation was performed under 950 μF, 250 Volts, and 72 Ohms with 4 mm cuvettes by using the ECM 600 electroporation system (BTX Inc., San Diego, Calif.). After sitting on ice for 15 min, the cells were transferred to 5 ml complete medium and continued in culture for 72 hr before further treatment.

Cell stimulation, immunoprecinitation and Western blotting analyses. To investigate tyrosine phosphorylation of PZR, Jurkat cells transiently overexpressing PZR and wild type 293 cells were treated with 100 mM pervanadate for 30 min. After washing with ice-cold phosphate-buffered saline, the cells were lysed in Buffer A supplemented with 1% Triton X-100. Extracts were cleared by centrifugation. For immunoprecipitation, cell extracts were incubated overnight with the anti-PZR antibodies pre-bound to protein A-Sepharose. The beads were washed three times with Buffer A supplemented with 0.3 M NaCl. For Western blot analyses, samples were separated by 10% SDS-PAGE and transferred to polyvinylidene difluoride membranes. The membranes were probed with various primary antibodies and were detected by using the ECL system with horseradish peroxidase-conjugated secondary antibodies (Amersham, Piscataway, N.J.).

Northern Blot Analysis. To determine the level of expression of PZR in various tissues, a Human Multiple Tissue Northern Blot system (Clontech, Palo Alto, Calif.) was employed as previously described by Ahmad, S., et al. (1993) *Proc. Natl. Acad. Sci. USA*. 90:2197–2201. This was performed according to the manufacturer's protocol. Briefly, the blot was pre-hybridized for 1 hr and then hybridized for 1 hr at 68° C. in the ExpressHyb® hybridization solution provided in the kit. The probe (PZR fragment) was labeled with [α-$^{32}$P]dCTP by using the T7 Quick Prime kit (Pharmacia, Piscataway, N.J.). The blot was washed three times with 2×SSC and 0.05% SDS at room temperature and three times with 0.1×SSC and 0.1% SDS at 50° C. before exposure to X-ray film at –80° C. Standard 1.35 to 9.5 RNA ladder markers were used as a reference.

Example 2

Evaluation of the Association of PZR with SHP-2 In Vivo

Identification and purification of a 43 kDa hyperphosphorylated protein.

All PTPs contain a highly conserved cysteinyl residue within their catalytic centers, which is directly involved in the formation of a thiophosphate intermediate essential for the catalysis (reviewed in Fischer, E. H., et al. (1991)

Science 253:401–6 and in Walton, K. M. and Dixon, J. E. (1993) Annu. Rev. Biochem. 62:101–20). Mutation of this cysteinyl residue to serine impairs the phosphatase activity. The Cys-to-Ser mutants of SHP-1 and SHP-2 display dominant negative effects and cause hyperphosphorylation of specific cellular proteins on tyrosine as previously described (Zhao, Z., et al. (1995) J. Biol. Chem. 270:11765–17769; Su, L., et al. (1996) J. Biol. Chem. 271:10385–10390.). In human embryonic kidney 293 cells, expression of the catalytically inactive Cys-to-Ser mutant form of SHP-2 resulted in tyrosine phosphorylation of 43 and 95 kDa proteins which were associated with SHP-2, while over-expression of the mutant of SHP-1 led to tyrosine phosphorylation of 95 and 110 kDa proteins which were associated with SHP-1. The immunoprecipitates were separated on SDS gels, transferred to PVDF membranes, and detected by anti-phosphotyrosine Western blotting. Positions of SHP-1, SHP-2, and the heavy chain of IgG were determined on the gels, and "p43", "p95", and "p110" were used to denote the 43, 95, 110 kDa tyrosine-phosphorylated proteins, respectively.

Tyrosine phosphorylation of these proteins and their association with SHP-1 and/or SHP-2 were also observed in cells (including 293 and HeLa cells) treated with pervanadate, a potent inhibitor of PTPs. Since hyperphosphorylation of these proteins correlated with the inactivation of SHP-1 and SHP-2, they are putative substrates of the enzymes. The selective interaction of the 43 kDa protein with SHP-2 suggests its specific role in cell signaling involving SHP-2. The 43 kDa protein was purified (referred to as p43 or PZR hereafter).

For purification of PZR, 293 cells expressing the catalytically inactive mutant of SHP-2 were treated with 0.1 mM pervanadate for 20 min to enhance tyrosine phosphorylation of the protein. After lysis of the cells in Buffer A, p43 was partitioned exclusively in the membrane extract. The protein did not bind to the anionic fast flow Q-Sepharose column, but this step was necessary for efficient separation of p43 on the next cationic fast flow SP-Sepharose column which was eluted with 0.3 M NaCl. In the following step, p43 bound to the wheat germ agglutinin column, and it was eluted with 0.3 M N-acetyl-glucosamine. This suggests that p43 is a glycoprotein. Because p43 and SHP-2 formed a tight complex, the anti-SHP-2-Sepharose column was able to pull down both proteins. The 95 kDa protein was also found in the complex, but it was less abundant. Following purification of the NaSCN eluate of the antibody column on a preparative SDS gel, ca. 50 µg purified p43 was obtained from 300 plates (150 mm) of transfected 293 cells.

On SDS gels, purified p43 ran as a broad band around 43 kDa, but upon deglycosylation by N-glycosidase F, it displayed a sharp band at ca. 30 kDa. For the gels, purified p43 (0.5 µg) was treated with 2 units of N-glycosidase F for 0, 10 and 40 minutes, respectively. Proteins were detected by Coomassie brilliant blue R-250 staining. This further confirms that p43 is a glycosylated protein and indicates that the glycosylation causes heterogenous migration of p43 on SDS gels.

To demonstrate specific dephosphorylation of p43 by SHP-2, purified p43 was incubated with equal units of SHP-1 or SHP-2 as follows: purified p43 (0.25 µg) was incubated with 0.1 unit of SHP-1 or SHP-2 for 10 min in a buffer containing 25 mM β-glycerolphosphate (pH 7.3), 1 mM EDTA, and 2 mM β-mercaptoethanol. SHP-2 caused complete dephosphorylation of p43 while SHP-1 only produced a partial dephosphorylation, indicating that p43 is a physiological substrate of SHP-2 in view of the specific dephosphorylation of p43 by SHP-2. Tyrosine phosphorylation was detected by Western blotting analyses with anti-phosphotyrosine. Activity of SHP-1 and SHP-2 was determined by using para-nitrophenylphosphate as a substrate as described by Zhao, Z., et al. (1994) J. Biol. Chem. 269:8780–8785; Zhao, Z., et al. (1993) J. Biol. Chem. 268:2816–2820.

Peptide mapping and amino acid analysis. For this purpose, the gel purified protein was digested with endoproteinase Lys-C. Upon separation of the peptides on a reverse phase C18 column, 28 peaks were obtained. Sequencing of peptides corresponding to four of the peaks gave rise to four clean peptide sequences. These, in single letter amino acid symbols, are peak 15, RDXTGCSTSESLSPVK (SEQ ID NO:13); peak 17, SLPSGSHQGPVI YAQLDHSG-GHHSDK (SEQ ID NO:14); peak 19, DRISWAGDLDK (SEQ ID NO:15); peak 26, NPPDIVVQPGHIRLYVVEK (SEQ ID NO:16). The letter X in the sequence of the peak 15 peptide corresponded to a cycle which gave no regular amino acid signal. Sequencing of peptides corresponding to several other peaks yielded mixed peptides. A search of the protein and nucleotide databases of the National Center for Biotechnology Information by using the BLAST program revealed that peptides corresponding to peaks 19 and 26 showed significant sequence homology to peptide segments of human peripheral myelin P0. A search of Expressed Sequence Tags (EST) database of The Institute for Genomic Research (TIGR) with peptide sequences from peak 15 and 17 pulled out an EST with an ID number of THC211134. The EST spans 2892 bp, and it has multiple ambiguous bases. When the EST sequence is inverted, its 5'-end potentially codes for part of a protein which contains the peptide sequences found in peak 15 and 17.

cDNA cloning of PZR. ESTs are partial, single-base sequences from either end of a cDNA clone. The EST strategy was developed to allow rapid identification of expressed genes by sequence analysis. Two specific PCR primers derived from the EST sequence were thus synthesized and used to amplify a RACE-ready HeLa cell cDNA library. The 3' RACE gave rise to a 521 bp PCR product with a poly-A tail. The non-poly A region essentially verified the EST sequence which had two uncertain bases in this region. The 5' RACE yielded a 784 bp PCR product with a GC rich 5'-region and an initial codon. Combining of the 3' and 5' RACE products which had an overlapping sequence resulted in a cDNA of 1151 bp. The cDNA contained a 807 bp open reading frame encoding a 269 aa protein which contained all the peptides sequenced. To clone the coding region of the cDNA, two specific PCR primers corresponding to the 5' and 3' coding regions were synthesized. For PCR amplification, three cDNA libraries were employed (from kidney, HeLa and 293 cells) along with four different thermo-DNA polymerases including two hot-start Taq polymerase mixtures (Clontech, Palo Alto, Calif.) and two high fidelity Pfu enzymes (Stratagene, La Jolla, Calif.). All gave rise to an identical PCR product matching that obtained from RACE. This not only confirmed the coding region but also essentially ruled out possible cloning artifacts caused by PCR.

DNA Sequence Analysis. The nucleotide sequence of PZR cDNA and the amino acid sequence deduced from it are presented in FIG. 1. The open reading frame consists of 807 nucleotides encoding a protein of 269 amino acids with a calculated molecular mass of 29,081 Da, which is very close to the size of the deglycosylated protein on SDS gel. The deduced amino acid sequence contains a signal sequence at the amino terminus, a membrane-spanning segment in the middle, and an 80 amino acid C-terminal intracellular portion. The primary structure predicts that PZR is a transmembrane protein, which is consistent with our previous observation that p43 co-localized with catalytically inactive SHP-2(C-S) on the plasma membrane (Zhao, Z., et al. (1995) *J. Biol. Chem.* 270:11765–17769). The 132 bp 5'-untranslated sequence has 75% G+C. There are a G at the +4 position and a purine A at the −3 position from the initiating ATG, that conforms with requirements for efficient translation as defined by Kozak (Kozak, M. (1989) *J. Cell. Biol.* 108, 229–241). The 3'-untranslated region stretches 184 bp before reaching the poly-A tail.

Sequence analysis revealed that the extracellular portion of PZR forms an immunoglobulin-like domain with two cysteinyl residues and two potential N-linked glycosylation sites. It shares 45.8% sequence identity and 60.2% sequence similarity with the extracellular domain of myelin P0 (FIG. 2A), a major structural protein of peripheral myelin which is mutated in type 1B Charcot-Marie-Tooth disease (Filbin, M. T. and Tennekoon, G. I. (1992) *Bioessays* 14:541–547; Harding, A. E. (1995) Brain 118:809–818). The intracellular segment of PZR displayed no significant sequence identity with any known protein except for two immunoreceptor tyrosine-based inhibitory motifs (ITIMs) which have a V/IXYXXL/V consensus sequence (FIG. 2B). The ITIM was initially defined in FCyRB (Muta, T., et al. (1994) *Nature* 368:70–73.), and later in many other hematopoietic cell proteins including KIR (Colonna, M. and Samaridis, J. (1995) *Science* 268:405–408.) and LAIR (Meyaard, L., et al. (1997) *Immunity* 7:283–290). Interestingly, this motif is also found in SIRP/SHPS-1, a putative SHP-2 substrate which has recently been cloned (Kharitonenkov, A., et al. (1997) *Nature* 386:181–186; Fujioka, Y., et al. (1996) *Mol. Cell. Biol.* 16:6887–6899). It should be noted that PZR shares no significant overall sequence identity with SIRP/SHPS-1.

The ITIMs corresponding to Y241 and Y263 of PZR resemble the consensus sequence for binding of SHP-2 SH2 domains, suggesting that Y241 and Y263 may provide docking sites for the enzyme. Y200 corresponded to a peptide sequencing cycle which gave no signal is probably fully phosphorylated in the purified protein. It has an acidic amino acid residue on the N-terminal side, conferring the consensus phosphorylation sequence for many tyrosine kinases. Since the SH2 domain of SHP-2 requires hydrophobic residues at the third position following the phosphotyrosine, for specific binding (Lee, C. H., et al. (1994) *Structure* 2:423–438), Y200 is unlikely to serve as a docking site for SHP-2. It may participate in interactions with other proteins and presumably act as a target of the catalytic domain of SHP-2. In this regard, PZR is a physiological substrate of SHP-2. Above all, the structural features of PZR make it an important player in cell signaling involving SHP-2.

Overexpression of PZR and its association with SHP-2. Western blot analyses with anti-PZR antibody showed that Jurkat cells express essentially no endogenous PZR. Transfection of the cells with PZR cDNA resulted in expression of PZR with the expected molecular size. On the Western blots, cell extracts (20 μg) from control and PZR construct-transfected cells were analyzed for PZR expression by using the anti-PZR antibody.

The association of PZR with SHP-2 was characterized on Western blots as follows. pCDNA3-PZR-transfected Jurkat cells and wild type 293 cells were either left untreated (referred to on the Western blots as "−" lanes) or were treated with 0.1 mM pervanadate (referred to on the Western blots as "+" lanes) for 30 min. Cells extracts were immunoprecipitated with anti-PZR or anti-SHP-2 antibodies, and the immunoprecipitates or the immuno-depleted supernatants were subjected to Western blot analyses with anti-phosphotyrosine, anti-SHP-2, and anti-PZR. Non-specific bands (NSB) which essentially reflect equal loading of samples were also noted on the Western blots.

The heterogeneous distribution of the protein on SDS gel can be attributed to the different degrees of glycosylation. To confirm the tyrosine phosphorylation of PZR and its association with SHP-2, the transfected cells were stimulated with pervanadate. PZR was heavily phosphorylated on tyrosine, and it formed a complex with SHP-2 which itself was phosphorylated on tyrosine. Similar results were observed in wild type 293 cells treated with pervanadate. In this case, in addition to SHP-2, a number of tyrosine-phosphorylated proteins with molecular sizes ranging from 80 to 180 kDa were also co-immunoprecipitated with PZR. In both Jurkat and 293 cells, co-immunoprecipitation of SHP-1 with PZR was not detected although both cell lines express a high level of SHP-1.

Cells have also been treated with epidermal growth factor (EGF), insulin, and platelet-derived growth factor (PDGF). However, none of these growth factors could induce tyrosine phosphorylation of PZR. This suggests that PZR is involved in different signaling systems. Particularly it was observed that EGF, PDGF, and insulin fail to stimulate tyrosine phosphorylation of PZR. Serum-starved HT-1080 fibrosarcoma cells were treated with 20 ng/ml EGF, 20 ng/ml PDGF, and 100 ng/ml insulin for 5 min or 0.1 mM pervanadate for 30 min. Whole cell extracts were immunoprecipitated with anti-PZR, and the immunoprecipitates were subjected to Western blot analyses with anti-phosphotyrosine and anti-PZR antibodies. Whole cell extracts were analyzed for activation of ERK1/2 by using a phospho-specific anti-ERK antibody.

Thus, EGF, PDGF and insulin failed to induce tyrosine phosphorylation of PZR while pervanadate caused a drastic phosphorylation. Equal immuno-precipitation of PZR from the cell extract was observed. Response of HT-1080 cells to the growth factors were evident in the activation of ERK1/2. The data indicate that EGF, PDGF, and insulin fail to induce tyrosine phosphorylation of PZR. Similar results were also observed with 293 cells.

To characterize further the association of PZR with SHP-2, immuno-depletion of PZR and SHP-2 was performed. Both proteins were totally depleted from cell extracts by correspondent antibodies. In the non-stimulated cells, depletion of one protein had no effect on the presence of the other protein in the cells extracts. In the pervanadate-treated cells, however, depletion of SHP-2 resulted in an over 90% loss of PZR in the extracts while depletion of PZR caused approximately 50% removal of SHP-2. These data not only reveal a near stoichiometric association of PZR with SHP-2 but also indicate that PZR may be a major anchor of SHP-2 on the plasma membrane.

Northern blot analyses of PZR expression in human tissues. Northern analyses (each lane of the gels used to prepared Northern blots contained) 2 μg of poly(A)+RNA) showed that PZR is expressed in all human tissues investigated (i.e., heart, brain, placenta, lung, liver, skeletal muscle, kidney and pancreas). Expression in heart, placenta, kidney, and pancreas appeared to be particular high. The size of the major transcript from the PZR gene is approximately 4.0 kb. Two minor forms of 3.8, and 1.3 kb were also seen. The cDNA obtained from RACE may correspond to the 1.3 kb transcript, which happened to be predominantly amplified in the PCR reaction due to its short length. The 4.0 and 3.8 kb transcripts can result from alternate splicing or extended 3' non-coding region. In fact, the EST sequence pulled out from the database spanned 2580 bp after the termination codon.

Discussion of Examples 1 and 2

The present study reports purification, molecular cloning, and preliminary characterization of PZR, a binding protein and putative physiological substrate of SHP-2. PZR is a novel member of the immunoglobulin super-family. Its extracellular segment has significant sequence homology to myelin P0 while its intracellular portion has two tyrosine phosphorylation sites resembling ITIMs. Myelin P0 is a major transmembrane glycoprotein in the myelin sheath, and it has strong pathologic implications. It has been shown that mutation of myelin P0 is responsible for type 1B Charcot-Marie-Tooth disease and homophilic interaction between P0 molecules mediates the apposition of two neighboring membrane layers of myelin. With 60% sequence similarity to myelin P0, it is comtemplated that PZR plays a similar role in mediating cell-cell interactions in a variety of cells.

The ITIM was initially identified in several inhibitory immunoglobulin superfamily members, including human KIR, FcyRII, LAIR, gp49, gp91 (Muta, T., et al. (1994) Nature 368:70–73; Colonna, M. and Samaridis, J. (1995) Science 268:405–408; Meyaard, L., et al. (1997) Immunity 7:283–290). In contrast to the immunoreceptortyrosine-based activation motifs (ITAMs) found in proteins associated with cell-surface immunoglobulin receptors, T-cell antigen receptors, and certain Fc receptors, ITIMs play an important role in signal inhibition by recruiting terminating enzymes including protein tyrosine phosphatases SHP-1 and SHP-2 and inositol phosphatase SHIP (Unkeless, J. C. and Jin, J. (1997) Curr. Opinion in Immunol. 9:338–343; Vely, F., et al. (1997) Eur. J. Immunol. 27, 1994–2000; Vely, F. and Vivier, E. (1997) J. Immunol. 159:2075–2077; Isakov, N. (1997) Immunol. Res. 16:85–100). The presence of ITIMs in PZR, which is widely distributed in non-hematopoietic cells, suggests an importance of these motifs.

SIRP/SHPS-1, a putative SHP-2 substrate which also contains ITIMS, has been shown to inhibit signaling through tyrosine kinase receptors (Kharitonenkov, A., et al. (1997) Nature 386:181–186). This inhibitory effect is presumably mediated by ITIMs which may serve as binding sites for SHP-2. Finally, since PZR specifically interacts with SHP-2 and not SHP-1, it may be responsible for the distinctly different functions of these two enzymes in cell signaling. Considering the crucial role of SHP-2 in cell signaling, as a binding protein and putative physiological substrate, PZR is an important signaling molecule.

Example 3

Expression of a Soluble PZR Polypeptide

The expression of a soluble form of PZR was performed in 293 cells. The cDNA encoding the signal sequence and the extracellular portion of PZR was cloned into the pCDNA3 vector, and the DNA construct was used to transfect 293 cells. The culture medium was analyzed for expression of soluble PZR by using Western blotting with an anti-PZR antibody. Three forms of soluble PZR representing different degrees of glycosylation were seen at 14.4, 21.5 and 29 kDa, respectively. Representative amino acid and nucleic acid sequences for soluble PZR are set forth in SEQ ID NOs:33–40.

Example 4

Alternately Spliced Human PZR

SEQ ID NOs:17–24 set forth DNA and amino acid sequence data for human PZR 1b (hPZR1b). hPZR1b lacks the intracellular ITIMs of PZR. It was isolated from human Jurkat cell cDNA library in accordance with techniques disclosed herein. It represents an alternately spliced form of PZR.

Example 5

Association of PZR with SHP-2 in Various Tissues

One hour after intravenous injection of pervanadate into mice, various tissues of the mice were extracted. The tissues included bone marrow, brain, heart, intestine, kidney, liver, lung, muscle, spleen and peripheral blood. Cell extracts were immunoprecipitated with anti-SHP-1 or anti-SHP-2 antibodies, and the immunoprecipitates were subjected to Western blot analyses with anti-phosphotyrosine. PZR was observed in brain, heart, intestine, kidney, lung, muscle and spleen, and the position of PZR was determined to be about 43 kDa.

SEQ ID NOs:25–32 set forth DNA and amino acid sequence data for mouse PZR (mPZR). FIG. 3 depicts amino acid sequence alignment between mouse PZR (SEQ ID NO:26) and human PZR (SEQ ID NO:2).

Examples 6–9

Analysis of the Interaction of SHP-2 with PZR

In Examples 6–9 it is observed that the tyrosine 241 and 263 embedded in the consensus immunoreceptor tyrosine-based inhibitory motifs (ITIMs—each shown in bold in FIG. 1) VIYAQL (amino acids 239–246 of SEQ ID NO:2) and VVYADI (amino acids 261–268 of SEQ ID NO:2), respectively, of PZR accounts for the entire tyrosine phosphorylation of PZR. The interaction between PZR and SHP-2 requires involvement of both tyrosyl residues of the former and both SH2 domains of the latter since its was disrupted by mutating a single tyrosyl residue or an SH2 domain. Overexpression of catalytically inactive but not active forms of SHP-2 bearing intact SH2 domains in cells caused hyperphosphorylation of PZR. In vitro, tyrosine phosphorylated PZR was efficiently dephosphorylated by the full-length form of SHP-2 but not by its SH2 domain-truncated form. Together, the data indicate that PZR serves not only as a specific anchor protein of SHP-2 on the plasma membrane but also as a physiological substrate of the enzyme. The coexisting binding and dephosphorylation of PZR by SHP-2 may function to terminate signal transduction initiated by PZR and SHP-2, and to set a threshold for the signal transduction to be initiated.

Materials and Methods for Examples 6–9

Figure 5:
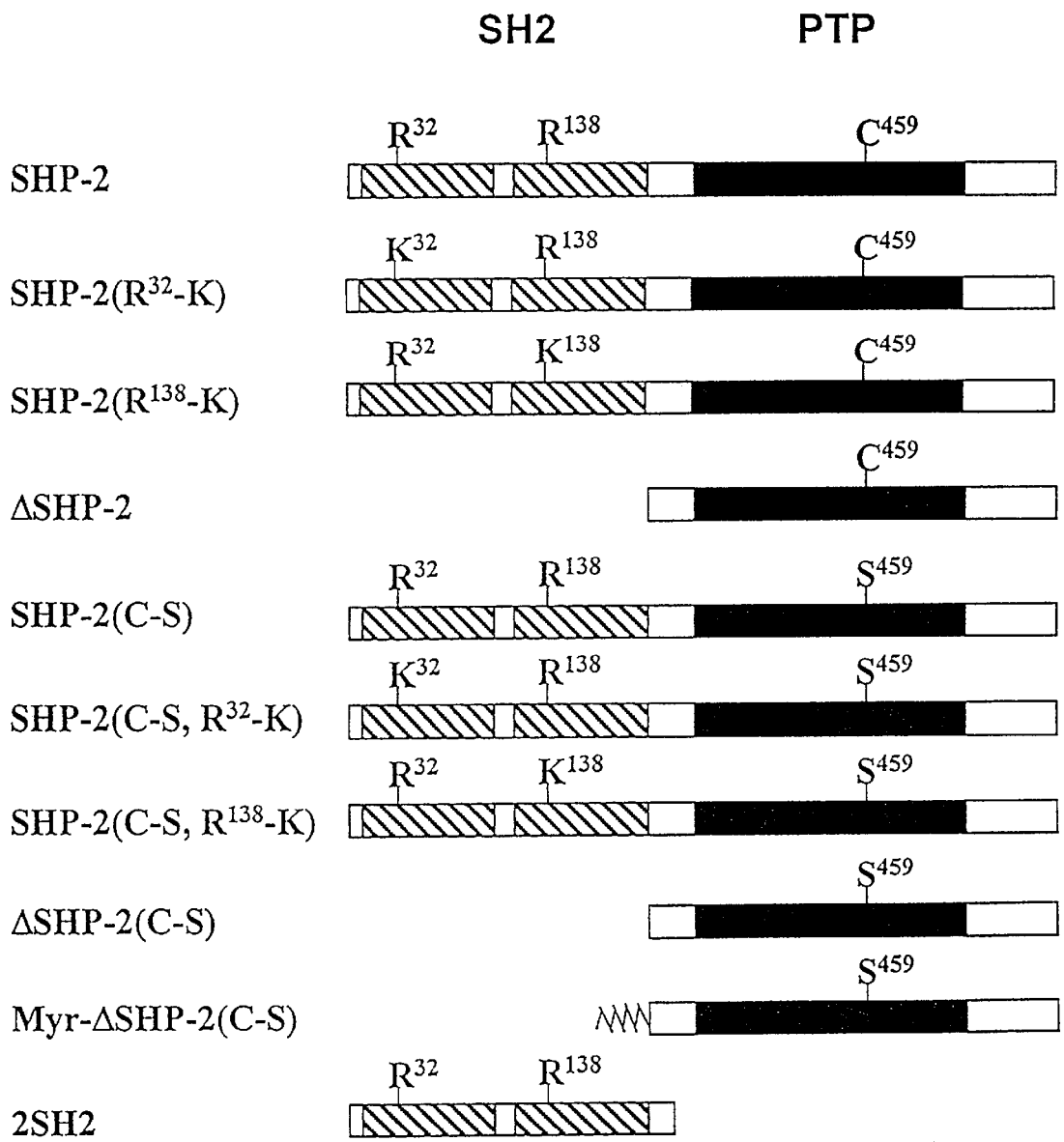
FIG. 5 is a schematic diagram of SHP-2 constructs. Amino acid symbols: R, arginine; K, lysine; C, cysteine; S, serine. Myr represents consensus myristoylation sequence MGSNKSKPKDASQRR (SEQ ID NO:49).

Cells and Antibodies. Jurkat and 293 cells were obtained from the American Type Culture Collection. Polyclonal anti-SHP-2 serum 1263 and anti-PZR serum 105 were raised in rabbits against SH2 domain-truncated form of SHP-2 and GST fusion protein of the intracellular domain of PZR, respectively, as described above. Monoclonal anti-phosphotyrosine 4G10 was purchased from Upstate Biotechnology Inc., Lake Placid, N.Y. Pervanadate was made by mixing equal moles of sodium vanadate and $H_2O_2$ and incubating at room temperature for 20 min before adding to cells (Zhao, Z., et al. (1996) J. Biol. Chem. 271, 22251–22255).

cDNA constructs of PZR and SHP-2. FIGS. 4 and 5 list the cDNA constructs of PZR and SHP-2 used in Examples 6–9, respectively. The PZR constructs were made with the pCDNA3 vector, and the SHP-2 constructs were built with the pRC/CMV vector, an earlier version of the pCDNA3 vector. Both expression vectors contain the CMV promoter for high expression in mammalian cells and the neomycin resistance gene (neo) for selection with G418 sulfate. Construction of PZR, SHP-2, and catalytically inactive Cys-to-Ser mutant SHP-2 (C-S) are described above. Mutation of Tyr to Phe in PZR and Arg to Lys and Cys to Ser in SHP-2 were carried out by polymerase chain reaction, and the mutageneses were confirmed by DNA sequencing.

ΔSHP-2 represents SH2 domain-truncated form of SHP-2 and corresponds to amino acid residues 200–593 while 2SH2, the PTP domain-truncated protein, contains amino acid residues 1–210. Both were made by truncation of cDNA at convenient restriction sites and re-legating with appropriate linkers with an initiation codon or termination codon as required. Myr-ΔSHP-2, which has a myristoylation tag for membrane targeting was made by adding a consensus myristoylation sequence corresponding to the 15 N-terminal amino acid residues, MGSNKSKPKDASQRR (SEQ ID NO:49), of human c-Src. Tanaka, A., et al. (1987) *Mol. Cell. Biol.* 7:1878–1983; Zhao, R. and Zhao, Z. J. (1999) *Biochem. J.* 338:35–39.

Transient expression of PZR in Jurkat cells and SHP-2 in 293 cells. Transfection of Jurkat cells with various forms of PZR constructs was performed by electroporation as described above. The cells were grown to ~2 ×10$^6$/ml in RPMI 1640 medium supplemented with 10% fetal calf serum and 50 μg/ml each of streptomycin and penicillin. Cells (1×10$^7$) were collected by centrifugation, washed with plain medium without serum, and then resuspended in 300 μl of the same plain medium. The cDNA plasmid (20 μg) in 100 μl water was added to the cells. The electroporation was performed under 950 μF, 250 Volts, and 72 Ohms with 4 mm-cuvettes by using the ECM 600 electroporation system (BTX Inc., San Diego, Calif.).

After sitting on ice for 15 min, the cells were transferred to 5 ml of complete medium and continued in culture for 72 hr before further treatment. Transfection of 293 cells was carried out according to a calcium phosphate co-precipitation protocol (Chen, C. and Okayama, H. (1987) *Mol. Cell. Biol.* 7:2745–2752). Briefly, 293 cells were grown to confluency in DMEM medium supplemented with 10% fetal calf serum and 50 μg/ml each of streptomycin and penicillin and then were split 1-to-8 and cultured overnight to ca. 25% confluency with 4 ml medium in 6-cm plates. This was followed by addition of calcium-NDA precipitates made by mixing 10 μg of total DNAs and 0.25 M CaCl$_2$ in BES-buffered saline containing 25 mM BES-NaOH, pH7.3, 0.14 M NaCl, Na$_2$HPO4. After 24 hr incubation, cells were washed with phosphate-buffer saline and then cultured in fresh medium for another 24 hr before harvesting.

Cell stimulation, extraction, immunogrecipitation and Western blotting analyses. Transfected Jurkat and 293 cells were left untreated or treated with 0.1 mM pervanadate for 30 min. After washing with ice-cold phosphate-buffered saline, the cells were lysed in Buffer A containing 50 mM β-glycerophosphate (pH 7.3), 0.1 M NaCl, 5 mM EDTA, 1 mM EGTA, 5 mM β-mercaptoethanol, 1% Triton X-100, 0.2 mM Na$_3$VO$_4$, 0.1 μM microcystin, 1.0 mM benzamidine, 0.1 mM phenylmethylsulfonyl fluoride, 20 μg/ml leupeptin, 1 μM pepstatin A, and 1 μg/ml aprotinin. Extracts were cleared by centrifugation.

For immunoprecipitation, cell extracts were incubated overnight with the anti-PZR and anti-SHP-2 antibodies pre-bound to protein A-Sepharose. The beads were washed three times with Buffer A supplemented with 0.15 M NaCl.

For Western blot analyses, samples were separated by 10% SDS-PAGE and transferred to polyvinylidene difluoride membranes. The membranes were probed with various primary antibodies and were detected by using the ECL system with horseradish peroxidase-conjugated secondary antibodies (Amersham, Piscataway, N.J.).

In vitro dephosphorylation of PZR by SHP-2. One plate (150 mm) of 293 cells were treated with 0.1 mM pervanadate for 30 min and cells were extracted as described above. The cell extract was subjected immunoprecipitation with anti-PZR serum as described above. After washing 3 times with the aforementioned immunoprecipitation washing buffer, beads were washed with PTP assay buffer containing 25 mM Tris-HCl (pH 7.0), 1.0 mM EDTA, 2 mM dithiothreitol, and 0.1% Triton X-100. The beads were suspended in the PTP assay buffer and were equally divided into 40-μl aliquots. The dephosphorylation reaction was started by addition of 0.6 μg of purified full-length recombinant SHP-2 or its SH2 domain-truncated form, ΔSHP-2 (Zhao, Z., et al. (1994) *J. Biol. Chem.* 269:8780–8785). The reaction was allowed to proceed at room temperature for up to one hour before termination with SDS gel sample buffer. Dephosphorylation of PZR was analyzed by Western blot with anti-phosphotyrosine antibody.

Example 6

Tyr241 and Tyr263 of PZR Are Phosphorylated and Are Responsible for Binding of SHP-2

Examples 1–3 above show that tyrosine-phosphorylated PZR specifically recruits SHP-2. Among the four tyrosyl residues in the intracellular portion of the protein, Tyr241 and Tyr263 embedded in the ITIMs are most likely phosphorylated and responsible for the binding of SHP-2. To verify this, three Tyr-to-Phe mutant forms of PZR, namely, PZR(F241), PZR(F263), and PZR(F241, 263), were constructed, as shown in FIG. 4. These mutant constructs together with the pCDNA3 vector and the native PZR construct were used to transfect Jurkat cells by electroporation, and the transfected cells were stimulated with pervanadate. The cell extracts were subjected to immunoprecipitation with anti-PZR and anti-SHP-2 antibodies. This was followed by Western blot analyses with anti-phosphotyrosine. As described above, cells were treated with 0.1 mM pervanadate for 30 min. Cells extracts were immunoprecipitated with anti-PZR or anti-SHP-2 antibodies, and the immunoprecipitates were subjected to Western blot analyses with anti-phosphotyrosine, anti-SHP-2, and anti-PZR.

In comparison with the marked tyrosine phosphorylation of the native form of PZR, mutation of either Tyr241 or 263 caused a significant decrease in tyrosine phosphorylation whereas mutation of both tyrosine residues to phenylalanine resulted in a total loss of tyrosine phosphorylation. Western blot analyses with anti-PZR antibody revealed essentially equal expressions of PZR and its mutant in Jurkat cells. These data thus indicate that Tyr241 and Tyr263 are responsible for tyrosine phosphorylation of PZR. Furthermore, as shown by the tyrosine phosphorylated SHP-2 co-immunoprecipitated with PZR, binding of SHP-2 with PZR was abolished by mutation of a single site, suggesting simultaneous phosphorylation of both sites is required for recruitment of SHP-2 to PZR. Immunoprecipitation with anti-SHP-2 further verified the results.

Both anti-phosphotyrosine and anti-PZR blots revealed strong binding of SHP-2 with the native form of PZR and minimal binding with the mutant forms of PZR. The tyrosine-phosphorylated protein of about 95 kDa co-immunoprecipitated with SHP-2 in vector control cells was absent in cell over-expressing native form of PZR. This is probably due to a competition of PZR with the protein for binding to SHP-2 presumably through a similar interaction mechanism. Similar results were observed when 293 cells were used for expression of the PZR constructs although presence of high level endogenous PZR in the cells had a slightly interfering effect.

Example 7

SH2 Domains of SHP-2 Are Required for Association with PZR

The binding SHP-2 with PZR is contemplated to be mediated by the interaction between SH2 domains of SHP-2 and the ITIMs of PZR. To confirm this, site-specific mutagenesis of the SH2 domain of SHP-2 was performed. Crystal structure of SH2 domains revealed that residues ArgA2 and ArgB5 have crucial in binding by chelating the phosphotyrosine phosphate (Pawson, T. (1995) *Nature* 373:573–580). The latter is within the conserved FLVRES sequence and corresponds to Arg32 and Arg138 of the N-terminal and C-terminal SH2 domains of SHP-2, respectively. The Arg-to-Lys mutant forms of SHP-2 and SH2 domain-truncated SHP-2 are shown by the schematic diagram in FIG. 5. These constructs, including SHP-2, SHP-2(R32-K), SHP-2(R138-K), and SH2 domain-truncated form, ΔSHP-2, were used to transfect 293 cells.

To increase the level of PZR, cells were co-transfected with the native form of PZR as described above. The reason for using 293 cells instead of Jurkat cell as described above because of difficulties in expressing high levels of SHP-2 in Jurkat cells. The transfected 293 cells were treated with 0.1 mM pervanadate to induce tyrosine phosphorylation, and cells extracts were immunoprecipitated with anti-SHP-2 antibodies. Western blot analysis of the immunoprecipitates with anti-PZR and anti-SHP-2 was performed. Cross-reactivity with the heavy chain of immunoglobulin G was observed. Additionally, compared with the native form of SHP-2, mutation of either arginyl residues caused marked decrease in binding of PZR with SHP-2. Moreover, some of binding seen can be attributable to co-immunoprecipitation with endogenous SHP-2 as found in cell transfected with the SH2 domain-truncated ΔSHP-2. This Example thus indicates that the tandem SH2 domains of SHP-2 are responsible for binding with PZR, and that both are required.

Example 8

SH2 Domains of SHP-2 Are Responsible for Hyperphosphorylation of PZR in Cells Expressing Catalytically Mutant Forms of the Enzyme As described herein above, over-expression of catalytically inactive Cys-to-Ser mutant but not the native form of SHP-2 caused hyperphosphorylation of PZR, suggesting that PZR is a putative substrate of SHP-2. One possible mechanism that the catalytically inactive SHP-2 prevents dephosphorylation of PZR is by binding the phosphotyrosyl motif through the catalytic domain directly. However, the Examples described above suggests that interaction between PZR and SHP-2 is mediated by interaction between tyrosine-phosphorylated ITIMs of PZR and SH2 domains of SHP-2, implying that PZR primarily serves as an anchor for SHP-2. Binding of SH2 domains to the ITIMs of PZR would also prevent the latter from dephosphorylation by SHP-2 or other PTPs.

To clarify this, 293 cells were transfected with a variety of catalytically inactive forms of SHP-2 as illustrated in FIG. 4. This was followed by analysis of tyrosine phosphorylation of intracellular proteins in non-stimulated cells. The expression of various forms of SHP-2 was determined by Western blotting with anti-SHP-2 serum while tyrosine phosphorylation of PZR was analyzed by anti-phosphotyrosine immunoblotting of whole cell extracts and anti-PZR immunoprecipitates.

As expected, overexpression of SHP-2(C-S) which has intact SH2 domains caused strong phosphorylation of PZR which was also associated with SHP-2(C-S). When either one of the SH2 domains were mutated, phosphorylation of PZR had a marked decrease but was still visible. However, essentially no association of the mutant SHP-2 with PZR was found. When both SH2 domains were removed, no phosphorylation of PZR was observed, even when the truncated Cys-to-Ser mutant was targeted to the plasma membrane by attaching a myristoylation tag. This indicates that the catalytic domain alone is not sufficient to induce tyrosine phosphorylation of PZR. This might be attributable to a low affinity of the SH2 domain-truncated Cys-to-Ser mutation to the ITIMs of PZR.

These results also suggest that SH2 domain of SHP-2 is responsible for preventing dephosphorylation of PZR. This further supported by the fact that expression of two SH2 domains of SHP-2 alone in 293 cells caused tyrosine phosphorylation of PZR. Nonetheless, the fact that overexpression of native form of SHP-2 does not enhance tyrosine phosphorylation of PZR suggests that native SHP-2 is able to dephosphorylate PZR. In this regard, pervanadate induced-tyrosine phosphorylation of PZR and its association with SHP-2 can also be attributed to inactivation of SHP-2.

Example 9

PZR Is Efficiently Dephosphorylated by Full-length SHP-2 But Not by its SH2 Domain-truncated Form To further verify the specific dephosphorylation of PZR by SHP-2, in vitro dephosphorylation of PZR was performed. Tyrosine-phosphorylated PZR was immuno-purified from pervanadate-treated 293 cells and incubated with full-length SHP-2 and its SH2 domain-truncated form, ΔSHP-2. Previous studies have shown that truncation of the SH2 domains causes nearly 50-fold activation of the enzyme (Zhao, Z., et al. (1994) *J. Biol. Chem.* 269:8780–8785).

For the samples used in this Example, the specific activities toward 10 mM para-nitrophenylphosphate analyzed at pH 5.0 were 1,800 and 33,000 units/ml for the full length SHP-2 and the truncated enzyme, respectively. However, when equal protein amounts of the enzymes were used to treat tyrosine-phosphorylated PZR, full length SHP-2 caused rapid dephosphorylation while the truncated enzyme had essentially no effect. These data indicate that binding of SHP-2 to PZR through its SH2 domains greatly enhanced activity to PZR while the SH2 domain-truncated ΔSHP-2, despite its high activity towards low-molecular-weight artificial substrate para-nitrophenylphosphate, does not have sufficient affinity to bind and thereby to dephosphorylate PZR. The high affinity of the full-length SHP-2 to PZR is contemplated to be conferred by the high-affinity, specific SH2 domain-ITIMs interaction.

While it is not applicant's desire to be bound by any particular theory of operation, it is contemplated that the dephosphorylation likely occurs through conformational changes (which may be slow) within a PZR-SHP-2 complex that renders the catalytic domain of SHP-2 to attack the phosphotyrosyl residues of PZR. Nonetheless, one can not rule out the possibility for an inter-complex reaction in which one PZR-complexed SHP-2 molecule attacks a different PZR molecule in another complex, although the efficiency might be lower in comparison with the intra-complex reaction.

It should also be noted that dephosphorylation of PZR by SHP-2 was not complete. The residual tyrosine phosphorylation of PZR may be attributed to a competition from pervanadate-inactivated SHP-2 that was co-immunoprecipitated with tyrosine-phosphorylated PZR. Indeed, higher concentrations of SHP-2 (up to 5 $\mu$g/ml) helped to push the dephosphorylation to near completion. Together, the data suggest that PZR is a substrate as well as an anchoring protein of SHP-2 and that efficient dephosphorylation requires binding of SHP-2 to PZR through the interaction between ITIMs and SH2 domains.

Discussion of Examples 6–9

By specially mutating tyrosyl residues of PZR and SH2 domain of SHP-2, Examples 6–9 demonstrate that Tyr241 and Tyr263 embedded in ITIMs are responsible for phosphorylation of PZR and both are required for binding with SHP-2 through its SH2 domains. In accordance with the present invention, it is contemplated that PZR serves as an anchor protein of SHP-2 on the plasma membrane.

SH2 domain proteins transmit intracellular signals initiated by activated tyrosine kinase-linked receptors. Three-dimensional structures suggest mechanisms by which tandem SH2 domains might confer higher specificity than individual SH2 domains (Eck, M. J., et al. (1996) *Nature* 379:277–280; Hof, P., et al. (1998) *Cell* 92:441450). In vitro studies with phosphopeptides revealed that tandem SH2 domains bind bis-phosphotyrosyl peptides 20–50-fold stronger than individual SH2 domains (Ottinger, E. A., et al. (1998) *J. Biol. Chem.* 273:729–735). By showing that efficient co-immunoprecipitation of PZR with SHP-2 requires interaction of the tandem SH2 domains of SH2 and both ITIMs of PZR, Examples 6–9 provide evidence at the cellular level that high biological specificity is conferred by the simultaneous interaction of two SH2 domains in a signaling enzyme with di-phosphorylated motifs in activated receptors or their substrates.

SHP-2 has been shown to bind to a number of growth factor receptors (Streuli, M. (1996) *Curr. Opinion in Cell Biol.* 183:182–188; Stein-Gerlach, M., et al. (1998) *Int. J. Biochem. Cell. Bio.* 30, 559–566). However, in many cases, the interactions seem to be mediated by a single SH2 domain and only a small fraction of SHP-2 and receptors were found associated. The physiological meaning of this binding might be different. Many signaling molecules with tandem SH2 domains interact with bis-phosphotyrosyl motifs. These motifs include immunoreceptor-tyrosine-based activation motifs (ITAMs) and the aforementioned ITIMs. Studies have shown that the space between the phosphotyrosine residues of the motifs is crucial for binding. In ITAMs, the tyrosyl residues are usually separated by 9–11 amino acid residues (Unkeless, J. C., and Jin, J. (1997) *Curr. Opin. Immunol.* 9:338–343). Crystal structure of the tandem SH2 domains of ZAP-70 suggests such a space would be optimal to bind its correspondent ITAMs (Hatada, M. H., et al. (1995) *Nature* 377:32–38).

For ITIMs, it appears that more amino acid residues are required to fill the space. The ITIMs in PZR are separated by 21 aa, whereas those in KIR by 29, in LAIR-1 by 29, PIR-B by 29, PECAM by 22, in CD22 by 33 and 19, and in SHPS-1/SIRP by 23 and 25. This long stretch can be explained by the fact that the correspondent tandem SH2 domains (e.g., SHP-2) in the intact enzyme are oriented differently, spaced widely and perpendicular to one another, so that they require the bisphosphotyrosyl ITAMs sequences to change direction to bind both sites (Eck, M. J., et al. (1996) *Nature* 379:277–280; Hof, P., et al. (1998) *Cell* 92:441–450). It should be noted that while the ITIMs found in other proteins have one or more proline residues separating the tandem ITIMs, the 21 amino acid residues between the two ITIMs of PZR have two consecutive glycyl residues instead which might also facilitate a turn. In addition, this stretch contain 4 seryl residues each surrounded by charged amino acid residues (3 His, 2 Lys, 2 Asp, and 1 Glu) and may provide phosphorylation sites thereby regulating interaction of tandem SH2 domains and the ITIMs. The unique spacing amino acid residues between the two ITIM tyrosyl residues of PZR is thus a distinct feature of the molecule.

By showing that catalytically inactive but not active forms of SHP-2 caused hyper-phophorylation of PZR in vivo and that PZR can be efficiently dephosphorylated by full-length but not SH2 domain-truncated SHP-2 in vitro, it is contemplated in accordance with the present invention that PZR is a physiological substrate of SHP-2. Overexpression of catalytically inactive mutants of SHP-2 causes hyper-phosphorylation of PZR through occupation of phosphorylation sites by SH2 domain. However, overexpression of the native enzyme did not have such an effect. This suggests that SH2 domain of SHP-2 is able to prevent dephosphorylation of PZR by other enzymes but not by itself.

Therefore, tyrosines 247 and 263 serve as binding site for SH2 domains of SHP-2 but can also be dephosphorylated by its catalytic domain. Binding of SHP-2 to tyrosine-phosphorylated PZR brings SHP-2 to the plasma membrane and causes its activation. Activated SHP-2 in turn dephosphorylates certain proteins in vicinity and thereby initiate signal transduction. On the other hand, SHP-2 can also dephosphorylate PZR and thereby terminate the signal transduction initiated by phosphorylation of PZR. Furthermore, the binding and dephosphorylation process which form a futile cycle driven by hydrolysis of ATP enables phosphorylation of PZR and activity of SHP-2 stay at relative high basal levels and thus set a threshold for signal transduction to be initiated.

The ITIMs were defined inhibitory motifs because they are initially found in inhibitory immunoreceptors like Fc$\lambda$RIIB and KIR and they mediate the inhibitory effects of these proteins on signal transduction. Unkeless, J. C., and Jin, J. (1997) *Curr. Opin. Immunol.* 9:338–343; Vely, F., et al. (1997) *Eur. J. Immunol.* 27:1994–2000; Vely, F., and Vivier, E. (1997) *J. Immunol.* 159:2075–2077; Isakov, N. (1997) *Immunol. Res.* 16:85–100. Furthermore, since phosphorylation of the tyrosyl residue in the ITIMs triggers binding and activation of SH2 domain-containing phosphatases like the tyrosine phosphatases SHP-1 and SHP-2 and the inositol phosphatase SHIP (Unkeless, J. C., and Jin, J. (1997) *Curr. Opin. Immunol.* 9:338–343; Vely, F., et al. (1997) *Eur. J. Immunol.* 27:1994–2000; Vely, F., and Vivier, E. (1997) *J. Immunol.* 159:2075–2077; Isakov, N. (1997) *Immunol. Res.* 16:85–100), the inhibitory function of ITIMs is thought to be executed by these phosphatases. It should noted, however that that not all dephosphorylation means down-regulation of signal transduction. On the contrary, in many cases, dephosphorylation results in initiation of signal transduction. Hunter, T. (1995) *Cell* 80:225–236. For example, SHP-2 has been largely considered as a positive signal transducer (Streuli, M. (1996) Curr. Opinion in Cell Biol. 183:182–188; Stein-Gerlach, M., et al. (1998) Int. J. Biochem. Cell. Biol. 30, 559–566). In fact, the positive role of SHPS-1 in growth factor-induced MAP kinase activation is believed to be mediated by SHP-2 (Takada, T., et al. (1998) J. Biol. Chem. 273:9234–9242). Since the ITIMs are found in more and more diverse signaling molecules, their functions may also be diversified.

PZR is unique in that it interacts specifically with SHP-2 but not with SHP-1, while most other ITIM-containing proteins including KIR, PECAM, PIRB, and SIRP/SHPS-1, gp49 which bind both SHP-1 and SHP-2. Olcese, L., et al. (1996) J. Immunol. 156:4531–4534; Veillette, A., et al. (1998) J. Biol. Chem. 273:22719–22728; Maeda, A., et al. (1998) J. Exp. Med. 187:1355–1360; Kuroiwa, A., et al. (1998) J. Biol. Chem. 273:1070–1074; Cao, M. Y., et al. (1998) Biol. Chem. 273:15765–15772; Sagawa, K., et al. (1997) J. Biol. Chem. 272:31086–31091; Jackson, D. E., et al. (1997) J. Biol. Chem. 272:24868–24875. In accordance with the present invention, it is thus contemplated that PZR is a binding protein as well as a physiological substrate of SHP-2.

Example 10

Phosphorylation of PZR Upon Cell Adhesion

Suspended HT-1080 cells were added to plates coated with fibronectin for 0, 15, 30, 60, and 120 minutes prior to extraction. Cell extracts were immunoprecipitated with anti-PZR antibodies, and the immunoprecipitates were subjected to Western blot analyses with anti-phosphotyrosine. It was observed that PZR is phosphorylated upon cell adhesion.

Example 11

PZR Mediates Action of Concanavalin A

It has been generally accepted that complex carbohydrates play a role in the regulation of cell adhesion and cell proliferation. This was demonstrated by the use of polyvalent anti-carbohydrate antibodies and plant lectins that modulate cell surface carbohydrates. Notably, Burger and Noonan (1970) Nature 228(271):512–5 demonstrated restoration of contact inhibition of malignant cells by monovalent concanavalin A (Con A). However, the potential uses of lectins as therapeutic drugs are tempered by their nonspecificities. In addition, the precise mechanism by which these lectins function to regulate adhesion and proliferation is not clear. In this Example it is demonstrated that cell surface glycoprotein PZR of the present invention mediates the action of Con A.

Con A induces tyrosine phosphorylation of PZR. When serum-starved HT-1080 cells were treated with 100 $\mu$g/ml Con A, tyrosine phosphorylation of a major protein of around 43 kDa was observed after 20 min. The protein co-migrated with cell surface glycoprotein PZR. Immunoprecipitation of the cell extracts with anti-PZR antibody caused total depletion of the tyrosine phosphorylated protein from the cell extracts, indicating the protein corresponds to PZR. Anti-phosphotyrosine Western blot analysis of the PZR immunoprecipitates further verified the results. Tyrosine phosphorylation of PZR appeared after 5 min of Con A treatment, peaked at 40 min, and slightly declined thereafter. The phosphorylation also depended on the dose of Con A with a saturation concentration of 50 $\mu$g/ml. As a major tyrosine phosphorylated protein in Con A-treated cells, PZR mediates the action of Con A.

PZR mediates Con A-induced cell agglutination. By clustering cell surface glycoproteins, Con A displays agglutinating activities. To examine whether PZR mediates the action Con A, the native form and an intracellular domain-truncated form of PZR, PZRX (SEQ ID NOs:41–48), were expressed in HT 1080 cells. Upon treatment of the cells with Con A, cells over-expressing PZR showed drastic agglutination. In contrast, expression of the truncated form totally blocked the process. Control cells had moderate agglutination after 2 hr of treatment.

To reveal the signal transduction mechanism, the tyrosine phosphorylation of PZR was analyzed. Expression of PZRX abolished the tyrosine phosphorylation of PZR induced by Con A. Con A functions by clustering cell surface carbohydrate groups. As a highly glycosylated protein, PZR is contemplated to be a major target of Con A, and tyrosine phosphorylation of PZR is caused by Con A-induced dimerization or oligomerization. In this regard, the PZRX mutant plays a dominant negative role. Since cell agglutination of the adherent cell involved cell migration and cell adhesion, the data establish a role for PZR in these processes. The action of Con A can be mimicked specifically by anti-PZR antibodies that recognizes the extracellular segment of PZR. Therefore, PZR antibodies have therapeutic application. Soluble forms of PZR can also be used to modulate normal function of cell surface PZR.

Example 12

PZR Promotes Cell Aggregation, Spreading, and Migration

Stable HT-1080 cell lines overexpressing the native form of PZR and an intracellular domain-truncated form of PZR, PZRX (SEQ ID NOs:41–48), were generated. DNA plasmids carrying full length and truncated PZR cDNA together the antisense cDNA were used to transfect HT-1080 cells. Clonal cell lines were isolated by G418 selection. Most of the clones selected over-expressed a substantial level of exogenous PZR as compared with the antisense clones which is essentially equal to the parental cells. Sequential dilution of cell extracts followed by Western blotting analysis revealed about 6–8-fold over-expression of PZR. Two clonal cell lines were used for cell aggregation, spreading, and migration analyses.

In comparison with antisense control which exhibited essentially no cell aggregation, cells overexpressing the full PZR or intracellular domain-truncated form of PZR displayed significant cell aggregation. After 1 hr incubation, over 50% cells are found in aggregated forms (clusters of 3 cells or more). These results indicate that PZR promotes cell-cell interaction through its extracellular domain. However, expression of the truncated PZRX displayed impaired cell spreading as indicated by the round and spherical morphorlogy of the cells after attachment to fibronectin-coated plates. This suggests that intracellular domain of PZR is involved in cell signaling that controls cell spreading.

The effects of PZR expression on cell migration was also analyzed. Expression of PZRX caused significant inhibition of cell migration while expression of the native PZR resulted in enhanced migration. The impaired migration of the cells caused by expression of PZRX agrees with the inhibition of Con A-induced agglutination caused by expression of PZRX with the same cells. These data indicate that the extracellular domain of PZR is involved in cell adhesion while transduction of its signal to change cell behaviors requires participation of its intracellular domain.

HT-1080 cells were stably transfected with plasmids carrying native sense PZR, anti-sense PZR, and intracellular domain-truncated PZRX. Cells were starved with 0% serum for 24 hr and then detached by further incubation in PBS. PBS-suspended cells were past through a 26 gauge syringe needle to form single cells. Aggregation was started by addition of serum-free DMEM medium, and the cell concentration was $1\times10^6$/ml. Phase contrast photos were taken after 2 hr of shaking at room temperature. A uniform distribution of the anti-sense cells was observed.

Cells were then added to fibronectin-coated tissue culture plates. Phase contrast photos were taken after 1 hr of incubation at 37° C. Spherical morphology of the cells over-expressing PZRX, in comparison with the sense and anti-sense cells, was observed. For migration assay, membrane of Transwell plates were coated with 10 ng/ml fibronectin overnight. The lower chambers were filled with DMEM containing 4 ng/ml fibronectin. Cells ($2\times10^5$) in DMEM were added to the upper chambers. This was followed by incubation at 37° C. for 5 hr before fixing of the cells with methanol. Cells in the inner surface of the membrane were mechanically removed by a cotton swab. Cells remained on outer surface of the membrane were stained with Gimsa. Phase contrast photos were taken with 100x amplification. Pores of the membranes appeared as small open circles.

REFERENCES

The references listed below as well as all references cited in the specification are incorporated herein by reference to the extent that they supplement, explain, provide a background for or teach methodology, techniques and/or compositions employed herein.

Adelman et al. (1983) DNA 2:183.
Ahmad, S., et al. (1993) Proc. Natl. Acad. Sci. USA. 90:2197–2201.
Ausubel et al. (1992) Current Protocols in Molecular Biology, (J. Wylie & Sons, N.Y.).
Bennett, A. M., et al. (1996) Mol. Cell. Biol. 16:1189–1202.
Blery, M., et al. (1998) Proc. Natl. Acad. Sci. U.S.A. 95:2446–2451.
Bodanszky, et al., "Peptide Synthesis", John Wiley & Sons, Second Edition, 1976.
Burger and Noonan (1970) Nature 228(271):512–5.
Byon, J. C., et al. (1997) Proc. Soc. Exp. Biol. & Med. 216:1–20.
Cao, M. Y., et al. (1998) Biol. Chem. 273:15765–15772.
Carlberg, K. and Rohrschneider, L. R. (1997) J. Biol. Chem. 272:15943–15950.
Chen, C. and Okayama, H. (1987) Mol. Cell. Biol. 7:2745–2752.
Choe S. (1996) Neuron 17:363–365.
Colonna, M. and Samaridis, J. (1995) Science 268:405–408.
Crea et al. (1978) Proc. Natl. Acad. Sci. U.S.A, 75:5765.
David, M., et al. (1996) J. Biol. Chem. 271:15862–15865.
Eck, M. J., et al. (1996) Nature 379:277–280.
Eichenlaub et al. R. J. Bacteriol 138:559–566,1979.
Fields et al., Int. J. Peptide Protein Res. 35:161–214 (1990).
Filbin, M. T. and Tennekoon, G. I. (1992) Bioessays 14:541–547.
Fischer, E. H., Charbonneau, H., and Tonks, N. K. (1991) Science 253:401–6.
Frearson, J. A. and Alexander, D. R. (1997) Bioessays 19:417–427.
Frearson, J. A., et al. (1996) Eur. J. Immunol. 26:1539–1543.
Fujioka, Y., et al. (1996) Mol. Cell. Biol. 16:6887–6899.
Gillmor et al. (1997) Nature Struct. Biol. 4:1003–1009.
Green et al. (1989) J. Invest. Dermatol. 93:486–491.
Gu, H., et al. (1995) Brain 118:809–818.
Hatada, M. H., et al. (1995) Nature 377:32–38.
Hof, P., et al. (1998) Cell 92:441–450.
Hopp, U.S. Pat. No. 4,554,101.
Howell et al. (1988) Antibodies A Laboratory Manual, (Cold Spring Harbor Laboratory).
Hunter, T. (1995) Cell 80:225–236.
Isakov, N. (1997) Immunol. Res. 16:85–100.
Jackson, D. E., et al. (1997) J. Biol. Chem. 272:24868–24875.
Jiao, H., et al. (1997) Exp. Hematol. 25:592–600.
Keski-Oja et al., J. Cell Biochem. 33:95 (1987).
Kharitonenkov, A., et al. (1997) Nature 386:181–186.
Kozak, M. (1989) J. Cell. Biol. 108, 229–241.
Kuroiwa, A., et al. (1998) J. Biol. Chem. 273:1070–1074.
Kyte et al. (1982) J. Mol. Biol. 157: 105.
Lee, C. H., et al. (1994) Structure 2:423–438.
Maeda, A., et al. (1998) J. Exp. Med. 187:1355–1360.
McOmie, "Protective Groups in Organic Chemistry", Plenum Press, New York,(1973).
Meienhofer, "Hormonal Proteins and Peptides", Vol. 2, p. 46, Academic Press (New York) (1983).
Merrifield, Adv Enzymol, 32:221–96 (1969).
Messing et al. (1981) Third Cleveland Symposium on Macromolecules and Recombinant DNA, Editor A. Walton, (Elsevier, Amsterdam).
Meyaard, L., et al. (1997) Immunity 7:283–290.
Milarski, K. L. and Saltiel, A. L. (1994) J. Biol. Chem. 269:21239–21243.
Muta, T., et al. (1994) Nature 368:70–73.
Needleman et al., J. Mol. Biol. 48:443 (1970).
Neel, B. G. and Tonks, N. K. (1997) Curr. Opin. Cell. Biol. 9:193–204.
Newman, P. J., et al. (1990) Science 247:1219–1222.
Noguchi, T., et al. (1994) Mol. Cell. Biol. 14:6674–6682.
Olcese, L., et al. (1996) J. Immunol. 156: 4531–4534.
Ottinger, E. A., et al. (1998) J. Biol. Chem. 273:729–735.
Pawson, T (1995) Nature 373:573–580.
Perkins, L. A., et al. (1992) Cell 70:225–236.
Qu, C. K., et al. (1997) Mol. Cell. Biol. 17:5499–5507.
Rivard, N., et al. (1995) J. Biol. Chem. 270:11017–11024.
Ruff, S. J., Chen, K., and Cohen S. (1997) J. Biol. Chem. 272:1263–1267.
Sagawa, K., et al. (1997) J. Biol. Chem. 272:31086–31091.
Sambrook et al. (1989) Molecular Cloning: A Laboratory Manual (Cold Spring Harbor Laboratory Press, Cold Spring Harbor, N.Y.).
Saxton, T. M., et al. (1997) EMBO J. 16:2352–2364.
Scharenberg, A. M. and Kinet, J. P. (1996) Cell 87:961–964.

Schroder et al., "The Peptides", Vol. 1, Academic Press (New York) (1965).
Shapiro, L., et al. (1996) Neuron 17:435–449.
Smith et al., Adv. Appl. Math. 2:482 (1981).
Stamenkovic, I., and Seed, B. (1990) Nature 345:74–77.
Stein-Gerlach, M., et al. (1998) Int. J. Biochem. Cell. Biol. 30:559–566.
Steward et al., "Solid Phase Peptide Synthesis", W. H. Freeman Co., San Francisco (1969).
Streuli, M. (1996) Curr. Opinion in Cell Biol. 183:182–188.
Su, L., et al. (1996) J. Biol. Chem. 271:10385–10390.
Takada, T., et al. (1998) J. Biol. Chem. 273:9234–9242.
Tanaka, A., et al. (1987) Mol. Cell. Biol. 7:1878–1983.
Tang, T. L., et al. (1995) Cell 80:473–483.
Tonks, N. K., & Neel, B. G. (1996) Cell 87:365–368.
U.S. Pat. No. 5,583,103
U.S. Pat. No. 5,624,816
U.S. Pat. No. 5,625,125
U.S. Pat. No. 5,627,158
U.S. Pat. No. 5,641,484
U.S. Pat. No. 5,643,567
U.S. Pat. No. 5,489,742
U.S. Pat. No. 5,399,346
U.S. Pat. No. 5,352,660
U.S. Pat. No. 5,326,902
U.S. Pat. No. 5,286,634
U.S. Pat. No. 5,279,833
U.S. Pat. No. 5,589,375
U.S. Pat. No. 5,234,933
U.S. Pat. No. 5,645,999
U.S. Pat. No. 5,651,964
U.S. Pat. No. 5,573,933
U.S. Pat. No. 5,648,061
U.S. Pat. No. 5,614,396
U.S. Pat. No. 4,683,202
U.S. Pat. No. 4,244,946
U.S. Pat. No. 5,580,979
U.S. Pat. No. 4,196,265
U.S. Pat. No. 3,095,355
U.S. Pat. No. 2,868,691
U.S. Pat. No. 5,723,593
U.S. Pat. No. 5,734,033
U.S. Pat. No. 5,739,278
U.S. Pat. No. 5,741,957
U.S. Pat. No. 5,753,687
U.S. Pat. No. 5,770,609
U.S. Pat. No. 5,776,902
U.S. Pat. No. 5,120,535
U.S. Pat. No. 5,780,436
U.S. Pat. No. 5,786,152
U.S. Pat. No. 5,162,215
U.S. Pat. No. 5,550,316
U.S. Pat. No. 4,736,866
U.S. Pat. No. 4,686,283
U.S. Pat. No. 5,693,488
U.S. Pat. No. 5,436,288
Ullrich, A. and Schlessinger, J. (1990) Cell 61:203–212.
Ulyanova, T., et al. (1997) Immunolog. Res. 16:101–113.
Unkeless, J. C., and Jin, J. (1997) Curr. Opin. Immunol. 9:338–343.
Valiante, N. M., et al. (1996) J. Exp. Med. 184:2243–2250.
Veillette, A., et al. (1998) J. Biol. Chem. 273:22719–22728.
Vely, F., et al. (1997) Eur. J. Immunol. 27:1994–2000.
Vely, F. and Vivier, E. (1997) J. Immunol. 159:2075–2077.
Walton, K. M. and Dixon, J. E. (1993) Annu. Rev. Biochem. 62:101–20.
Wetmur & Davidson (1968) J. Mol. Biol. 31:349–370.
WO 93/25521
WO 96/40276
Xiao, S., et al. (1994) J. Biol. Chem. 269:21244–21248.
Yamauchi, K., et al. (1995) J. Biol. Chem. 270:17716–17722.
Yamauchi, K., et al. (1995) Proc. Natl. Acad. Sci. U.S.A. 92:664–668.
Yu, D. H., et al. (1998) J. Biol. Chem. 273:21125–21131.
Zhao, Z., et al. (1993) J. Biol. Chem. 268:2816–2820.
Zhao, Z., et al. (1994) J. Biol. Chem. 269:8780–8785.
Zhao, Z., et al. (1995) J. Biol. Chem. 270:11765–17769.
Zhao, Z., et al. (1995) Adv. in Protein Phosphatases 9:297–317.
Zhao, Z., et al. (1996) J. Biol. Chem. 271:22251–22255.
Zhao, Z. J. and Zhao, R. (1998) J. Biol. Chem. 273:29367–29372.
Zhao, R. and Zhao, Z. J. (1999) Biochem. J. 338:35–39.
Zimmer et al., Peptides 1992, pp. 393–394, ESCOM Science Publishers, B. V., 1993.

SEQUENCE LISTING

<160> NUMBER OF SEQ ID NOS: 49

<210> SEQ ID NO 1
<211> LENGTH: 1151
<212> TYPE: DNA
<213> ORGANISM: Homo sapiens
<220> FEATURE:
<221> NAME/KEY: gene
<222> LOCATION: (1)..(1151)

```
-continued

<220> FEATURE:
<221> NAME/KEY: CDS
<222> LOCATION: (133)..(939)

<400> SEQUENCE: 1
gcgcgggttg gaggtgccac ccggcgcggg tggcggagag atcagaagcc tcttccccaa      60
gccgagccaa cctcagcggg gacccgggct cagggacgcg gcggcggcgg cggcgactgc     120
agtggctgga cg atg gca gcg tcc gcc gga gcc ggg gcg gtg att gca gcc    171
              Met Ala Ala Ser Ala Gly Ala Gly Ala Val Ile Ala Ala
                1               5                  10 cca gac agc cgg cgc tgg ctg tgg tcg gtg ctg gcg gcg gcg ctt ggg     219
Pro Asp Ser Arg Arg Trp Leu Trp Ser Val Leu Ala Ala Ala Leu Gly
         15                  20                  25 ctc ttg aca gct gga gta tca gcc ttg gaa gta tat acg cca aaa gaa     267
Leu Leu Thr Ala Gly Val Ser Ala Leu Glu Val Tyr Thr Pro Lys Glu
 30                  35                  40                  45 atc ttc gtg gca aat ggt aca caa ggg aag ctg acc tgc aag ttc aag     315
Ile Phe Val Ala Asn Gly Thr Gln Gly Lys Leu Thr Cys Lys Phe Lys
                 50                  55                  60 tct act agt acg act ggc ggg ttg acc tca gtc tcc tgg agc ttc cag     363
Ser Thr Ser Thr Thr Gly Gly Leu Thr Ser Val Ser Trp Ser Phe Gln
             65                  70                  75 cca gag ggg gcc gac act act gtg tcg ttt ttc cac tac tcc caa ggg     411
Pro Glu Gly Ala Asp Thr Thr Val Ser Phe Phe His Tyr Ser Gln Gly
         80                  85                  90 caa gtg tac ctt ggg aat tat cca cca ttt aaa gac aga atc agc tgg     459
Gln Val Tyr Leu Gly Asn Tyr Pro Pro Phe Lys Asp Arg Ile Ser Trp
 95                  100                 105 gct gga gac ctt gac aag aaa gat gca tca atc aac ata gaa aat atg     507
Ala Gly Asp Leu Asp Lys Lys Asp Ala Ser Ile Asn Ile Glu Asn Met
110                 115                 120                 125 cag ttt ata cac aat ggc acc tat atc tgt gat gtc aaa aac cct cct     555
Gln Phe Ile His Asn Gly Thr Tyr Ile Cys Asp Val Lys Asn Pro Pro
                 130                 135                 140 gac atc gtt gtc cag cct gga cac att agg ctc tat gtc gta gaa aaa     603
Asp Ile Val Val Gln Pro Gly His Ile Arg Leu Tyr Val Val Glu Lys
             145                 150                 155 gag aat ttg cct gtg ttt cca gtt tgg gta gtg gtg ggc ata gtt act     651
Glu Asn Leu Pro Val Phe Pro Val Trp Val Val Val Gly Ile Val Thr
         160                 165                 170 gct gtg gtc cta ggt ctc act ctg ctc atc agc atg att ctg gct gtc     699
Ala Val Val Leu Gly Leu Thr Leu Leu Ile Ser Met Ile Leu Ala Val
 175                 180                 185 ctc tat aga agg aaa aac tct aaa cgg gat tac act ggc tgc agt aca     747
Leu Tyr Arg Arg Lys Asn Ser Lys Arg Asp Tyr Thr Gly Cys Ser Thr
190                 195                 200                 205 tca gag agt ttg tca cca gtt aag cag gct cct cgg aag tcc ccc tcc     795
Ser Glu Ser Leu Ser Pro Val Lys Gln Ala Pro Arg Lys Ser Pro Ser
                 210                 215                 220 gac act gag ggt ctt gta aag agt ctg cct tct gga tct cac cag ggc     843
Asp Thr Glu Gly Leu Val Lys Ser Leu Pro Ser Gly Ser His Gln Gly
             225                 230                 235 cca gtc ata tat gca cag tta gac cac tcc ggc gga cat cac agt gac     891
Pro Val Ile Tyr Ala Gln Leu Asp His Ser Gly Gly His His Ser Asp
         240                 245                 250 aag att aac aag tca gag tct gtg gtg tat gcg gat atc cga aag aat     939
Lys Ile Asn Lys Ser Glu Ser Val Val Tyr Ala Asp Ile Arg Lys Asn
 255                 260                 265 taagagaata cctagaacat atcctcagca agaaacaaaa ccaaactgga ctctcgtgca     999
```
gaaaatgtag cccattacca catgtagcct tggagaccca ggcaaggaca agtacacgtg    1059
tactcacaga gggagagaaa gatgtgtaca aaggatatgt ataaatattc tatttagtca    1119
tccttaaaaa aaaaaaaaaa aaaaaaaaaa aa                                   1151

<210> SEQ ID NO 2
<211> LENGTH: 269
<212> TYPE: PRT
<213> ORGANISM: Homo sapiens

<400> SEQUENCE: 2

```
Met Ala Ala Ser Ala Gly Ala Gly Ala Val Ile Ala Ala Pro Asp Ser
  1               5                  10                  15

Arg Arg Trp Leu Trp Ser Val Leu Ala Ala Leu Gly Leu Leu Thr
                 20                  25                  30

Ala Gly Val Ser Ala Leu Glu Val Tyr Thr Pro Lys Glu Ile Phe Val
             35                  40                  45

Ala Asn Gly Thr Gln Gly Lys Leu Thr Cys Lys Phe Lys Ser Thr Ser
         50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp Tyr Thr Gly Cys Ser Thr Ser Glu Ser
        195                 200                 205

Leu Ser Pro Val Lys Gln Ala Pro Arg Lys Ser Pro Ser Asp Thr Glu
    210                 215                 220

Gly Leu Val Lys Ser Leu Pro Ser Gly Ser His Gln Gly Pro Val Ile
225                 230                 235                 240

Tyr Ala Gln Leu Asp His Ser Gly Gly His His Ser Asp Lys Ile Asn
                245                 250                 255

Lys Ser Glu Ser Val Val Tyr Ala Asp Ile Arg Lys Asn
            260                 265
```

<210> SEQ ID NO 3
<211> LENGTH: 1151
<212> TYPE: DNA
<213> ORGANISM: Homo sapiens
<220> FEATURE:
<221> NAME/KEY: gene
<222> LOCATION: (1)..(1151)
<220> FEATURE:
<221> NAME/KEY: CDS
<222> LOCATION: (133)..(939)

<400> SEQUENCE: 3

-continued

```
gcgcgggttg gaggtgccac ccggcgcggg tggcggagag atcagaagcc tcttccccaa        60 ccgagccaa cctcagcggg gacccgggct cagggacgcg gcggcggcgg cggcgactgc        120
agtggctgga cg atg gca gcg tcc gcc gga gcc ggg gcg gtg att gca gcc       171
              Met Ala Ala Ser Ala Gly Ala Gly Ala Val Ile Ala Ala
                1               5                   10 cca gac agc cgg cgc tgg ctg tgg tcg gtg ctg gcg gcg gcg ctt ggg         219
Pro Asp Ser Arg Arg Trp Leu Trp Ser Val Leu Ala Ala Ala Leu Gly
 15                  20                  25 atc ttg aca gct gga gta tca gcc ttg gaa gta tat acg cca aaa gaa         267
Ile Leu Thr Ala Gly Val Ser Ala Leu Glu Val Tyr Thr Pro Lys Glu
 30                  35                  40                  45 atc ttc gtg gca aat ggt aca caa ggg aag ctg acc tgc aag ttc aag         315
Ile Phe Val Ala Asn Gly Thr Gln Gly Lys Leu Thr Cys Lys Phe Lys
                 50                  55                  60 tct act agt acg act ggc ggg ttg acc tca gtc tcc tgg agc ttc cag         363
Ser Thr Ser Thr Thr Gly Gly Leu Thr Ser Val Ser Trp Ser Phe Gln
                 65                  70                  75 cca gag ggg gcc gac act act gtg tcg ttt ttc cac tac tcc caa ggg         411
Pro Glu Gly Ala Asp Thr Thr Val Ser Phe Phe His Tyr Ser Gln Gly
 80                  85                      90 caa gtg tac ctt ggg aat tat cca cca ttt aaa gac aga atc agc tgg         459
Gln Val Tyr Leu Gly Asn Tyr Pro Pro Phe Lys Asp Arg Ile Ser Trp
 95                 100                 105 gct gga gac ctt gac aag aaa gat gca tca atc aac ata gaa aat atg         507
Ala Gly Asp Leu Asp Lys Lys Asp Ala Ser Ile Asn Ile Glu Asn Met
110                 115                 120                 125 cag ttt ata cac aat ggc acc tat atc tgt gat gtc aaa aac cct cct         555
Gln Phe Ile His Asn Gly Thr Tyr Ile Cys Asp Val Lys Asn Pro Pro
                130                 135                 140 gac atc gtt gtc cag cct gga cac att agg ctc tat gtc gta gaa aaa         603
Asp Ile Val Val Gln Pro Gly His Ile Arg Leu Tyr Val Val Glu Lys
                145                 150                 155 gag aat ttg cct gtg ttt cca gtt tgg gta gtg gtg ggc ata gtt act         651
Glu Asn Leu Pro Val Phe Pro Val Trp Val Val Val Gly Ile Val Thr
                160                 165                 170 gct gtg gtc cta ggt ctc act ctg ctc atc agc atg att ctg gct gtc         699
Ala Val Val Leu Gly Leu Thr Leu Leu Ile Ser Met Ile Leu Ala Val
175                 180                 185 ctc tat aga agg aaa aac tct aaa cgg gat tac act ggc tgc agt aca         747
Leu Tyr Arg Arg Lys Asn Ser Lys Arg Asp Tyr Thr Gly Cys Ser Thr
190                 195                 200                 205 tca gag agt ttg tca cca gtt aag cag gct cct cgg aag tcc ccc tcc         795
Ser Glu Ser Leu Ser Pro Val Lys Gln Ala Pro Arg Lys Ser Pro Ser
                210                 215                 220 gac act gag ggt ctt gta aag agt ctg cct tct gga tct cac cag ggc         843
Asp Thr Glu Gly Leu Val Lys Ser Leu Pro Ser Gly Ser His Gln Gly
                225                 230                 235 cca gtc ata tat gca cag tta gac cac tcc ggc gga cat cac agt gac         891
Pro Val Ile Tyr Ala Gln Leu Asp His Ser Gly Gly His His Ser Asp
                240                 245                 250 aag att aac aag tca gag tct gtg gtg tat gcg gat atc cga aag aat         939
Lys Ile Asn Lys Ser Glu Ser Val Val Tyr Ala Asp Ile Arg Lys Asn
        255                 260                 265 taagagaata cctagaacat atcctcagca agaaacaaaa ccaaactgga ctctcgtgca       999
gaaaatgtag cccattacca catgtagcct tggagaccca ggcaaggaca agtacacgtg      1059
tactcacaga gggagagaaa gatgtgtaca aaggatatgt ataaatattc tatttagtca     1119
```
tccttaaaaa aaaaaaaaaa aaaaaaaaaa aa                           1151

<210> SEQ ID NO 4
<211> LENGTH: 269
<212> TYPE: PRT
<213> ORGANISM: Homo sapiens

<400> SEQUENCE: 4

Met Ala Ala Ser Ala Gly Ala Gly Ala Val Ile Ala Ala Pro Asp Ser
 1               5                  10                  15

Arg Arg Trp Leu Trp Ser Val Leu Ala Ala Leu Gly Ile Leu Thr
                20                  25                  30

Ala Gly Val Ser Ala Leu Glu Val Tyr Thr Pro Lys Glu Ile Phe Val
            35                  40                  45

Ala Asn Gly Thr Gln Gly Lys Leu Thr Cys Lys Phe Lys Ser Thr Ser
        50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp Tyr Thr Gly Cys Ser Thr Ser Glu Ser
        195                 200                 205

Leu Ser Pro Val Lys Gln Ala Pro Arg Lys Ser Pro Ser Asp Thr Glu
    210                 215                 220

Gly Leu Val Lys Ser Leu Pro Ser Gly Ser His Gln Gly Pro Val Ile
225                 230                 235                 240

Tyr Ala Gln Leu Asp His Ser Gly Gly His His Ser Asp Lys Ile Asn
                245                 250                 255

Lys Ser Glu Ser Val Val Tyr Ala Asp Ile Arg Lys Asn
            260                 265

<210> SEQ ID NO 5
<211> LENGTH: 1151
<212> TYPE: DNA
<213> ORGANISM: Homo sapiens
<220> FEATURE:
<221> NAME/KEY: gene
<222> LOCATION: (1)..(1151)
<220> FEATURE:
<221> NAME/KEY: CDS
<222> LOCATION: (133)..(939)

<400> SEQUENCE: 5
gcgcgggttg gaggtgccac ccggcgcggg tggcggagag atcagaagcc tcttccccaa    60
gccgagccaa cctcagcggg gacccgggct cagggacgcg gcggcggcgg cggcgactgc   120

```
agtggctgga cg atg gca gcg tcc gcc gga gcc ggg gcg gtg att gca gcc        171
              Met Ala Ala Ser Ala Gly Ala Gly Ala Val Ile Ala Ala
                1               5                  10 cca gac agc cgg cgc tgg ctg tgg tcg gtg ctg gcg gcg gcg ctt ggg          219
Pro Asp Ser Arg Arg Trp Leu Trp Ser Val Leu Ala Ala Ala Leu Gly
 15                  20                  25 atc ctg aca gct gga gta tca gcc ttg gaa gta tat acg cca aaa gaa          267
Ile Leu Thr Ala Gly Val Ser Ala Leu Glu Val Tyr Thr Pro Lys Glu
 30                  35                  40                  45 atc ttc gtg gca aat ggt aca caa ggg aag ctg acc tgc aag ttc aag          315
Ile Phe Val Ala Asn Gly Thr Gln Gly Lys Leu Thr Cys Lys Phe Lys
                 50                  55                  60 tct act agt acg act ggc ggg ttg acc tca gtc tcc tgg agc ttc cag          363
Ser Thr Ser Thr Thr Gly Gly Leu Thr Ser Val Ser Trp Ser Phe Gln
                 65                  70                  75 cca gag ggg gcc gac act act gtg tcg ttt ttc cac tac tcc caa ggg          411
Pro Glu Gly Ala Asp Thr Thr Val Ser Phe Phe His Tyr Ser Gln Gly
 80                  85                  90 caa gtg tac ctt ggg aat tat cca cca ttt aaa gac aga atc agc tgg          459
Gln Val Tyr Leu Gly Asn Tyr Pro Pro Phe Lys Asp Arg Ile Ser Trp
 95                 100                 105 gct gga gac ctt gac aag aaa gat gca tca atc aac ata gaa aat atg          507
Ala Gly Asp Leu Asp Lys Lys Asp Ala Ser Ile Asn Ile Glu Asn Met
110                 115                 120                 125 cag ttt ata cac aat ggc acc tat atc tgt gat gtc aaa aac cct cct          555
Gln Phe Ile His Asn Gly Thr Tyr Ile Cys Asp Val Lys Asn Pro Pro
                130                 135                 140 gac atc gtt gtc cag cct gga cac att agg ctc tat gtc gta gaa aaa          603
Asp Ile Val Val Gln Pro Gly His Ile Arg Leu Tyr Val Val Glu Lys
                145                 150                 155 gag aat ttg cct gtg ttt cca gtt tgg gta gtg gtg ggc ata gtt act          651
Glu Asn Leu Pro Val Phe Pro Val Trp Val Val Val Gly Ile Val Thr
                160                 165                 170 gct gtg gtc cta ggt ctc act ctg ctc atc agc atg att ctg gct gtc          699
Ala Val Val Leu Gly Leu Thr Leu Leu Ile Ser Met Ile Leu Ala Val
175                 180                 185 ctc tat aga agg aaa aac tct aaa cgg gat tac act ggc tgc agt aca          747
Leu Tyr Arg Arg Lys Asn Ser Lys Arg Asp Tyr Thr Gly Cys Ser Thr
190                 195                 200                 205 tca gag agt ttg tca cca gtt aag cag gct cct cgg aag tcc ccc tcc          795
Ser Glu Ser Leu Ser Pro Val Lys Gln Ala Pro Arg Lys Ser Pro Ser
                210                 215                 220 gac act gag ggt ctt gta aag agt ctg cct tct gga tct cac cag ggc          843
Asp Thr Glu Gly Leu Val Lys Ser Leu Pro Ser Gly Ser His Gln Gly
                225                 230                 235 cca gtc ata tat gca cag ata gac cac tcc ggc gga cat cac agt gac          891
Pro Val Ile Tyr Ala Gln Ile Asp His Ser Gly Gly His His Ser Asp
                240                 245                 250 aag att aac aag tca gag tct gtg gtg tat gcg gat atc cga aag aat          939
Lys Ile Asn Lys Ser Glu Ser Val Val Tyr Ala Asp Ile Arg Lys Asn
255                 260                 265 taagagaata cctagaacat atcctcagca agaaacaaaa ccaaactgga ctctcgtgca        999
gaaaatgtag cccattacca catgtagcct tggagaccca ggcaaggaca agtacacgtg       1059
tactcacaga gggagagaaa gatgtgtaca aaggatatgt ataaatattc tatttagtca       1119
tccttaaaaa aaaaaaaaaa aaaaaaaaaa aa                                     1151

<210> SEQ ID NO 6
<211> LENGTH: 269
```

<212> TYPE: PRT
<213> ORGANISM: Homo sapiens

<400> SEQUENCE: 6

Met Ala Ala Ser Ala Gly Ala Gly Ala Val Ile Ala Ala Pro Asp Ser
 1               5                  10                  15

Arg Arg Trp Leu Trp Ser Val Leu Ala Ala Leu Gly Ile Leu Thr
             20                  25                  30

Ala Gly Val Ser Ala Leu Glu Val Tyr Thr Pro Lys Glu Ile Phe Val
         35                  40                  45

Ala Asn Gly Thr Gln Gly Lys Leu Thr Cys Lys Phe Lys Ser Thr Ser
     50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
             85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp Tyr Thr Gly Cys Ser Thr Ser Glu Ser
        195                 200                 205

Leu Ser Pro Val Lys Gln Ala Pro Arg Lys Ser Pro Ser Asp Thr Glu
    210                 215                 220

Gly Leu Val Lys Ser Leu Pro Ser Gly Ser His Gln Gly Pro Val Ile
225                 230                 235                 240

Tyr Ala Gln Ile Asp His Ser Gly Gly His His Ser Asp Lys Ile Asn
                245                 250                 255

Lys Ser Glu Ser Val Val Tyr Ala Asp Ile Arg Lys Asn
            260                 265

<210> SEQ ID NO 7
<211> LENGTH: 1151
<212> TYPE: DNA
<213> ORGANISM: Homo sapiens
<220> FEATURE:
<221> NAME/KEY: gene
<222> LOCATION: (1)..(1151)
<220> FEATURE:
<221> NAME/KEY: CDS
<222> LOCATION: (133)..(939)

<400> SEQUENCE: 7
gcgcgggttg gaggtgccac ccggcgcggg tggcggagag atcagaagcc tcttccccaa      60
gccgagccaa cctcagcggg gacccgggct cagggacgcg gcggcggcgg cggcgactgc     120
agtggctgga cg atg gca gcg tcc gcc gga gcc ggg gcg gtg att gca gcc     171
            Met Ala Ala Ser Ala Gly Ala Gly Ala Val Ile Ala Ala
              1               5                  10 cca gac agc cgg cgc tgg ctg tgg tcg gtg ctg gcg gcg gcg ctt ggg     219

```
Pro Asp Ser Arg Arg Trp Leu Trp Ser Val Leu Ala Ala Ala Leu Gly
     15                  20                  25 atc ttg aca gct gga gta tca gcc ttg gaa gta tat acg cca aaa gaa    267
Ile Leu Thr Ala Gly Val Ser Ala Leu Glu Val Tyr Thr Pro Lys Glu
 30                  35                  40                  45 atc ttc gtg gca aat ggt aca caa ggg aag ctg acc tgc aag ttc aag    315
Ile Phe Val Ala Asn Gly Thr Gln Gly Lys Leu Thr Cys Lys Phe Lys
                 50                  55                  60 tct act agt acg act ggc ggg ttg acc tca gtc tcc tgg agc ttc cag    363
Ser Thr Ser Thr Thr Gly Gly Leu Thr Ser Val Ser Trp Ser Phe Gln
                     65                  70                  75 cca gag ggg gcc gac act act gtg tcg ttt ttc cac tac tcc caa ggg    411
Pro Glu Gly Ala Asp Thr Thr Val Ser Phe Phe His Tyr Ser Gln Gly
             80                  85                  90 caa gtg tac ctt ggg aat tat cca cca ttt aaa gac aga atc agc tgg    459
Gln Val Tyr Leu Gly Asn Tyr Pro Pro Phe Lys Asp Arg Ile Ser Trp
         95                 100                 105 gct gga gac ctt gac aag aaa gat gca tca atc aac ata gaa aat atg    507
Ala Gly Asp Leu Asp Lys Lys Asp Ala Ser Ile Asn Ile Glu Asn Met
110                 115                 120                 125 cag ttt ata cac aat ggc acc tat atc tgt gat gtc aaa aac cct cct    555
Gln Phe Ile His Asn Gly Thr Tyr Ile Cys Asp Val Lys Asn Pro Pro
                130                 135                 140 gac atc gtt gtc cag cct gga cac att agg ctc tat gtc gta gaa aaa    603
Asp Ile Val Val Gln Pro Gly His Ile Arg Leu Tyr Val Val Glu Lys
            145                 150                 155 gag aat ttg cct gtg ttt cca gtt tgg gta gtg gtg ggc ata gtt act    651
Glu Asn Leu Pro Val Phe Pro Val Trp Val Val Val Gly Ile Val Thr
        160                 165                 170 gct gtg gtc cta ggt ctc act ctg ctc atc agc atg att ctg gct gtc    699
Ala Val Val Leu Gly Leu Thr Leu Leu Ile Ser Met Ile Leu Ala Val
175                 180                 185 ctc tat aga agg aaa aac tct aaa cgg gat tac act ggc tgc agt aca    747
Leu Tyr Arg Arg Lys Asn Ser Lys Arg Asp Tyr Thr Gly Cys Ser Thr
190                 195                 200                 205 tca gag agt ttg tca cca gtt aag cag gct cct cgg aag tcc ccc tcc    795
Ser Glu Ser Leu Ser Pro Val Lys Gln Ala Pro Arg Lys Ser Pro Ser
                210                 215                 220 gac act gag ggt ctt gta aag agt ctg cct tct gga tct cac cag ggc    843
Asp Thr Glu Gly Leu Val Lys Ser Leu Pro Ser Gly Ser His Gln Gly
            225                 230                 235 cca gtc ata tat gca cag ata gac cac tcc ggc gga cat cac agt gac    891
Pro Val Ile Tyr Ala Gln Ile Asp His Ser Gly Gly His His Ser Asp
        240                 245                 250 aag att aac aag tca gag tct gtg gtg tat gcg gat atc cga aag aat    939
Lys Ile Asn Lys Ser Glu Ser Val Val Tyr Ala Asp Ile Arg Lys Asn
    255                 260                 265 taagagaata cctagaacat atcctcagca agaaacaaaa ccaaactgga ctctcgtgca   999
gaaaatgtag cccattacca catgtagcct tggagaccca ggcaaggaca agtacacgtg  1059
tactcacaga gggagagaaa gatgtgtaca aaggatatgt ataaatattc tatttagtca  1119
tccttaaaaa aaaaaaaaaa aaaaaaaaaa aa                                1151

<210> SEQ ID NO 8
<211> LENGTH: 269
<212> TYPE: PRT
<213> ORGANISM: Homo sapiens

<400> SEQUENCE: 8
```

Met Ala Ala Ser Ala Gly Ala Gly Ala Val Ile Ala Ala Pro Asp Ser
1               5                   10                  15

Arg Arg Trp Leu Trp Ser Val Leu Ala Ala Leu Gly Ile Leu Thr
            20                  25                  30

Ala Gly Val Ser Ala Leu Glu Val Tyr Thr Pro Lys Glu Ile Phe Val
            35                  40                  45

Ala Asn Gly Thr Gln Gly Lys Leu Thr Cys Lys Phe Lys Ser Thr Ser
        50                  55                  60

Thr Thr Gly Gly Leu Thr Ser Val Ser Trp Ser Phe Gln Pro Glu Gly
65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
                100                 105                 110

Leu Asp Lys Lys Asp Ala Ser Ile Asn Ile Glu Asn Met Gln Phe Ile
            115                 120                 125

His Asn Gly Thr Tyr Ile Cys Asp Val Lys Asn Pro Pro Asp Ile Val
130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp Tyr Thr Gly Cys Ser Thr Ser Glu Ser
        195                 200                 205

Leu Ser Pro Val Lys Gln Ala Pro Arg Lys Ser Pro Ser Asp Thr Glu
    210                 215                 220

Gly Leu Val Lys Ser Leu Pro Ser Gly Ser His Gln Gly Pro Val Ile
225                 230                 235                 240

Tyr Ala Gln Ile Asp His Ser Gly Gly His His Ser Asp Lys Ile Asn
                245                 250                 255

Lys Ser Glu Ser Val Val Tyr Ala Asp Ile Arg Lys Asn
                260                 265

<210> SEQ ID NO 9
<211> LENGTH: 26
<212> TYPE: DNA
<213> ORGANISM: Homo sapiens

<400> SEQUENCE: 9
tccgaggagc ctgcttaact ggtgac                                            26

<210> SEQ ID NO 10
<211> LENGTH: 26
<212> TYPE: DNA
<213> ORGANISM: Homo sapiens

<400> SEQUENCE: 10
gtagtggtgg gcatagttac tgctgt                                            26

<210> SEQ ID NO 11
<211> LENGTH: 24
<212> TYPE: DNA
<213> ORGANISM: Homo sapiens

<400> SEQUENCE: 11

```
gatggcagcg tccgccggag ccgg                                              24

<210> SEQ ID NO 12
<211> LENGTH: 27
<212> TYPE: DNA
<213> ORGANISM: Homo sapiens

<400> SEQUENCE: 12
ccagtttggt tttgtttctt gctgagg                                           27

<210> SEQ ID NO 13
<211> LENGTH: 16
<212> TYPE: PRT
<213> ORGANISM: Homo sapiens

<400> SEQUENCE: 13

Arg Asp Xaa Thr Gly Cys Ser Thr Ser Glu Ser Leu Ser Pro Val Lys
  1               5                  10                  15

<210> SEQ ID NO 14
<211> LENGTH: 26
<212> TYPE: PRT
<213> ORGANISM: Homo sapiens

<400> SEQUENCE: 14

Ser Leu Pro Ser Gly Ser His Gln Gly Pro Val Ile Tyr Ala Gln Leu
  1               5                  10                  15

Asp His Ser Gly Gly His His Ser Asp Lys
             20                  25

<210> SEQ ID NO 15
<211> LENGTH: 11
<212> TYPE: PRT
<213> ORGANISM: Homo sapiens

<400> SEQUENCE: 15

Asp Arg Ile Ser Trp Ala Gly Asp Leu Asp Lys
  1               5                  10

<210> SEQ ID NO 16
<211> LENGTH: 19
<212> TYPE: PRT
<213> ORGANISM: Homo sapiens

<400> SEQUENCE: 16

Asn Pro Pro Asp Ile Val Val Gln Pro Gly His Ile Arg Leu Tyr Val
  1               5                  10                  15

Val Glu Lys

<210> SEQ ID NO 17
<211> LENGTH: 752
<212> TYPE: DNA
<213> ORGANISM: Homo sapiens
<220> FEATURE:
<221> NAME/KEY: CDS
<222> LOCATION: (1)..(627)

<400> SEQUENCE: 17 atg gca gcg tcc gcc gga gcc ggg gcg gtg att gca gcc cca gac agc        48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg ctc ttg aca        96
Arg Arg Trp Leu Trp Ser Val Leu Ala Ala Ala Leu Gly Leu Leu Thr
             20                  25                  30
```

-continued

```
gct gga gta tca gcc ttg gaa gta tat acg cca aaa gaa atc ttc gtg    144
Ala Gly Val Ser Ala Leu Glu Val Tyr Thr Pro Lys Glu Ile Phe Val
            35                  40                  45 gca aat ggt aca caa ggg aag ctg acc tgc aag ttc aag tct act agt    192
Ala Asn Gly Thr Gln Gly Lys Leu Thr Cys Lys Phe Lys Ser Thr Ser
 50                  55                  60 acg act ggc ggg ttg acc tca gtc tcc tgg agc ttc cag cca gag ggg    240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac    288
Ala Asp Thr Thr Val Ser Phe Phe His Tyr Ser Gln Gly Gln Val Tyr
                 85                  90                  95 ctt ggg aat tat cca cca ttt aaa gac aga atc agc tgg gct gga gac    336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata    384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt    432
His Asn Gly Thr Tyr Ile Cys Asp Val Lys Asn Pro Pro Asp Ile Val
130                 135                 140 gtc cag cct gga cac att agg ctc tat gtc gta gaa aaa gag aat ttg    480
Val Gln Pro Gly His Ile Arg Leu Tyr Val Val Glu Lys Glu Asn Leu
145                 150                 155                 160 cct gtg ttt cca gtt tgg gta gtg gtg ggc ata gtt act gct gtg gtc    528
Pro Val Phe Pro Val Trp Val Val Val Gly Ile Val Thr Ala Val Val
                165                 170                 175 cta ggt ctc act ctg ctc atc agc atg att ctg gct gtc ctc tat aga    576
Leu Gly Leu Thr Leu Leu Ile Ser Met Ile Leu Ala Val Leu Tyr Arg
            180                 185                 190 agg aaa aac tct aaa cgg gat tac act ggg gcc cag tca tat atg cac    624
Arg Lys Asn Ser Lys Arg Asp Tyr Thr Gly Ala Gln Ser Tyr Met His
        195                 200                 205 agt tagaccactc cggcggacat cacagtgaca agattaacaa gtcagagtct         677
Ser gtggtgtatg cggatatccg aaagaattaa gagaatacct agaacatatc ctcagcaaga  737
aacaaaacca aactg                                                   752

<210> SEQ ID NO 18
<211> LENGTH: 209
<212> TYPE: PRT
<213> ORGANISM: Homo sapiens

<400> SEQUENCE: 18

Met Ala Ala Ser Ala Gly Ala Gly Ala Val Ile Ala Ala Pro Asp Ser
 1               5                  10                  15

Arg Arg Trp Leu Trp Ser Val Leu Ala Ala Ala Leu Gly Leu Leu Thr
            20                  25                  30

Ala Gly Val Ser Ala Leu Glu Val Tyr Thr Pro Lys Glu Ile Phe Val
        35                  40                  45

Ala Asn Gly Thr Gln Gly Lys Leu Thr Cys Lys Phe Lys Ser Thr Ser
 50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95

Leu Gly Asn Tyr Pro Pro Phe Lys Asp Arg Ile Ser Trp Ala Gly Asp
```

```
              100                 105                 110
Leu Asp Lys Lys Asp Ala Ser Ile Asn Ile Glu Asn Met Gln Phe Ile
            115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp Tyr Thr Gly Ala Gln Ser Tyr Met His
            195                 200                 205

Ser

<210> SEQ ID NO 19
<211> LENGTH: 752
<212> TYPE: DNA
<213> ORGANISM: Homo sapiens
<220> FEATURE:
<221> NAME/KEY: CDS
<222> LOCATION: (1)..(627)

<400> SEQUENCE: 19 atg gca gcg tcc gcc gga gcc ggg gcg gtg att gca gcc cca gac agc     48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg atc ttg aca     96
Arg Arg Trp Leu Trp Ser Val Leu Ala Ala Ala Leu Gly Ile Leu Thr
             20                  25                  30 gct gga gta tca gcc ttg gaa gta tat acg cca aaa gaa atc ttc gtg    144
Ala Gly Val Ser Ala Leu Glu Val Tyr Thr Pro Lys Glu Ile Phe Val
         35                  40                  45 gca aat ggt aca caa ggg aag ctg acc tgc aag ttc aag tct act agt    192
Ala Asn Gly Thr Gln Gly Lys Leu Thr Cys Lys Phe Lys Ser Thr Ser
     50                  55                  60 acg act ggc ggg ttg acc tca gtc tcc tgg agc ttc cag cca gag ggg    240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac    288
Ala Asp Thr Thr Val Ser Phe Phe His Tyr Ser Gln Gly Gln Val Tyr
                 85                  90                  95 ctt ggg aat tat cca cca ttt aaa gac aga atc agc tgg gct gga gac    336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata    384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt    432
His Asn Gly Thr Tyr Ile Cys Asp Val Lys Asn Pro Pro Asp Ile Val
    130                 135                 140 gtc cag cct gga cac att agg ctc tat gtc gta gaa aaa gag aat ttg    480
Val Gln Pro Gly His Ile Arg Leu Tyr Val Val Glu Lys Glu Asn Leu
145                 150                 155                 160 cct gtg ttt cca gtt tgg gta gtg gtg ggc ata gtt act gct gtg gtc    528
Pro Val Phe Pro Val Trp Val Val Gly Ile Val Thr Ala Val Val
                165                 170                 175 cta ggt ctc act ctg ctc atc agc atg att ctg gct gtc ctc tat aga    576
Leu Gly Leu Thr Leu Leu Ile Ser Met Ile Leu Ala Val Leu Tyr Arg
```

```
                      180                 185                 190
agg aaa aac tct aaa cgg gat tac act ggg gcc cag tca tat atg cac       624
Arg Lys Asn Ser Lys Arg Asp Tyr Thr Gly Ala Gln Ser Tyr Met His
            195                 200                 205 agt tagaccactc cggcggacat cacagtgaca agattaacaa gtcagagtct            677
Ser gtggtgtatg cggatatccg aaagaattaa gagaatacct agaacatatc ctcagcaaga     737
aacaaaacca aactg                                                      752

<210> SEQ ID NO 20
<211> LENGTH: 209
<212> TYPE: PRT
<213> ORGANISM: Homo sapiens

<400> SEQUENCE: 20

Met Ala Ala Ser Ala Gly Ala Gly Ala Val Ile Ala Ala Pro Asp Ser
 1               5                  10                  15

Arg Arg Trp Leu Trp Ser Val Leu Ala Ala Ala Leu Gly Ile Leu Thr
                20                  25                  30

Ala Gly Val Ser Ala Leu Glu Val Tyr Thr Pro Lys Glu Ile Phe Val
            35                  40                  45

Ala Asn Gly Thr Gln Gly Lys Leu Thr Cys Lys Phe Lys Ser Thr Ser
        50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
                100                 105                 110

Leu Asp Lys Lys Asp Ala Ser Ile Asn Ile Glu Asn Met Gln Phe Ile
            115                 120                 125

His Asn Gly Thr Tyr Ile Cys Asp Val Lys Asn Pro Pro Asp Ile Val
        130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
                180                 185                 190

Arg Lys Asn Ser Lys Arg Asp Tyr Thr Gly Ala Gln Ser Tyr Met His
            195                 200                 205

Ser

<210> SEQ ID NO 21
<211> LENGTH: 752
<212> TYPE: DNA
<213> ORGANISM: Homo sapiens
<220> FEATURE:
<221> NAME/KEY: CDS
<222> LOCATION: (1)..(627)

<400> SEQUENCE: 21 atg gca gcg tcc gcc gga gcc ggg gcg gtg att gca gcc cca gac agc       48
Met Ala Ala Ser Ala Gly Ala Gly Ala Val Ile Ala Ala Pro Asp Ser
 1               5                  10                  15 cgg cgc tgg ctg tgg tcg gtg ctg gcg gcg gcg ctt ggg ctc ttg aca       96
Arg Arg Trp Leu Trp Ser Val Leu Ala Ala Ala Leu Gly Leu Leu Thr
```

```
                  20                    25                    30
gct gga gta tca gcc ttg gaa gta tat acg cca aaa gaa atc ttc gtg        144
Ala Gly Val Ser Ala Leu Glu Val Tyr Thr Pro Lys Glu Ile Phe Val
             35                    40                    45 gca aat ggt aca caa ggg aag ctg acc tgc aag ttc aag tct act agt        192
Ala Asn Gly Thr Gln Gly Lys Leu Thr Cys Lys Phe Lys Ser Thr Ser
    50                    55                    60 acg act ggc ggg ttg acc tca gtc tcc tgg agc ttc cag cca gag ggg        240
Thr Thr Gly Gly Leu Thr Ser Val Ser Trp Ser Phe Gln Pro Glu Gly
 65                    70                    75                    80 gcc gac act act gtg tcg ttt ttc cac tac tcc caa ggg caa gtg tac        288
Ala Asp Thr Thr Val Ser Phe Phe His Tyr Ser Gln Gly Gln Val Tyr
                 85                    90                    95 ctt ggg aat tat cca cca ttt aaa gac aga atc agc tgg gct gga gac        336
Leu Gly Asn Tyr Pro Pro Phe Lys Asp Arg Ile Ser Trp Ala Gly Asp
             100                   105                   110 ctt gac aag aaa gat gca tca atc aac ata gaa aat atg cag ttt ata        384
Leu Asp Lys Lys Asp Ala Ser Ile Asn Ile Glu Asn Met Gln Phe Ile
        115                   120                   125 cac aat ggc acc tat atc tgt gat gtc aaa aac cct cct gac atc gtt        432
His Asn Gly Thr Tyr Ile Cys Asp Val Lys Asn Pro Pro Asp Ile Val
130                   135                   140 gtc cag cct gga cac att agg ctc tat gtc gta gaa aaa gag aat ttg        480
Val Gln Pro Gly His Ile Arg Leu Tyr Val Val Glu Lys Glu Asn Leu
145                   150                   155                   160 cct gtg ttt cca gtt tgg gta gtg gtg ggc ata gtt act gct gtg gtc        528
Pro Val Phe Pro Val Trp Val Val Val Gly Ile Val Thr Ala Val Val
                 165                   170                   175 cta ggt ctc act ctg ctc atc agc atg att ctg gct gtc atc tat aga        576
Leu Gly Leu Thr Leu Leu Ile Ser Met Ile Leu Ala Val Ile Tyr Arg
             180                   185                   190 agg aaa aac tct aaa cgg gat tac act ggg gcc cag tca tat atg cac        624
Arg Lys Asn Ser Lys Arg Asp Tyr Thr Gly Ala Gln Ser Tyr Met His
        195                   200                   205 agt tagaccactc cggcggacat cacagtgaca agattaacaa gtcagagtct             677
Ser gtggtgtatg cggatatccg aaagaattaa gagaatacct agaacatatc ctcagcaaga      737
aacaaaacca aactg                                                       752

<210> SEQ ID NO 22
<211> LENGTH: 209
<212> TYPE: PRT
<213> ORGANISM: Homo sapiens

<400> SEQUENCE: 22

Met Ala Ala Ser Ala Gly Ala Gly Ala Val Ile Ala Ala Pro Asp Ser
 1               5                  10                  15

Arg Arg Trp Leu Trp Ser Val Leu Ala Ala Leu Gly Leu Leu Thr
             20                  25                  30

Ala Gly Val Ser Ala Leu Glu Val Tyr Thr Pro Lys Glu Ile Phe Val
             35                  40                  45

Ala Asn Gly Thr Gln Gly Lys Leu Thr Cys Lys Phe Lys Ser Thr Ser
        50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95
```

```
Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Ile Tyr Arg
            180                 185                 190

Arg Lys Asn Ser Lys Arg Asp Tyr Thr Gly Ala Gln Ser Tyr Met His
            195                 200                 205

Ser
```

<210> SEQ ID NO 23
<211> LENGTH: 752
<212> TYPE: DNA
<213> ORGANISM: Homo sapiens
<220> FEATURE:
<221> NAME/KEY: CDS
<222> LOCATION: (1)..(627)

<400> SEQUENCE: 23

```
atg gca gcg tcc gcc gga gcc ggg gcg gtg att gca gcc cca gac agc        48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg atc ttg aca        96
Arg Arg Trp Leu Trp Ser Val Leu Ala Ala Ala Leu Gly Ile Leu Thr
             20                  25                  30 gct gga gta tca gcc ttg gaa gta tat acg cca aaa gaa atc ttc gtg       144
Ala Gly Val Ser Ala Leu Glu Val Tyr Thr Pro Lys Glu Ile Phe Val
         35                  40                  45 gca aat ggt aca caa ggg aag ctg acc tgc aag ttc aag tct act agt       192
Ala Asn Gly Thr Gln Gly Lys Leu Thr Cys Lys Phe Lys Ser Thr Ser
     50                  55                  60 acg act ggc ggg ttg acc tca gtc tcc tgg agc ttc cag cca gag ggg       240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac       288
Ala Asp Thr Thr Val Ser Phe Phe His Tyr Ser Gln Gly Gln Val Tyr
                 85                  90                  95 ctt ggg aat tat cca cca ttt aaa gac aga atc agc tgg gct gga gac       336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata       384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt       432
His Asn Gly Thr Tyr Ile Cys Asp Val Lys Asn Pro Pro Asp Ile Val
    130                 135                 140 gtc cag cct gga cac att agg ctc tat gtc gta gaa aaa gag aat ttg       480
Val Gln Pro Gly His Ile Arg Leu Tyr Val Val Glu Lys Glu Asn Leu
145                 150                 155                 160 cct gtg ttt cca gtt tgg gta gtg ggc ata gtt act gct gtg gtc           528
Pro Val Phe Pro Val Trp Val Val Gly Ile Val Thr Ala Val Val
                165                 170                 175 cta ggt ctc act ctg ctc atc agc atg att ctg gct gtc atc tat aga       576
```

| | | | | | | | | | | | | |
|---|---|---|---|---|---|---|---|---|---|---|---|---|
| Leu | Gly | Leu | Thr | Leu | Leu | Ile | Ser | Met | Ile | Leu | Ala | Val | Ile | Tyr | Arg |
| | | | 180 | | | | 185 | | | | 190 | |

```
agg aaa aac tct aaa cgg gat tac act ggg gcc cag tca tat atg cac      624
Arg Lys Asn Ser Lys Arg Asp Tyr Thr Gly Ala Gln Ser Tyr Met His
        195                 200                 205 agt tagaccactc cggcggacat cacagtgaca agattaacaa gtcagagtct           677
Ser gtggtgtatg cggatatccg aaagaattaa gagaatacct agaacatatc ctcagcaaga    737
aacaaaacca aactg                                                     752

<210> SEQ ID NO 24
<211> LENGTH: 209
<212> TYPE: PRT
<213> ORGANISM: Homo sapiens

<400> SEQUENCE: 24

Met Ala Ala Ser Ala Gly Ala Gly Ala Val Ile Ala Ala Pro Asp Ser
 1               5                  10                  15

Arg Arg Trp Leu Trp Ser Val Leu Ala Ala Leu Gly Ile Leu Thr
            20                  25                  30

Ala Gly Val Ser Ala Leu Glu Val Tyr Thr Pro Lys Glu Ile Phe Val
        35                  40                  45

Ala Asn Gly Thr Gln Gly Lys Leu Thr Cys Lys Phe Lys Ser Thr Ser
    50                  55                  60

Thr Thr Gly Gly Leu Thr Ser Val Ser Trp Ser Phe Gln Pro Glu Gly
65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Ile Tyr Arg
            180                 185                 190

Arg Lys Asn Ser Lys Arg Asp Tyr Thr Gly Ala Gln Ser Tyr Met His
        195                 200                 205

Ser

<210> SEQ ID NO 25
<211> LENGTH: 1073
<212> TYPE: DNA
<213> ORGANISM: Mus sp.
<220> FEATURE:
<221> NAME/KEY: CDS
<222> LOCATION: (128)..(937)

<400> SEQUENCE: 25
ggagcgggga gcggtggcgt ggaggtgtcc tcgcgctcgc agccgcgatc cggacagagc    60
tgtgtggtct aaggcaagcc agccgaccgc agcgggaacc cggcggaac ggagcggcgg    120 agcagg atg gca gag gcc gtc gga gcc gtg gca ctg att gcg gcc ccg      169
```

```
            Met Ala Glu Ala Val Gly Ala Val Ala Leu Ile Ala Ala Pro
              1               5                  10 cc cgc cgg cgc tgg ctg tgg tcg gtg cta gcc gcg atg ctc ggg ctg         217
Ala Arg Arg Arg Trp Leu Trp Ser Val Leu Ala Ala Met Leu Gly Leu
 15                  20                  25                  30 tg aca gct aga ata tca gcc ttg gag gtc cat act cct aaa gaa atc         265
Leu Thr Ala Arg Ile Ser Ala Leu Glu Val His Thr Pro Lys Glu Ile
             35                  40                  45 tt gtg gtg aat ggg aca caa ggg aag ctg act tgc aca ttc gat tct         313
Phe Val Val Asn Gly Thr Gln Gly Lys Leu Thr Cys Thr Phe Asp Ser
         50                  55                  60 ct aac aca act gga tgg ttg acc acg gtc tcc tgg agc ttc cag cca         361
Pro Asn Thr Thr Gly Trp Leu Thr Thr Val Ser Trp Ser Phe Gln Pro
     65                  70                  75 ac ggc acc gac agc gcc gtg tcg ttt ttc cac tac tca caa gga cag         409
Asp Gly Thr Asp Ser Ala Val Ser Phe Phe His Tyr Ser Gln Gly Gln
 80                  85                  90 tg tac att ggg gat tat cca cca ttt aaa gac cga gtc acc tgg gct         457
Val Tyr Ile Gly Asp Tyr Pro Pro Phe Lys Asp Arg Val Thr Trp Ala
 95                 100                 105                 110 gg gac ctt gac aag aaa gat gca tca atc aat ata gaa aat att cag         505
Gly Asp Leu Asp Lys Lys Asp Ala Ser Ile Asn Ile Glu Asn Ile Gln
                 115                 120                 125 ct gtt cac aat ggc acc tat atc tgc gat gtc aaa aat cct cct gac         553
Ala Val His Asn Gly Thr Tyr Ile Cys Asp Val Lys Asn Pro Pro Asp
             130                 135                 140 tt gtt gtg cgg cct gga cac att agg ctc cac gtg gtg gaa ata gac         601
Ile Val Val Arg Pro Gly His Ile Arg Leu His Val Val Glu Ile Asp
         145                 150                 155 ac ctg ttg gtg ttc ctg gtt tgg gtg gtg gtg ggc act gtc act gct         649
Asn Leu Leu Val Phe Leu Val Trp Val Val Val Gly Thr Val Thr Ala
     160                 165                 170 tg gtc ctt ggc ctc act ctg ctt atc agc ttg gtc ctg gtc gtc ctc         697
Val Val Leu Gly Leu Thr Leu Leu Ile Ser Leu Val Leu Val Val Leu
175                 180                 185                 190 ac aga agg aaa cat tcg aag cgg gat tat acc ggc tgc agt acc tca         745
Tyr Arg Arg Lys His Ser Lys Arg Asp Tyr Thr Gly Cys Ser Thr Ser
                 195                 200                 205 ag cgt ttg tca cca gtt aag cag gct cca cgg aag tgt ccc tcc gac         793
Glu Arg Leu Ser Pro Val Lys Gln Ala Pro Arg Lys Cys Pro Ser Asp
             210                 215                 220 ca gag ggt cta gta aag agt ccg cct tcc gcc gga tct cac cag ggc         841
Thr Glu Gly Leu Val Lys Ser Pro Pro Ser Ala Gly Ser His Gln Gly
         225                 230                 235 ca gtc att tac gca cag tta gac cac tct gac gga cac cac agc ggc         889
Pro Val Ile Tyr Ala Gln Leu Asp His Ser Asp Gly His His Ser Gly
     240                 245                 250 ag att aat aag tca gag tcg gtt gtg tat gcg gac atc cgg aaa gac         937
Lys Ile Asn Lys Ser Glu Ser Val Val Tyr Ala Asp Ile Arg Lys Asp
255                 260                 265                 270 aagagaaca cccaaacatt tccaaactgg acgcttgtgc agaaaatgtc cataacccgc       997
atgtggcctt gaggactcgg gcaaggacaa gcacatgtat actcggagag agcagaaaat    1057
atgtatagag gatatg                                                    1073

<210> SEQ ID NO 26
<211> LENGTH: 270
<212> TYPE: PRT
<213> ORGANISM: Mus sp.
```

```
<400> SEQUENCE: 26

Met Ala Glu Ala Val Gly Ala Val Ala Leu Ile Ala Ala Pro Ala Arg
  1               5                  10                  15

Arg Arg Trp Leu Trp Ser Val Leu Ala Ala Met Leu Gly Leu Leu Thr
             20                  25                  30

Ala Arg Ile Ser Ala Leu Glu Val His Thr Pro Lys Glu Ile Phe Val
         35                  40                  45

Val Asn Gly Thr Gln Gly Lys Leu Thr Cys Thr Phe Asp Ser Pro Asn
     50                  55                  60

Thr Thr Gly Trp Leu Thr Thr Val Ser Trp Ser Phe Gln Pro Asp Gly
 65                  70                  75                  80

Thr Asp Ser Ala Val Ser Phe Phe His Tyr Ser Gln Gly Gln Val Tyr
                 85                  90                  95

Ile Gly Asp Tyr Pro Pro Phe Lys Asp Arg Val Thr Trp Ala Gly Asp
            100                 105                 110

Leu Asp Lys Lys Asp Ala Ser Ile Asn Ile Glu Asn Ile Gln Ala Val
        115                 120                 125

His Asn Gly Thr Tyr Ile Cys Asp Val Lys Asn Pro Pro Asp Ile Val
    130                 135                 140

Val Arg Pro Gly His Ile Arg Leu His Val Val Glu Ile Asp Asn Leu
145                 150                 155                 160

Leu Val Phe Leu Val Trp Val Val Gly Thr Val Thr Ala Val Val
                165                 170                 175

Leu Gly Leu Thr Leu Leu Ile Ser Leu Val Leu Val Leu Tyr Arg
                180                 185                 190

Arg Lys His Ser Lys Arg Asp Tyr Thr Gly Cys Ser Thr Ser Glu Arg
        195                 200                 205

Leu Ser Pro Val Lys Gln Ala Pro Arg Lys Cys Pro Ser Asp Thr Glu
    210                 215                 220

Gly Leu Val Lys Ser Pro Pro Ser Ala Gly Ser His Gln Gly Pro Val
225                 230                 235                 240

Ile Tyr Ala Gln Leu Asp His Ser Asp Gly His His Ser Gly Lys Ile
                245                 250                 255

Asn Lys Ser Glu Ser Val Val Tyr Ala Asp Ile Arg Lys Asp
            260                 265                 270

<210> SEQ ID NO 27
<211> LENGTH: 1073
<212> TYPE: DNA
<213> ORGANISM: Mus sp.
<220> FEATURE:
<221> NAME/KEY: CDS
<222> LOCATION: (128)..(937)

<400> SEQUENCE: 27
ggagcgggga gcggtggcgt ggaggtgtcc tcgcgctcgc agccgcgatc cggacagagc     60
tgtgtggtct aaggcaagcc agccgaccgc agcgggaacc cgggcggaac ggagcggcgg    120 gagcagg atg gca gag gcc gtc gga gcc gtg gca ctg att gcg gcc ccg      169
        Met Ala Glu Ala Val Gly Ala Val Ala Leu Ile Ala Ala Pro
          1               5                  10 gcc cgc cgg cgc tgg ctg tgg tcg gtg ata gcc gcg atg ctc ggg ctg      217
Ala Arg Arg Arg Trp Leu Trp Ser Val Ile Ala Ala Met Leu Gly Leu
 15                  20                  25                  30 ttg aca gct aga ata tca gcc ttg gag gtc cat act cct aaa gaa atc      265
Leu Thr Ala Arg Ile Ser Ala Leu Glu Val His Thr Pro Lys Glu Ile
             35                  40                  45
```

-continued

```
ttt gtg gtg aat ggg aca caa ggg aag ctg act tgc aca ttc gat tct      313
Phe Val Val Asn Gly Thr Gln Gly Lys Leu Thr Cys Thr Phe Asp Ser
             50                  55                  60 cct aac aca act gga tgg ttg acc acg gtc tcc tgg agc ttc cag cca      361
Pro Asn Thr Thr Gly Trp Leu Thr Thr Val Ser Trp Ser Phe Gln Pro
         65                  70                  75 gac ggc acc gac agc gcc gtg tcg ttt ttc cac tac tca caa gga cag      409
Asp Gly Thr Asp Ser Ala Val Ser Phe Phe His Tyr Ser Gln Gly Gln
     80                  85                  90 gtg tac att ggg gat tat cca cca ttt aaa gac cga gtc acc tgg gct      457
Val Tyr Ile Gly Asp Tyr Pro Pro Phe Lys Asp Arg Val Thr Trp Ala
 95                 100                 105                 110 ggg gac ctt gac aag aaa gat gca tca atc aat ata gaa aat att cag      505
Gly Asp Leu Asp Lys Lys Asp Ala Ser Ile Asn Ile Glu Asn Ile Gln
                115                 120                 125 gct gtt cac aat ggc acc tat atc tgc gat gtc aaa aat cct cct gac      553
Ala Val His Asn Gly Thr Tyr Ile Cys Asp Val Lys Asn Pro Pro Asp
            130                 135                 140 att gtt gtg cgg cct gga cac att agg ctc cac gtg gtg gaa ata gac      601
Ile Val Val Arg Pro Gly His Ile Arg Leu His Val Val Glu Ile Asp
        145                 150                 155 aac ctg ttg gtg ttc ctg gtt tgg gtg gtg gtg ggc act gtc act gct      649
Asn Leu Leu Val Phe Leu Val Trp Val Val Val Gly Thr Val Thr Ala
    160                 165                 170 gtg gtc ctt ggc ctc act ctg ctt atc agc ttg gtc ctg gtc gtc ctc      697
Val Val Leu Gly Leu Thr Leu Leu Ile Ser Leu Val Leu Val Val Leu
175                 180                 185                 190 tac aga agg aaa cat tcg aag cgg gat tat acc ggc tgc agt acc tca      745
Tyr Arg Arg Lys His Ser Lys Arg Asp Tyr Thr Gly Cys Ser Thr Ser
                195                 200                 205 gag cgt ttg tca cca gtt aag cag gct cca cgg aag tgt ccc tcc gac      793
Glu Arg Leu Ser Pro Val Lys Gln Ala Pro Arg Lys Cys Pro Ser Asp
            210                 215                 220 aca gag ggt cta gta aag agt ccg cct tcc gcc gga tct cac cag ggc      841
Thr Glu Gly Leu Val Lys Ser Pro Pro Ser Ala Gly Ser His Gln Gly
        225                 230                 235 cca gtc att tac gca cag tta gac cac tct gac gga cac cac agc ggc      889
Pro Val Ile Tyr Ala Gln Leu Asp His Ser Asp Gly His His Ser Gly
    240                 245                 250 aag att aat aag tca gag tcg gtt gtg tat gcg gac atc cgg aaa gac      937
Lys Ile Asn Lys Ser Glu Ser Val Val Tyr Ala Asp Ile Arg Lys Asp
255                 260                 265                 270 taagagaaca cccaaacatt tccaaactgg acgcttgtgc agaaaatgtc cataacccgc    997
atgtggcctt gaggactcgg gcaaggacaa gcacatgtat actcggagag agcagaaaat   1057
atgtatagag gatatg                                                   1073
```

<210> SEQ ID NO 28
<211> LENGTH: 270
<212> TYPE: PRT
<213> ORGANISM: Mus sp.

<400> SEQUENCE: 28

```
Met Ala Glu Ala Val Gly Ala Val Ala Leu Ile Ala Ala Pro Ala Arg
 1               5                  10                  15

Arg Arg Trp Leu Trp Ser Val Ile Ala Ala Met Leu Gly Leu Leu Thr
                20                  25                  30

Ala Arg Ile Ser Ala Leu Glu Val His Thr Pro Lys Glu Ile Phe Val
            35                  40                  45
```

```
Val Asn Gly Thr Gln Gly Lys Leu Thr Cys Thr Phe Asp Ser Pro Asn
 50                  55                  60

Thr Thr Gly Trp Leu Thr Thr Val Ser Trp Ser Phe Gln Pro Asp Gly
 65                  70                  75                  80

Thr Asp Ser Ala Val Ser Phe Phe His Tyr Ser Gln Gly Gln Val Tyr
                 85                  90                  95

Ile Gly Asp Tyr Pro Pro Phe Lys Asp Arg Val Thr Trp Ala Gly Asp
            100                 105                 110

Leu Asp Lys Lys Asp Ala Ser Ile Asn Ile Glu Asn Ile Gln Ala Val
        115                 120                 125

His Asn Gly Thr Tyr Ile Cys Asp Val Lys Asn Pro Pro Asp Ile Val
    130                 135                 140

Val Arg Pro Gly His Ile Arg Leu His Val Val Glu Ile Asp Asn Leu
145                 150                 155                 160

Leu Val Phe Leu Val Trp Val Val Gly Thr Val Thr Ala Val Val
                165                 170                 175

Leu Gly Leu Thr Leu Leu Ile Ser Leu Val Leu Val Val Leu Tyr Arg
            180                 185                 190

Arg Lys His Ser Lys Arg Asp Tyr Thr Gly Cys Ser Thr Ser Glu Arg
        195                 200                 205

Leu Ser Pro Val Lys Gln Ala Pro Arg Lys Cys Pro Ser Asp Thr Glu
    210                 215                 220

Gly Leu Val Lys Ser Pro Ser Ala Gly Ser His Gln Gly Pro Val
225                 230                 235                 240

Ile Tyr Ala Gln Leu Asp His Ser Asp Gly His His Ser Gly Lys Ile
            245                 250                 255

Asn Lys Ser Glu Ser Val Val Tyr Ala Asp Ile Arg Lys Asp
        260                 265                 270

<210> SEQ ID NO 29
<211> LENGTH: 1073
<212> TYPE: DNA
<213> ORGANISM: Mus sp.
<220> FEATURE:
<221> NAME/KEY: CDS
<222> LOCATION: (128)..(937)

<400> SEQUENCE: 29
ggagcgggga gcggtggcgt ggaggtgtcc tcgcgctcgc agccgcgatc cggacagagc     60
tgtgtggtct aaggcaagcc agccgaccgc agcgggaacc cgggcggaac ggagcggcgg    120 gagcagg atg gca gag gcc gtc gga gcc gtg gca ctg att gcg gcc ccg      169
        Met Ala Glu Ala Val Gly Ala Val Ala Leu Ile Ala Ala Pro
          1               5                  10 gcc cgc cgg cgc tgg ctg tgg tcg gtc cta gcc gcg atg ctc ggg ctg      217
Ala Arg Arg Arg Trp Leu Trp Ser Val Leu Ala Ala Met Leu Gly Leu
 15                  20                  25                  30 ttg aca gct aga ata tca gcc ttg gag gtc cat act cct aaa gaa atc      265
Leu Thr Ala Arg Ile Ser Ala Leu Glu Val His Thr Pro Lys Glu Ile
                 35                  40                  45 ttt gtg gtg aat ggg aca caa ggg aag ctg act tgc aca ttc gat tct      313
Phe Val Val Asn Gly Thr Gln Gly Lys Leu Thr Cys Thr Phe Asp Ser
             50                  55                  60 cct aac aca act gga tgg ttg acc acg gtc tcc tgg agc ttc cag cca      361
Pro Asn Thr Thr Gly Trp Leu Thr Thr Val Ser Trp Ser Phe Gln Pro
 65                  70                  75 gac ggc acc gac agc gcc gtg tcg ttt ttc cac tac tca caa gga cag      409
```

-continued

```
                Asp Gly Thr Asp Ser Ala Val Ser Phe Phe His Tyr Ser Gln Gly Gln
                     80                  85                  90 gtg tac att ggg gat tat cca cca ttt aaa gac cga gtc acc tgg gct              457
Val Tyr Ile Gly Asp Tyr Pro Pro Phe Lys Asp Arg Val Thr Trp Ala
 95                 100                 105                 110 ggg gac ctt gac aag aaa gat gca tca atc aat ata gaa aat att cag              505
Gly Asp Leu Asp Lys Lys Asp Ala Ser Ile Asn Ile Glu Asn Ile Gln
                115                 120                 125 gct gtt cac aat ggc acc tat atc tgc gat gtc aaa aat cct cct gac              553
Ala Val His Asn Gly Thr Tyr Ile Cys Asp Val Lys Asn Pro Pro Asp
            130                 135                 140 att gtt gtg cgg cct gga cac att agg ctc cac gtg gtg gaa ata gac              601
Ile Val Val Arg Pro Gly His Ile Arg Leu His Val Val Glu Ile Asp
        145                 150                 155 aac ctg ttg gtg ttc ctg gtt tgg gtg gtg gtg ggc act gtc act gct              649
Asn Leu Leu Val Phe Leu Val Trp Val Val Val Gly Thr Val Thr Ala
    160                 165                 170 gtg gtc ctt ggc ctc act ctg ctt atc agc ttg gtc ctg gtc gtc ctc              697
Val Val Leu Gly Leu Thr Leu Leu Ile Ser Leu Val Leu Val Val Leu
175                 180                 185                 190 tac aga agg aaa cat tcg aag cgg gat tat acc ggc tgc agt acc tca              745
Tyr Arg Arg Lys His Ser Lys Arg Asp Tyr Thr Gly Cys Ser Thr Ser
                195                 200                 205 gag cgt ttg tca cca gtt aag cag gct cca cgg aag tgt ccc tcc gac              793
Glu Arg Leu Ser Pro Val Lys Gln Ala Pro Arg Lys Cys Pro Ser Asp
            210                 215                 220 aca gag ggt cta gta aag agt ccg cct tcc gcc gga tct cac cag ggc              841
Thr Glu Gly Leu Val Lys Ser Pro Pro Ser Ala Gly Ser His Gln Gly
        225                 230                 235 cca gtc att tac gca cag ata gac cac tct gac gga cac cac agc ggc              889
Pro Val Ile Tyr Ala Gln Ile Asp His Ser Asp Gly His His Ser Gly
    240                 245                 250 aag att aat aag tca gag tcg gtt gtg tat gcg gac atc cgg aaa gac              937
Lys Ile Asn Lys Ser Glu Ser Val Val Tyr Ala Asp Ile Arg Lys Asp
255                 260                 265                 270 taagagaaca cccaaacatt tccaaactgg acgcttgtgc agaaaatgtc cataacccgc            997
atgtggcctt gaggactcgg gcaaggacaa gcacatgtat actcggagag agcagaaaat           1057
atgtatagag gatatg                                                           1073
```

<210> SEQ ID NO 30
<211> LENGTH: 270
<212> TYPE: PRT
<213> ORGANISM: Mus sp.

<400> SEQUENCE: 30

```
Met Ala Glu Ala Val Gly Ala Val Ala Leu Ile Ala Ala Pro Ala Arg
 1               5                  10                  15

Arg Arg Trp Leu Trp Ser Val Leu Ala Ala Met Leu Gly Leu Leu Thr
                20                  25                  30

Ala Arg Ile Ser Ala Leu Glu Val His Thr Pro Lys Glu Ile Phe Val
            35                  40                  45

Val Asn Gly Thr Gln Gly Lys Leu Thr Cys Thr Phe Asp Ser Pro Asn
        50                  55                  60

Thr Thr Gly Trp Leu Thr Thr Val Ser Trp Ser Phe Gln Pro Asp Gly
 65                 70                  75                  80

Thr Asp Ser Ala Val Ser Phe Phe His Tyr Ser Gln Gly Gln Val Tyr
                85                  90                  95
```

-continued

```
Ile Gly Asp Tyr Pro Pro Phe Lys Asp Arg Val Thr Trp Ala Gly Asp
            100                 105                 110

Leu Asp Lys Lys Asp Ala Ser Ile Asn Ile Glu Asn Ile Gln Ala Val
        115                 120                 125

His Asn Gly Thr Tyr Ile Cys Asp Val Lys Asn Pro Pro Asp Ile Val
    130                 135                 140

Val Arg Pro Gly His Ile Arg Leu His Val Val Glu Ile Asp Asn Leu
145                 150                 155                 160

Leu Val Phe Leu Val Trp Val Val Gly Thr Val Thr Ala Val Val
                165                 170                 175

Leu Gly Leu Thr Leu Leu Ile Ser Leu Val Leu Val Leu Tyr Arg
            180                 185                 190

Arg Lys His Ser Lys Arg Asp Tyr Thr Gly Cys Ser Thr Ser Glu Arg
        195                 200                 205

Leu Ser Pro Val Lys Gln Ala Pro Arg Lys Cys Pro Ser Asp Thr Glu
    210                 215                 220

Gly Leu Val Lys Ser Pro Pro Ser Ala Gly Ser His Gln Gly Pro Val
225                 230                 235                 240

Ile Tyr Ala Gln Ile Asp His Ser Asp Gly His His Ser Gly Lys Ile
                245                 250                 255

Asn Lys Ser Glu Ser Val Val Tyr Ala Asp Ile Arg Lys Asp
            260                 265                 270

<210> SEQ ID NO 31
<211> LENGTH: 1073
<212> TYPE: DNA
<213> ORGANISM: Mus sp.
<220> FEATURE:
<221> NAME/KEY: CDS
<222> LOCATION: (128)..(937)

<400> SEQUENCE: 31
ggagcgggga gcggtggcgt ggaggtgtcc tcgcgctcgc agccgcgatc cggacagagc      60
tgtgtggtct aaggcaagcc agccgaccgc agcgggaacc cgggcggaac ggagcggcgg     120 gagcagg atg gca gag gcc gtc gga gcc gtg gca ctg att gcg gcc ccg        169
        Met Ala Glu Ala Val Gly Ala Val Ala Leu Ile Ala Ala Pro
          1               5                  10 gcc cgc cgg cgc tgg ctg tgg tcg gtg ata gcc gcg atg ctc ggg ctg        217
Ala Arg Arg Arg Trp Leu Trp Ser Val Ile Ala Ala Met Leu Gly Leu
 15                  20                  25                  30 ttg aca gct aga ata tca gcc ttg gag gtc cat act cct aaa gaa atc        265
Leu Thr Ala Arg Ile Ser Ala Leu Glu Val His Thr Pro Lys Glu Ile
                 35                  40                  45 ttt gtg gtg aat ggg aca caa ggg aag ctg act tgc aca ttc gat tct        313
Phe Val Val Asn Gly Thr Gln Gly Lys Leu Thr Cys Thr Phe Asp Ser
             50                  55                  60 cct aac aca act gga tgg ttg acc acg gtc tcc tgg agc ttc cag cca        361
Pro Asn Thr Thr Gly Trp Leu Thr Thr Val Ser Trp Ser Phe Gln Pro
         65                  70                  75 gac ggc acc gac agc gcc gtg tcg ttt ttc cac tac tca caa gga cag        409
Asp Gly Thr Asp Ser Ala Val Ser Phe Phe His Tyr Ser Gln Gly Gln
     80                  85                  90 gtg tac att ggg gat tat cca cca ttt aaa gac cga gtc acc tgg gct        457
Val Tyr Ile Gly Asp Tyr Pro Pro Phe Lys Asp Arg Val Thr Trp Ala
 95                 100                 105                 110 ggg gac ctt gac aag aaa gat gca tca atc aat ata gaa aat att cag        505
Gly Asp Leu Asp Lys Lys Asp Ala Ser Ile Asn Ile Glu Asn Ile Gln
                115                 120                 125
```

```
gct gtt cac aat ggc acc tat atc tgc gat gtc aaa aat cct cct gac      553
Ala Val His Asn Gly Thr Tyr Ile Cys Asp Val Lys Asn Pro Pro Asp
            130                 135                 140 att gtt gtg cgg cct gga cac att agg ctc cac gtg gtg gaa ata gac      601
Ile Val Val Arg Pro Gly His Ile Arg Leu His Val Val Glu Ile Asp
        145                 150                 155 aac ctg ttg gtg ttc ctg gtt tgg gtg gtg gtg ggc act gtc act gct      649
Asn Leu Leu Val Phe Leu Val Trp Val Val Val Gly Thr Val Thr Ala
    160                 165                 170 gtg gtc ctt ggc ctc act ctg ctt atc agc ttg gtc ctg gtc gtc ctc      697
Val Val Leu Gly Leu Thr Leu Leu Ile Ser Leu Val Leu Val Val Leu
175                 180                 185                 190 tac aga agg aaa cat tcg aag cgg gat tat acc ggc tgc agt acc tca      745
Tyr Arg Arg Lys His Ser Lys Arg Asp Tyr Thr Gly Cys Ser Thr Ser
                195                 200                 205 gag cgt ttg tca cca gtt aag cag gct cca cgg aag tgt ccc tcc gac      793
Glu Arg Leu Ser Pro Val Lys Gln Ala Pro Arg Lys Cys Pro Ser Asp
            210                 215                 220 aca gag ggt cta gta aag agt ccg cct tcc gcc gga tct cac cag ggc      841
Thr Glu Gly Leu Val Lys Ser Pro Pro Ser Ala Gly Ser His Gln Gly
        225                 230                 235 cca gtc att tac gca cag ata gac cac tct gac gga cac cac agc ggc      889
Pro Val Ile Tyr Ala Gln Ile Asp His Ser Asp Gly His His Ser Gly
    240                 245                 250 aag att aat aag tca gag tcg gtt gtg tat gcg gac atc cgg aaa gac      937
Lys Ile Asn Lys Ser Glu Ser Val Val Tyr Ala Asp Ile Arg Lys Asp
255                 260                 265                 270 taagagaaca cccaaacatt tccaaactgg acgcttgtgc agaaaatgtc cataaccccgc   997 atgtggcctt gaggactcgg gcaaggacaa gcacatgtat actcggagag agcagaaaat  1057
atgtatagag gatatg                                                  1073

<210> SEQ ID NO 32
<211> LENGTH: 270
<212> TYPE: PRT
<213> ORGANISM: Mus sp.

<400> SEQUENCE: 32

Met Ala Glu Ala Val Gly Ala Val Ala Leu Ile Ala Ala Pro Ala Arg
 1               5                  10                  15

Arg Arg Trp Leu Trp Ser Val Ile Ala Ala Met Leu Gly Leu Leu Thr
            20                  25                  30

Ala Arg Ile Ser Ala Leu Glu Val His Thr Pro Lys Glu Ile Phe Val
        35                  40                  45

Val Asn Gly Thr Gln Gly Lys Leu Thr Cys Thr Phe Asp Ser Pro Asn
    50                  55                  60

Thr Thr Gly Trp Leu Thr Thr Val Ser Trp Ser Phe Gln Pro Asp Gly
65                  70                  75                  80

Thr Asp Ser Ala Val Ser Phe Phe His Tyr Ser Gln Gly Gln Val Tyr
                85                  90                  95

Ile Gly Asp Tyr Pro Pro Phe Lys Asp Arg Val Thr Trp Ala Gly Asp
            100                 105                 110

Leu Asp Lys Lys Asp Ala Ser Ile Asn Ile Glu Asn Ile Gln Ala Val
        115                 120                 125

His Asn Gly Thr Tyr Ile Cys Asp Val Lys Asn Pro Pro Asp Ile Val
    130                 135                 140

Val Arg Pro Gly His Ile Arg Leu His Val Val Glu Ile Asp Asn Leu
```

```
145                 150                 155                 160
Leu Val Phe Leu Val Trp Val Val Gly Thr Val Ala Val Val
                165                 170                 175

Leu Gly Leu Thr Leu Leu Ile Ser Leu Val Leu Val Leu Tyr Arg
        180                 185                 190

Arg Lys His Ser Lys Arg Asp Tyr Thr Gly Cys Ser Thr Ser Glu Arg
            195                 200                 205

Leu Ser Pro Val Lys Gln Ala Pro Arg Lys Cys Pro Ser Asp Thr Glu
        210                 215                 220

Gly Leu Val Lys Ser Pro Pro Ser Ala Gly Ser His Gln Gly Pro Val
225                 230                 235                 240

Ile Tyr Ala Gln Ile Asp His Ser Asp Gly His His Ser Gly Lys Ile
            245                 250                 255

Asn Lys Ser Glu Ser Val Val Tyr Ala Asp Ile Arg Lys Asp
            260                 265                 270

<210> SEQ ID NO 33
<211> LENGTH: 480
<212> TYPE: DNA
<213> ORGANISM: Homo sapiens
<220> FEATURE:
<221> NAME/KEY: CDS
<222> LOCATION: (1)..(477)

<400> SEQUENCE: 33 atg gca gcg tcc gcc gga gcc ggg gcg gtg att gca gcc cca gac agc      48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg ctc ttg aca      96
Arg Arg Trp Leu Trp Ser Val Leu Ala Ala Ala Leu Gly Leu Leu Thr
             20                  25                  30 gct gga gta tca gcc ttg gaa gta tat acg cca aaa gaa atc ttc gtg     144
Ala Gly Val Ser Ala Leu Glu Val Tyr Thr Pro Lys Glu Ile Phe Val
         35                  40                  45 gca aat ggt aca caa ggg aag ctg acc tgc aag ttc aag tct act agt     192
Ala Asn Gly Thr Gln Gly Lys Leu Thr Cys Lys Phe Lys Ser Thr Ser
     50                  55                  60 acg act ggc ggg ttg acc tca gtc tcc tgg agc ttc cag cca gag ggg     240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac     288
Ala Asp Thr Thr Val Ser Phe Phe His Tyr Ser Gln Gly Gln Val Tyr
                 85                  90                  95 ctt ggg aat tat cca cca ttt aaa gac aga atc agc tgg gct gga gac     336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata     384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt     432
His Asn Gly Thr Tyr Ile Cys Asp Val Lys Asn Pro Pro Asp Ile Val
    130                 135                 140 gtc cag cct gga cac att agg ctc tat gtc gta gaa aaa gag aat tag     480
Val Gln Pro Gly His Ile Arg Leu Tyr Val Val Glu Lys Glu Asn
145                 150                 155

<210> SEQ ID NO 34
<211> LENGTH: 159
<212> TYPE: PRT
<213> ORGANISM: Homo sapiens
```

```
<400> SEQUENCE: 34

Met Ala Ala Ser Ala Gly Ala Gly Ala Val Ile Ala Ala Pro Asp Ser
1               5                   10                  15

Arg Arg Trp Leu Trp Ser Val Leu Ala Ala Ala Leu Gly Leu Leu Thr
            20                  25                  30

Ala Gly Val Ser Ala Leu Glu Val Tyr Thr Pro Lys Glu Ile Phe Val
        35                  40                  45

Ala Asn Gly Thr Gln Gly Lys Leu Thr Cys Lys Phe Lys Ser Thr Ser
    50                  55                  60

Thr Thr Gly Gly Leu Thr Ser Val Ser Trp Ser Phe Gln Pro Glu Gly
65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn
145                 150                 155

<210> SEQ ID NO 35
<211> LENGTH: 480
<212> TYPE: DNA
<213> ORGANISM: Homo sapiens
<220> FEATURE:
<221> NAME/KEY: CDS
<222> LOCATION: (1)..(477)

<400> SEQUENCE: 35 atg gca gcg tcc gcc gga gcc ggg gcg gtg att gca gcc cca gac agc      48
Met Ala Ala Ser Ala Gly Ala Gly Ala Val Ile Ala Ala Pro Asp Ser
1               5                   10                  15 cgg cgc tgg ctg tgg tcg gtg ctg gcg gcg gcg att ggg ctc ttg aca      96
Arg Arg Trp Leu Trp Ser Val Leu Ala Ala Ala Ile Gly Leu Leu Thr
            20                  25                  30 gct gga gta tca gcc ttg gaa gta tat acg cca aaa gaa atc ttc gtg     144
Ala Gly Val Ser Ala Leu Glu Val Tyr Thr Pro Lys Glu Ile Phe Val
        35                  40                  45 gca aat ggt aca caa ggg aag ctg acc tgc aag ttc aag tct act agt     192
Ala Asn Gly Thr Gln Gly Lys Leu Thr Cys Lys Phe Lys Ser Thr Ser
    50                  55                  60 acg act ggc ggg ttg acc tca gtc tcc tgg agc ttc cag cca gag ggg     240
Thr Thr Gly Gly Leu Thr Ser Val Ser Trp Ser Phe Gln Pro Glu Gly
65                  70                  75                  80 gcc gac act act gtg tcg ttt ttc cac tac tcc caa ggg caa gtg tac     288
Ala Asp Thr Thr Val Ser Phe Phe His Tyr Ser Gln Gly Gln Val Tyr
                85                  90                  95 ctt ggg aat tat cca cca ttt aaa gac aga atc agc tgg gct gga gac     336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata     384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt     432
His Asn Gly Thr Tyr Ile Cys Asp Val Lys Asn Pro Pro Asp Ile Val
    130                 135                 140
```

-continued

```
gtc cag cct gga cac att agg ctc tat gtc gta gaa aaa gag aat tag    480
Val Gln Pro Gly His Ile Arg Leu Tyr Val Val Glu Lys Glu Asn
145                 150                 155
```

<210> SEQ ID NO 36
<211> LENGTH: 159
<212> TYPE: PRT
<213> ORGANISM: Homo sapiens

<400> SEQUENCE: 36

```
Met Ala Ala Ser Ala Gly Ala Gly Ala Val Ile Ala Ala Pro Asp Ser
 1               5                  10                  15

Arg Arg Trp Leu Trp Ser Val Leu Ala Ala Ile Gly Leu Leu Thr
            20                  25                  30

Ala Gly Val Ser Ala Leu Glu Val Tyr Thr Pro Lys Glu Ile Phe Val
            35                  40                  45

Ala Asn Gly Thr Gln Gly Lys Leu Thr Cys Lys Phe Lys Ser Thr Ser
     50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
                100                 105                 110

Leu Asp Lys Lys Asp Ala Ser Ile Asn Ile Glu Asn Met Gln Phe Ile
            115                 120                 125

His Asn Gly Thr Tyr Ile Cys Asp Val Lys Asn Pro Pro Asp Ile Val
        130                 135                 140

Val Gln Pro Gly His Ile Arg Leu Tyr Val Val Glu Lys Glu Asn
145                 150                 155
```

<210> SEQ ID NO 37
<211> LENGTH: 480
<212> TYPE: DNA
<213> ORGANISM: Homo sapiens
<220> FEATURE:
<221> NAME/KEY: CDS
<222> LOCATION: (1)..(477)

<400> SEQUENCE: 37

```
atg gca gcg tcc gcc gga gcc ggg gcg gtg att gca gcc cca gac agc     48
Met Ala Ala Ser Ala Gly Ala Gly Ala Val Ile Ala Ala Pro Asp Ser
 1               5                  10                  15 cgg cgc tgg ctg tgg tcg gtg ctg gcg gcg gcg ctt ggg ctc ttg aca     96
Arg Arg Trp Leu Trp Ser Val Leu Ala Ala Ala Leu Gly Leu Leu Thr
            20                  25                  30 gct gga gta tca gcc ttg gaa gta tat acg cca aaa gaa atc ttc gtg    144
Ala Gly Val Ser Ala Leu Glu Val Tyr Thr Pro Lys Glu Ile Phe Val
            35                  40                  45 gca aat ggt aca caa ggg aag ctg acc tgc aag ttc aag tct act agt    192
Ala Asn Gly Thr Gln Gly Lys Leu Thr Cys Lys Phe Lys Ser Thr Ser
     50                  55                  60 acg act ggc ggg ttg acc tca gtc tcc tgg agc ttc cag cca gag ggg    240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac    288
Ala Asp Thr Thr Val Ser Phe Phe His Tyr Ser Gln Gly Gln Val Tyr
                85                  90                  95 ctt ggg aat tat cca cca ttt aaa gac aga atc agc tgg gct gga gac    336
Leu Gly Asn Tyr Pro Pro Phe Lys Asp Arg Ile Ser Trp Ala Gly Asp
```

```
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata      384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt      432
His Asn Gly Thr Tyr Ile Cys Asp Val Lys Asn Pro Pro Asp Ile Val
    130                 135                 140 gtc cag cct gga cac att agg atc tat gtc gta gaa aaa gag aat tag      480
Val Gln Pro Gly His Ile Arg Ile Tyr Val Val Glu Lys Glu Asn
145                 150                 155

<210> SEQ ID NO 38
<211> LENGTH: 159
<212> TYPE: PRT
<213> ORGANISM: Homo sapiens

<400> SEQUENCE: 38

Met Ala Ala Ser Ala Gly Ala Gly Ala Val Ile Ala Ala Pro Asp Ser
 1               5                  10                  15

Arg Arg Trp Leu Trp Ser Val Leu Ala Ala Ala Leu Gly Leu Leu Thr
            20                  25                  30

Ala Gly Val Ser Ala Leu Glu Val Tyr Thr Pro Lys Glu Ile Phe Val
        35                  40                  45

Ala Asn Gly Thr Gln Gly Lys Leu Thr Cys Lys Phe Lys Ser Thr Ser
    50                  55                  60

Thr Thr Gly Gly Leu Thr Ser Val Ser Trp Ser Phe Gln Pro Glu Gly
65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Ile Tyr Val Val Glu Lys Glu Asn
145                 150                 155

<210> SEQ ID NO 39
<211> LENGTH: 480
<212> TYPE: DNA
<213> ORGANISM: Homo sapiens
<220> FEATURE:
<221> NAME/KEY: CDS
<222> LOCATION: (1)..(477)

<400> SEQUENCE: 39 atg gca gcg tcc gcc gga gcc ggg gcg gtg att gca gcc cca gac agc       48
Met Ala Ala Ser Ala Gly Ala Gly Ala Val Ile Ala Ala Pro Asp Ser
 1               5                  10                  15 cgg cgc tgg ctg tgg tcg gtg ctg gcg gcg gcg att ggg ctc ttg aca       96
Arg Arg Trp Leu Trp Ser Val Leu Ala Ala Ala Ile Gly Leu Leu Thr
            20                  25                  30 gct gga gta tca gcc ttg gaa gta tat acg cca aaa gaa atc ttc gtg      144
Ala Gly Val Ser Ala Leu Glu Val Tyr Thr Pro Lys Glu Ile Phe Val
        35                  40                  45 gca aat ggt aca caa ggg aag ctg acc tgc aag ttc aag tct act agt      192
Ala Asn Gly Thr Gln Gly Lys Leu Thr Cys Lys Phe Lys Ser Thr Ser
    50                  55                  60
```

-continued

```
acg act ggc ggg ttg acc tca gtc tcc tgg agc ttc cag cca gag ggg      240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac      288
Ala Asp Thr Thr Val Ser Phe Phe His Tyr Ser Gln Gly Gln Val Tyr
                 85                  90                  95 ctt ggg aat tat cca cca ttt aaa gac aga atc agc tgg gct gga gac      336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata      384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt      432
His Asn Gly Thr Tyr Ile Cys Asp Val Lys Asn Pro Pro Asp Ile Val
    130                 135                 140 gtc cag cct gga cac att agg atc tat gtc gta gaa aaa gag aat tag      480
Val Gln Pro Gly His Ile Arg Ile Tyr Val Val Glu Lys Glu Asn
145                 150                 155
```

<210> SEQ ID NO 40
<211> LENGTH: 159
<212> TYPE: PRT
<213> ORGANISM: Homo sapiens

<400> SEQUENCE: 40

```
Met Ala Ala Ser Ala Gly Ala Gly Ala Val Ile Ala Ala Pro Asp Ser
  1               5                  10                  15

Arg Arg Trp Leu Trp Ser Val Leu Ala Ala Ile Gly Leu Leu Thr
                 20                  25                  30

Ala Gly Val Ser Ala Leu Glu Val Tyr Thr Pro Lys Glu Ile Phe Val
             35                  40                  45

Ala Asn Gly Thr Gln Gly Lys Leu Thr Cys Lys Phe Lys Ser Thr Ser
         50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Ile Tyr Val Val Glu Lys Glu Asn
145                 150                 155
```

<210> SEQ ID NO 41
<211> LENGTH: 600
<212> TYPE: DNA
<213> ORGANISM: Homo sapiens
<220> FEATURE:
<221> NAME/KEY: CDS
<222> LOCATION: (1)..(597)

<400> SEQUENCE: 41

```
atg gca gcg tcc gcc gga gcc ggg gcg gtg att gca gcc cca gac agc       48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg ctc ttg aca       96
```

```
                                                          -continued

Arg Arg Trp Leu Trp Ser Val Leu Ala Ala Leu Gly Leu Leu Thr
            20                  25                  30 gct gga gta tca gcc ttg gaa gta tat acg cca aaa gaa atc ttc gtg     144
Ala Gly Val Ser Ala Leu Glu Val Tyr Thr Pro Lys Glu Ile Phe Val
        35                  40                  45 gca aat ggt aca caa ggg aag ctg acc tgc aag ttc aag tct act agt     192
Ala Asn Gly Thr Gln Gly Lys Leu Thr Cys Lys Phe Lys Ser Thr Ser
 50                  55                  60 acg act ggc ggg ttg acc tca gtc tcc tgg agc ttc cag cca gag ggg     240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac     288
Ala Asp Thr Thr Val Ser Phe Phe His Tyr Ser Gln Gly Gln Val Tyr
                85                  90                  95 ctt ggg aat tat cca cca ttt aaa gac aga atc agc tgg gct gga gac     336
Leu Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata     384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt     432
His Asn Gly Thr Tyr Ile Cys Asp Val Lys Asn Pro Pro Asp Ile Val
130                 135                 140 gtc cag cct gga cac att agg ctc tat gtc gta gaa aaa gag aat ttg     480
Val Gln Pro Gly His Ile Arg Leu Tyr Val Val Glu Lys Glu Asn Leu
145                 150                 155                 160 cct gtg ttt cca gtt tgg gta gtg gtg ggc ata gtt act gct gtg gtc     528
Pro Val Phe Pro Val Trp Val Val Val Gly Ile Val Thr Ala Val Val
                165                 170                 175 cta ggt ctc act ctg ctc atc agc atg att ctg gct gtc ctc tat aga     576
Leu Gly Leu Thr Leu Leu Ile Ser Met Ile Leu Ala Val Leu Tyr Arg
            180                 185                 190 agg aaa aac tct aaa cgg gat taa                                    600
Arg Lys Asn Ser Lys Arg Asp
        195

<210> SEQ ID NO 42
<211> LENGTH: 199
<212> TYPE: PRT
<213> ORGANISM: Homo sapiens

<400> SEQUENCE: 42

Met Ala Ala Ser Ala Gly Ala Gly Ala Val Ile Ala Ala Pro Asp Ser
  1               5                  10                  15

Arg Arg Trp Leu Trp Ser Val Leu Ala Ala Leu Gly Leu Leu Thr
            20                  25                  30

Ala Gly Val Ser Ala Leu Glu Val Tyr Thr Pro Lys Glu Ile Phe Val
        35                  40                  45

Ala Asn Gly Thr Gln Gly Lys Leu Thr Cys Lys Phe Lys Ser Thr Ser
 50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                85                  90                  95

Leu Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125
```

```
His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
                180                 185                 190

Arg Lys Asn Ser Lys Arg Asp
        195

<210> SEQ ID NO 43
<211> LENGTH: 600
<212> TYPE: DNA
<213> ORGANISM: Homo sapiens
<220> FEATURE:
<221> NAME/KEY: CDS
<222> LOCATION: (1)..(597)

<400> SEQUENCE: 43 atg gca gcg tcc gcc gga gcc ggg gcg gtg att gca gcc cca gac agc       48
Met Ala Ala Ser Ala Gly Ala Gly Ala Val Ile Ala Ala Pro Asp Ser
1               5                   10                  15 cgg cgc tgg ctg tgg tcg gtg ctg gcg gcg gcg ctt ggg ctc ttg aca       96
Arg Arg Trp Leu Trp Ser Val Leu Ala Ala Ala Leu Gly Leu Leu Thr
            20                  25                  30 gct gga gta tca gcc ttg gaa gta tat acg cca aaa gaa atc ttc gtg      144
Ala Gly Val Ser Ala Leu Glu Val Tyr Thr Pro Lys Glu Ile Phe Val
        35                  40                  45 gca aat ggt aca caa ggg aag ctg acc tgc aag ttc aag tct act agt      192
Ala Asn Gly Thr Gln Gly Lys Leu Thr Cys Lys Phe Lys Ser Thr Ser
    50                  55                  60 acg act ggc ggg ttg acc tca gtc tcc tgg agc ttc cag cca gag ggg      240
Thr Thr Gly Gly Leu Thr Ser Val Ser Trp Ser Phe Gln Pro Glu Gly
65                  70                  75                  80 gcc gac act act gtg tcg ttt ttc cac tac tcc caa ggg caa gtg tac      288
Ala Asp Thr Thr Val Ser Phe Phe His Tyr Ser Gln Gly Gln Val Tyr
                85                  90                  95 att ggg aat tat cca cca ttt aaa gac aga atc agc tgg gct gga gac      336
Ile Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata      384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt      432
His Asn Gly Thr Tyr Ile Cys Asp Val Lys Asn Pro Pro Asp Ile Val
    130                 135                 140 gtc cag cct gga cac att agg ctc tat gtc gta gaa aaa gag aat ttg      480
Val Gln Pro Gly His Ile Arg Leu Tyr Val Val Glu Lys Glu Asn Leu
145                 150                 155                 160 cct gtg ttt cca gtt tgg gta gtg gtg ggc ata gtt act gct gtg gtc      528
Pro Val Phe Pro Val Trp Val Val Val Gly Ile Val Thr Ala Val Val
                165                 170                 175 cta ggt ctc act ctg ctc atc agc atg att ctg gct gtc ctc tat aga      576
Leu Gly Leu Thr Leu Leu Ile Ser Met Ile Leu Ala Val Leu Tyr Arg
            180                 185                 190 agg aaa aac tct aaa cgg gat taa                                      600
Arg Lys Asn Ser Lys Arg Asp
        195
```

```
<210> SEQ ID NO 44
<211> LENGTH: 199
<212> TYPE: PRT
<213> ORGANISM: Homo sapiens

<400> SEQUENCE: 44

Met Ala Ala Ser Ala Gly Ala Gly Ala Val Ile Ala Ala Pro Asp Ser
  1               5                  10                  15

Arg Arg Trp Leu Trp Ser Val Leu Ala Ala Ala Leu Gly Leu Leu Thr
                 20                  25                  30

Ala Gly Val Ser Ala Leu Glu Val Tyr Thr Pro Lys Glu Ile Phe Val
             35                  40                  45

Ala Asn Gly Thr Gln Gly Lys Leu Thr Cys Lys Phe Lys Ser Thr Ser
         50                  55                  60

Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95

Ile Gly Asn Tyr Pro Pro Phe Lys Asp Arg Ile Ser Trp Ala Gly Asp
            100                 105                 110

Leu Asp Lys Lys Asp Ala Ser Ile Asn Ile Glu Asn Met Gln Phe Ile
        115                 120                 125

His Asn Gly Thr Tyr Ile Cys Asp Val Lys Asn Pro Pro Asp Ile Val
    130                 135                 140

Val Gln Pro Gly His Ile Arg Leu Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp
        195

<210> SEQ ID NO 45
<211> LENGTH: 600
<212> TYPE: DNA
<213> ORGANISM: Homo sapiens
<220> FEATURE:
<221> NAME/KEY: CDS
<222> LOCATION: (1)..(597)

<400> SEQUENCE: 45 atg gca gcg tcc gcc gga gcc ggg gcg gtg att gca gcc cca gac agc      48
Met Ala Ala Ser Ala Gly Ala Gly Ala Val Ile Ala Ala Pro Asp Ser
  1               5                  10                  15 cgg cgc tgg ctg tgg tcg gtg ctg gcg gcg gcg ctt ggg ctc ttg aca      96
Arg Arg Trp Leu Trp Ser Val Leu Ala Ala Ala Leu Gly Leu Leu Thr
                 20                  25                  30 gct gga gta tca gcc ttg gaa gta tat acg cca aaa gaa atc ttc gtg     144
Ala Gly Val Ser Ala Leu Glu Val Tyr Thr Pro Lys Glu Ile Phe Val
             35                  40                  45 gca aat ggt aca caa ggg aag ctg acc tgc aag ttc aag tct act agt     192
Ala Asn Gly Thr Gln Gly Lys Leu Thr Cys Lys Phe Lys Ser Thr Ser
         50                  55                  60 acg act ggc ggg ttg acc tca gtc tcc tgg agc ttc cag cca gag ggg     240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac     288
Ala Asp Thr Thr Val Ser Phe Phe His Tyr Ser Gln Gly Gln Val Tyr
```

```
ctt ggg aat tat cca cca ttt aaa gac aga atc agc tgg gct gga gac     336
Leu Gly Asn Tyr Pro Pro Phe Lys Asp Arg Ile Ser Trp Ala Gly Asp
        100                 105                 110 ctt gac aag aaa gat gca tca atc aac ata gaa aat atg cag ttt ata     384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt     432
His Asn Gly Thr Tyr Ile Cys Asp Val Lys Asn Pro Pro Asp Ile Val
    130                 135                 140 gtc cag cct gga cac att agg atc tat gtc gta gaa aaa gag aat ttg     480
Val Gln Pro Gly His Ile Arg Ile Tyr Val Val Glu Lys Glu Asn Leu
145                 150                 155                 160 cct gtg ttt cca gtt tgg gta gtg gtg ggc ata gtt act gct gtg gtc     528
Pro Val Phe Pro Val Trp Val Val Val Gly Ile Val Thr Ala Val Val
                165                 170                 175 cta ggt ctc act ctg ctc atc agc atg att ctg gct gtc ctc tat aga     576
Leu Gly Leu Thr Leu Leu Ile Ser Met Ile Leu Ala Val Leu Tyr Arg
            180                 185                 190 agg aaa aac tct aaa cgg gat taa                                     600
Arg Lys Asn Ser Lys Arg Asp
        195

<210> SEQ ID NO 46
<211> LENGTH: 199
<212> TYPE: PRT
<213> ORGANISM: Homo sapiens

<400> SEQUENCE: 46

Met Ala Ser Ala Gly Ala Gly Ala Val Ile Ala Ala Pro Asp Ser
  1               5                  10                  15

Arg Arg Trp Leu Trp Ser Val Leu Ala Ala Leu Gly Leu Leu Thr
                 20                  25                  30

Ala Gly Val Ser Ala Leu Glu Val Tyr Thr Pro Lys Glu Ile Phe Val
                 35                  40                  45

Ala Asn Gly Thr Gln Gly Lys Leu Thr Cys Lys Phe Lys Ser Thr Ser
     50                  55                  60

Thr Thr Gly Gly Leu Thr Ser Val Ser Trp Ser Phe Gln Pro Glu Gly
 65                  70                  75                  80

Ala Asp Thr Thr Val Ser Phe His Tyr Ser Gln Gly Gln Val Tyr
                     85                  90                  95

Leu Gly Asn Tyr Pro Pro Phe Lys Asp Arg Ile Ser Trp Ala Gly Asp
                100                 105                 110

Leu Asp Lys Lys Asp Ala Ser Ile Asn Ile Glu Asn Met Gln Phe Ile
                115                 120                 125

His Asn Gly Thr Tyr Ile Cys Asp Val Lys Asn Pro Pro Asp Ile Val
    130                 135                 140

Val Gln Pro Gly His Ile Arg Ile Tyr Val Val Glu Lys Glu Asn Leu
145                 150                 155                 160

Pro Val Phe Pro Val Trp Val Val Val Gly Ile Val Thr Ala Val Val
                165                 170                 175

Leu Gly Leu Thr Leu Leu Ile Ser Met Ile Leu Ala Val Leu Tyr Arg
            180                 185                 190

Arg Lys Asn Ser Lys Arg Asp
        195

<210> SEQ ID NO 47
```

```
<211> LENGTH: 600
<212> TYPE: DNA
<213> ORGANISM: Homo sapiens
<220> FEATURE:
<221> NAME/KEY: CDS
<222> LOCATION: (1)..(597)

<400> SEQUENCE: 47 atg gca gcg tcc gcc gga gcc ggg gcg gtg att gca gcc cca gac agc        48
Met Ala Ala Ser Ala Gly Ala Gly Ala Val Ile Ala Ala Pro Asp Ser
 1               5                  10                  15 cgg cgc tgg ctg tgg tcg gtg ctg gcg gcg gcg ctt ggg ctc ttg aca        96
Arg Arg Trp Leu Trp Ser Val Leu Ala Ala Ala Leu Gly Leu Leu Thr
             20                  25                  30 gct gga gta tca gcc ttg gaa gta tat acg cca aaa gaa atc ttc gtg       144
Ala Gly Val Ser Ala Leu Glu Val Tyr Thr Pro Lys Glu Ile Phe Val
         35                  40                  45 gca aat ggt aca caa ggg aag ctg acc tgc aag ttc aag tct act agt       192
Ala Asn Gly Thr Gln Gly Lys Leu Thr Cys Lys Phe Lys Ser Thr Ser
 50                  55                  60 acg act ggc ggg ttg acc tca gtc tcc tgg agc ttc cag cca gag ggg       240
Thr Thr Gly Gly Leu Thr Ser Val Ser Trp Ser Phe Gln Pro Glu Gly
 65                  70                  75                  80 gcc gac act act gtg tcg ttt ttc cac tac tcc caa ggg caa gtg tac       288
Ala Asp Thr Thr Val Ser Phe Phe His Tyr Ser Gln Gly Gln Val Tyr
             85                  90                  95 att ggg aat tat cca cca ttt aaa gac aga atc agc tgg gct gga gac       336
Ile Gly Asn Tyr Pro Pro Phe Lys Asp Arg Ile Ser Trp Ala Gly Asp
            100                 105                 110 ctt gac aag aaa gat gca tca atc aac ata gaa aat atg cag ttt ata       384
Leu Asp Lys Lys Asp Ala Ser Ile Asn Ile Glu Asn Met Gln Phe Ile
        115                 120                 125 cac aat ggc acc tat atc tgt gat gtc aaa aac cct cct gac atc gtt       432
His Asn Gly Thr Tyr Ile Cys Asp Val Lys Asn Pro Pro Asp Ile Val
    130                 135                 140 gtc cag cct gga cac att agg atc tat gtc gta gaa aaa gag aat ttg       480
Val Gln Pro Gly His Ile Arg Ile Tyr Val Val Glu Lys Glu Asn Leu
145                 150                 155                 160 cct gtg ttt cca gtt tgg gta gtg gtg ggc ata gtt act gct gtg gtc       528
Pro Val Phe Pro Val Trp Val Val Val Gly Ile Val Thr Ala Val Val
                165                 170                 175 cta ggt ctc act ctg ctc atc agc atg att ctg gct gtc ctc tat aga       576
Leu Gly Leu Thr Leu Leu Ile Ser Met Ile Leu Ala Val Leu Tyr Arg
            180                 185                 190 agg aaa aac tct aaa cgg gat taa                                       600
Arg Lys Asn Ser Lys Arg Asp
        195

<210> SEQ ID NO 48
<211> LENGTH: 199
<212> TYPE: PRT
<213> ORGANISM: Homo sapiens

<400> SEQUENCE: 48

Met Ala Ala Ser Ala Gly Ala Gly Ala Val Ile Ala Ala Pro Asp Ser
 1               5                  10                  15

Arg Arg Trp Leu Trp Ser Val Leu Ala Ala Ala Leu Gly Leu Leu Thr
             20                  25                  30

Ala Gly Val Ser Ala Leu Glu Val Tyr Thr Pro Lys Glu Ile Phe Val
         35                  40                  45

Ala Asn Gly Thr Gln Gly Lys Leu Thr Cys Lys Phe Lys Ser Thr Ser
```

```
                    50                  55                  60
Thr Thr Gly Gly Leu Thr Ser Val Ser Trp Ser Phe Gln Pro Glu Gly
 65                  70                  75                  80

Ala Asp Thr Thr Val Ser Phe Phe His Tyr Ser Gln Gly Gln Val Tyr
                 85                  90                  95

Ile Gly Asn Tyr Pro Pro Phe Lys Asp Arg Ile Ser Trp Ala Gly Asp
                100                 105                 110

Leu Asp Lys Lys Asp Ala Ser Ile Asn Ile Glu Asn Met Gln Phe Ile
            115                 120                 125

His Asn Gly Thr Tyr Ile Cys Asp Val Lys Asn Pro Pro Asp Ile Val
        130                 135                 140

Val Gln Pro Gly His Ile Arg Ile Tyr Val Val Glu Lys Glu Asn Leu
145                 150                 155                 160

Pro Val Phe Pro Val Trp Val Val Gly Ile Val Thr Ala Val Val
                165                 170                 175

Leu Gly Leu Thr Leu Leu Ile Ser Met Ile Leu Ala Val Leu Tyr Arg
                180                 185                 190

Arg Lys Asn Ser Lys Arg Asp
            195

<210> SEQ ID NO 49
<211> LENGTH: 15
<212> TYPE: PRT
<213> ORGANISM: Homo sapiens

<400> SEQUENCE: 49

Met Gly Ser Asn Lys Ser Lys Pro Lys Asp Ala Ser Gln Arg Arg
 1               5                  10                  15
```

It will be understood that various details of the invention may be changed without departing from the scope of the invention. Further, the foregoing description is for the purpose of illustrationonly, and not for the purpose of limitation--the invention being defined by the claims.

What is claimed is:

1. An isolated and punfied nucleic acid molecul that encodes a PZR polypeptide, wherein the encoded PZR polypeptide comprises an amino acid sequence as set forth in any of SEQ ID NOs:2, 4, 6, 8, 26, 28, 30 and 32.

2. The nucleic acid molecule of claim 1, further defined as comprising a PZR polypeptide-encoding nucleic acid sequence as set forth in any of SEQ ID NOs:1, 3, 5, 7, 25, 27, 29 and 31.

3. The nucleic acid molecule of claim 1, wherein the PZR polypeptide-encoding nucleic acid molecule is positioned under the control of a promoter.

4. The nucleic acid molecule of claim 1, further comprising a recombinant vector.

5. The nucleic acid molecule of claim 4, wherein the vector is a recombinant expression vector.

6. A recombinant host cell comprising the nucleic acid molecule of claim 1.

7. The recombinant host cell of claim 6, wherein the host cell is a procaryotic cell or is a eukaryotic cell.

8. A method of preparing a PZR polypeptide, comprising: transforming a cell with the nucleic acid molecule of claim 1 to produce a PZR polypeptide under conditions suitable for the expression of the polypeptide.

* * * * *